United States Patent
Cunningham et al.

(10) Patent No.: US 7,754,680 B2
(45) Date of Patent: Jul. 13, 2010

(54) PEPTIDES FOR BINDING CALCIUM CARBONATES AND METHODS OF USE

(75) Inventors: Scott D. Cunningham, Chadds Ford, PA (US); Steven Dale Ittel, Wilmington, DE (US); John P. O'Brien, Oxford, PA (US); Pierre E. Rouviere, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 497 days.

(21) Appl. No.: 11/828,539

(22) Filed: Jul. 26, 2007

(65) Prior Publication Data
US 2009/0029902 A1 Jan. 29, 2009

(51) Int. Cl.
*A61K 37/18* (2006.01)
*A61K 63/10* (2006.01)

(52) U.S. Cl. .............. 514/2; 530/300; 424/687

(58) Field of Classification Search .......... None
See application file for complete search history.

(56) References Cited

U.S. PATENT DOCUMENTS

| | | | |
|---|---|---|---|
| 6,057,429 A * | 5/2000 | Bieniarz et al. | 530/402 |
| 7,220,405 B2 | 5/2007 | Huang et al. | |
| 2002/0098524 A1 | 7/2002 | Murray et al. | |
| 2003/0148380 A1 | 8/2003 | Belcher | |
| 2003/0185870 A1 | 10/2003 | Grinstaff et al. | |
| 2005/0054752 A1 | 3/2005 | O'Brien et al. | |
| 2006/0035223 A1 | 2/2006 | Naik et al. | |
| 2006/0172282 A1 | 8/2006 | Naik et al. | |

FOREIGN PATENT DOCUMENTS

WO   WO 03/078451 A2   9/2003

OTHER PUBLICATIONS

Dashman, 1984, Soil Biol. Biochem., 16, 51-55.*
DeOliveira, 1997, J. Am. Chem. Soc., 119, 10627-10631.*
Adey et al., Characterization of Phage That Bind Plastic From Phage-Displayed Random Peptide Libraries, Gene, 1995, vol. 156:27-31.
Whaley et al., Selection of Peptides with Semiconductor Binding Specificity for Directed Nanocrystal Assembly, Nature, 2000, vol. 405:665-668.
DeOlveira et al., Control of Calcite Crystal Morphology by a Peptide Designed to Bind to a Specific Surface, J. Amer. Chem. Soc., 1997, vol. 119:10627-10631.
Wheeler et al., Surface Reactive Peptides and Polymers, American Chemical Society, 1991, (Book Not Included).
U.S. Appl. No 10/453,415, filed May 3, 2003, Jagota et al.

* cited by examiner

Primary Examiner—Andrew D Kosar
Assistant Examiner—Satyanarayana R Gudibande

(57) ABSTRACT

Combinatorially generated peptides are provided that have binding affinity for calcium carbonates. The peptides may be used to deliver benefit agents to various calcium carbonate surfaces.

48 Claims, 6 Drawing Sheets

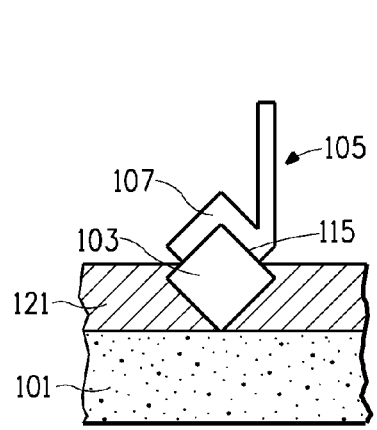
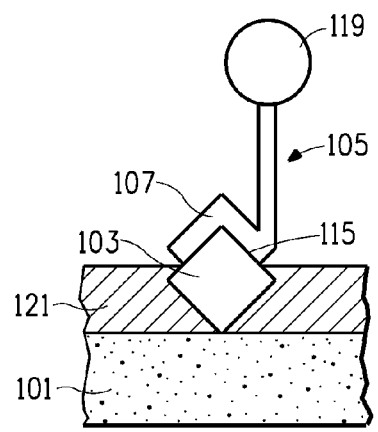
FIG. 2A          FIG. 2B
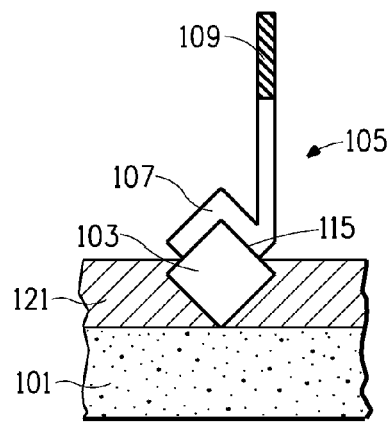
FIG. 2C
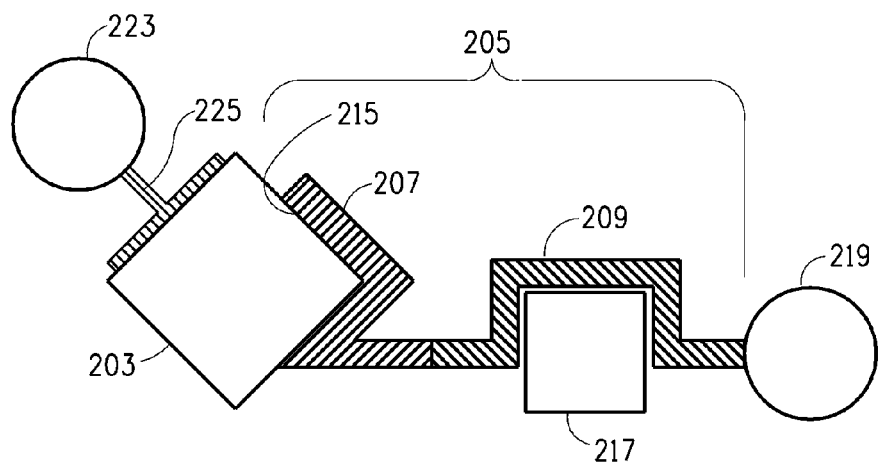
FIG. 3

PEPTIDES FOR BINDING CALCIUM CARBONATES AND METHODS OF USE

FIELD

Disclosed herein are peptide-based reagents having binding affinity for surfaces of calcium carbonate minerals and their use in various applications, such as papermaking, printing, and personal care.

BACKGROUND

Calcium carbonate minerals are spread throughout the world, which is why they have been among the most widely used raw materials for more than 5000 years. Although the deposits are plentiful, only a few are of sufficiently high quality to be worked and even a fewer number of deposits will provide raw materials for industrial and agricultural uses other than the construction and roads building industry. After quarrying, further treatment is required to process natural calcium carbonates of the highest quality, known generically as Ground Calcium Carbonate (GCC). Precipitated Calcium Carbonate (PCC) is a synthetic calcium carbonate produced industrially by means of a recarbonisation process. Both GCC and PCC can be used in a wide range of applications. For each end use there exists a tailor-made product, where fineness and particle size distribution are optimally balanced to meet the technical demands of that particular requirement.

Over the last 30 years, the use of calcium carbonate has grown significantly as technology in the paper industry has moved from acid to neutral sizing. Today, calcium carbonate is the most widely used mineral in papermaking. GCC and PCC are used both as a filler and a coating pigment, and help produce papers with high whiteness and gloss and good printing properties. Other uses of calcium carbonates include: a filler for breathable polyethylene films, the main extender for paints and coatings, a source of calcium in fertilizers, and a component in glass, ceramics, chalk, and dental care and cosmetic products.

Peptides having a binding affinity to polymer and semiconductor surfaces are known. For example, Adey et al., (*Gene* 156:27-31 (1995)) describe peptides that bind to polystyrene and polyvinyl chloride surfaces. Peptides that bind to polyurethane (Murray et al., U.S. Patent Application Publication No. 2002/0098524), polyethylene terephthalate (O'Brien et al., co-pending and commonly owned U.S. Patent Application Publication No. 2005/0054752), and polystyrene, polyurethane, polycarbonate, and nylon (Grinstaff et al., U.S. Patent Application Publication No. 2003/0185870) have been reported. Additionally, Whaley et al. (*Nature* 405:665-668 (2000)) and Belcher (U.S. Patent Application Publication No. 2003/0148380) disclose the use of phage display screening to identify peptide sequences that can bind specifically to different crystallographic forms of inorganic semiconductor substrates. The use of phage display to identify peptides that specifically bind carbon-based nanostructures is described by Jagota et al. (co-pending and commonly owned U.S. patent application Ser. No. 10/453,415; WO 03/102020).

Polyanionic peptides with an affinity for calcium carbonates are known (see for example, DeOlveira et al., *J. Amer. Chem. Soc.* 119:10627-10631 (1997), and Wheeler et al., *Surface Reactive Peptides and Polymers*, ACS Symposium Series 444, C. S. Sikes, ed.; American Chemical Society, Washington, D.C., 1991, Chapter 6). However, the use of such peptides to target and modify calcium carbonate surfaces has not been described.

There remains a need therefore for a peptide-based reagent that binds calcium carbonate minerals and offers flexibility in bringing a wide variety of materials to the calcium carbonate surface with minimum investment in redesign. Applicants have addressed the stated problem by providing calcium carbonate-binding peptide (CCBP) reagents comprising at least one calcium carbonate-binding peptide domain (CCBD). The calcium carbonate-binding peptides disclosed herein may further comprise other functional or binding peptide domains allowing for the delivery of benefit agents to the calcium carbonate surface or for the use of the reagents to adhere calcium carbonate-containing surfaces.

SUMMARY

Disclosed herein are calcium carbonate-binding domains that may be incorporated into calcium carbonate-binding peptide reagents useful for delivering functional compounds to a calcium carbonate surface. The calcium carbonate-binding peptides may comprise active domains that have linker or other functionality or target binding domains that bind various benefit agents that are delivered to the calcium carbonate surface.

Accordingly, one embodiment disclosed herein provides a peptide reagent having a general structure selected from the group consisting of:
a) $(CCBD)_n$;
b) $(CCBD_x\text{-}BA_p)_n$;
c) $(CCBD_x\text{-}AD_y)_n$;
d) $(CCBD_x\text{-}TBD_y)_n$;
e) $[(CCBD_x\text{-}L_s)_q\text{-}(TBD_y\text{-}L_t)_r]_n$;
f) $[(CCBD_x\text{-}L_s)_q\text{-}(CCBD_y\text{-}L_t)_r]_n$;
g) $(CCBD_x\text{-}L\text{-}BA)_n$; and
h) $[(CCBD)_q\text{-}L_x\text{-}(CCBD)_r]_n\text{-}L\text{-}BA$;
wherein:
i) CCBD is a calcium carbonate-binding domain having affinity for a calcium carbonate moiety;
ii) BA is at least one benefit agent;
iii) AD is at least one active domain incorporated into a calcium carbonate-binding peptide;
iv) TBD is at least one target-binding domain incorporated into a calcium carbonate-binding peptide;
v) L is a linker molecule;
vi) n, p, x, y, q, and r independently range from 1-20; and
vii) s and t are each independently 0 or 1, provided that both s and t may not be 0.

Another embodiment disclosed herein provides an affinity complex between a calcium carbonate and a peptide reagent having a general structure selected from the group consisting of:
a) $CC_m\text{-}(CCBD)_n$;
b) $CC_m\text{-}(CCBD_x\text{-}BA_p)_n$;
c) $CC_m\text{-}(CCBD_x\text{-}AD_y)_n$;
d) $CC_m\text{-}(CCBD_x\text{-}TBD_y)_n$;
e) $CC_m\text{-}[(CCBD_x\text{-}L_s)_q\text{-}(TBD_y\text{-}L_t)_r]_n$;
f) $CC_m\text{-}[(CCBD_x\text{-}L_s)_q\text{-}(CCBD_y\text{-}L_t)_r]_n$;
g) $CC_m\text{-}(CCBD_x\text{-}L\text{-}BA)_n$; and
h) $CC_m\text{-}[(CCBD)_q\text{-}L_x\text{-}(CCBD)_r]_n\text{-}L\text{-}BA$;
wherein:
i) CC is a calcium carbonate moiety;
ii) CCBD is a calcium carbonate-binding domain having affinity for the calcium carbonate moiety;
iii) BA is at least one benefit agent;
iv) AD is at least one active domain incorporated into a calcium carbonate-binding peptide;
v) TBD is at least one target-binding domain incorporated into a calcium carbonate-binding peptide;

vi) L is a linker molecule;
vii) m=the number of calcium carbonate moieties available for binding;
viii) n=is less than or equal to m;
ix) p, x, y, q, and r independently range from 1-20; and
x) s and t are each independently 0 or 1, provided that both s and t may not be 0.

Another embodiment disclosed herein provides a process of making paper containing a calcium carbonate comprising:
a) preparing a thickstock comprising cellulosic fibers, and a specific calcium carbonate;
b) making an aqueous thinstock suspension by diluting with water said aqueous thickstock suspension;
c) draining the water from the thinstock to form a sheet; and
d) drying the sheet;
wherein one or more peptide reagents, as described above, having a general structure:
$(CCBD_x\text{-}TBD_y)_n$ or $[(CCBD_x\text{-}L_s)_q\text{-}(TBD_y\text{-}L_t)_r]_n$ where CCBD is specific to the calcium carbonate used in step (a) and TBD is specific to cellulose, are added to:
i) the calcium carbonate of (a) before it's added to the thickstock;
ii) the thickstock of (a);
iii) the thinstock of (b); or
iv) any combination of (i), (ii), and (iii).

Another embodiment disclosed herein provides a process for producing a beneficiated and dewatered calcium carbonate comprising:
(a) providing a calcium carbonate for which beneficiation is desired;
(b) forming an aqueous suspension of said calcium carbonate;
(c) deflocculating said aqueous suspension;
(d) adding one or more peptide reagents, as described above, having the general structure:
$(CCBD)_n$ or $[(CCBD_x\text{-}L_s)_q\text{-}(CCBD_y\text{-}L_t)_r]_n$ where CCBD is specific to the calcium carbonate used in step (a) to produce a flocculated calcium carbonate product in the suspension; and
(e) separating said flocculated calcium carbonate product from the suspension.

Another embodiment disclosed herein provides a process for producing a calcium carbonate-coated paper or paperboard comprising the steps of:
a) forming a base stock;
b) preparing a coating formulation comprising a calcium carbonate and one or more peptide reagents, as described above, having the general structure $(CCBD_x\text{-}TBD_y)_n$ or $[(CCBD_x\text{-}L_s)_q\text{-}(TBD_y\text{-}L_t)_r]_n$, in water;
c) coating at least one side of the base stock with the coating formulation; and
d) passing the coated base stock through a calender device.

Another embodiment disclosed herein provides a process for identifying a calcium carbonate-binding peptide domain that will bind selectively to a single crystallographic face of a calcium carbonate mineral comprising the steps of:
(a) providing a library of combinatorially generated peptides;
(b) contacting the library of (a) with a single crystallographic face of a single crystal of said calcium carbonate mineral to form a reaction mixture comprising:
(i) peptide-calcium carbonate complex on said single crystallographic face;
(ii) uncomplexed peptides;
(c) isolating the peptide-calcium carbonate complex of (b);
(d) eluting the weakly bound peptides from the isolated peptide complex of (c) whereby the calcium carbonate-binding peptide domain that selectively binds to the single crystallographic face of a calcium carbonate mineral is isolated.

Yet another embodiment provides a process for preparing a precipitated calcium carbonate slurry comprising the steps of:
(a) providing an aqueous suspension of lime milk;
(b) adding to said lime milk, one or more peptide reagents comprising a calcium carbonate-binding peptide domain identified according to the process described above that binds selectively to a specific crystallographic face of calcium carbonate; and
(c) carbonating said lime milk by exposure to carbon dioxide under high shear conditions thereby forming the precipitated calcium carbonate slurry.

Additionally, other embodiments provide methods for binding a substrate comprising at least one calcium carbonate moiety to a target, for delivering a benefit agent to a substrate comprising calcium carbonate or a calcium carbonate moiety, and for adhering two surfaces.

BRIEF DESCRIPTION OF THE FIGURES AND SEQUENCE DESCRIPTIONS

The various embodiments of the invention can be more fully understood from the following detailed description, figures and the accompanying sequence descriptions, which form a part of this application.

FIG. 2 is a set of panels A-C which depict some embodiments disclosed herein as they are bound to a calcium carbonate coating containing, in whole or in part, calcium carbonate particles, which is further bound to a surface.

FIG. 3 depicts some embodiments disclosed herein as an affinity complex, optionally bound to a benefit agent at two different positions and/or a target molecule. Also depicted is the optional inclusion of a linker molecule and/or an active domain.

Figure 1A:
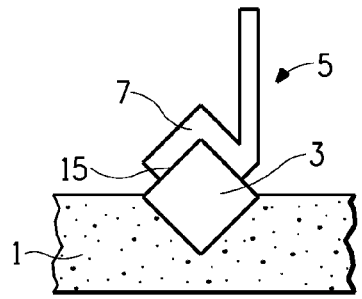
FIG. 1 is a set of panels A-E which depict some embodiments disclosed herein as they are bound to a surface containing, in whole or in part, calcium carbonate particles.
Figure 1B:
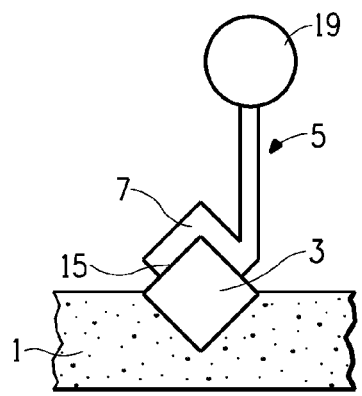
Figure 1C:
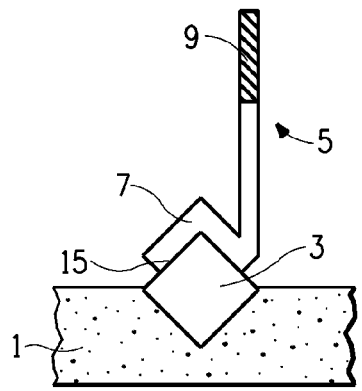
Figure 1D:
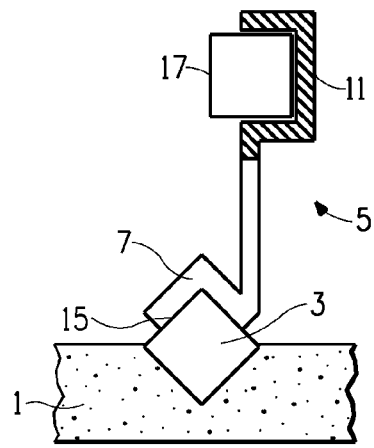
Figure 1E:
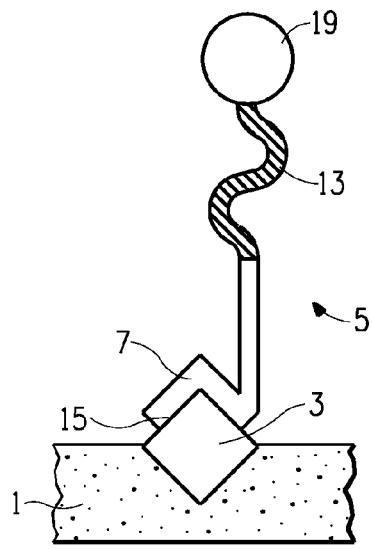

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs: 1-12 are poly(methyl methacrylate) (PMMA) binding peptide sequences.

SEQ ID NOs:13-41 are antimicrobial peptide sequences.

SEQ ID NOs: 42-66 are pigment binding peptide sequences.

SEQ ID NOs: 67-79 are print media binding peptide sequences, SEQ ID NOs: 67 and 68 bind to cotton fabric, SEQ ID NOs: 67 and 69 bind to polyester/cotton fabric, SEQ ID NOs: 67, and 70-72 bind to HAMERMILL® paper, SEQ ID NOs: 73-78 bind to cellulose, and SEQ ID NO: 79 binds to poly(ethylene terephthalate).

SEQ ID NOs: 80-175, and 195-198 are body surface binding peptide sequences, SEQ ID NOs: 80-87 are skin-binding peptide sequences, SEQ ID NOs: 88-175, and 195-198 are hair binding peptide sequences and SEQ ID NOs: 88 and 89 bind nails as well as hair.

SEQ ID NOs: 176-179 are amino acid sequences of peptide linker domains.

SEQ ID NOs: 180-185 are the amino acid sequences of nylon-binding peptides.

SEQ ID NOs: 186-194 are the amino acid sequences of poly(tetrafluoroethylene)-binding peptides.

SEQ ID NO: 199 is the amino acid sequence of the N-terminal constant region used in the present display library.

SEQ ID NO: 200 is the amino acid sequence of the C-terminal constant region used in the present display library.

SEQ ID NO: 201 is the nucleic acid sequence of the oligonucleotide portion of the MHA-oligonucleotide linker used in preparing the fusion molecules.

SEQ ID NOs: 202 and 203 are primers.

SEQ ID NOs: 204-231 are the amino acid sequences of calcium carbonate binding peptides (CCBP).

SEQ ID NO: 232 is the amino acid sequence of the Caspase 3 cleavage site that may be used as a peptide linker domain.

DETAILED DESCRIPTION

Disclosed herein are variable coatings for calcium carbonate substrates and surfaces. More specifically, peptide sequences that bind calcium carbonate with a high affinity are described. These peptides can be bound covalently or otherwise to known substances to adapt calcium carbonate for a variety of uses. Additionally, methods to develop, produce and use such peptides are described.

The following definitions and abbreviations are to be used for the interpretation of the claims and the specification.

As used herein, the term "comprising" means the presence of the stated features, integers, steps, or components as referred to in the claims, but that it does not preclude the presence or addition of one or more other features, integers, steps, components or groups thereof.

As used herein, the term "about" means modifying the quantity of an ingredient or reactant of the invention or employed and refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

"BA" means benefit agent.

"Calcium carbonate" means a calcium carbonate mineral.

"PCC" means precipitated calcium carbonate.

"GCC" means ground calcium carbonate.

"CCBP" means calcium carbonate-binding peptide. A calcium carbonate-binding peptide is a peptide having specific affinity for a calcium carbonate. Calcium carbonate-binding peptides of the present invention are single chain peptides no more than 200 amino acids in length. As such, the present calcium carbonate-binding peptides specifically exclude $F_{ab}$ fragments and single chain fused variable (scFv) antibody molecules. Calcium carbonate-binding peptides may comprise various subdomains including but not limited to active domains, target domains and linker domains. Within any given calcium carbonate binding peptide there resides a "calcium carbonate binding domain" (CCBD) having affinity to calcium carbonate. In one embodiment, the calcium carbonate-binding peptides are no more than 100 amino acids in length, preferably about 7 to about 100 amino acids in length, more preferably about 7 to about 60 amino acids in length, even more preferably about 7 to about 30 amino acids in length, and most preferably about 15 to about 30 amino acids in length.

The term "peptide" refers to a single chain polymer of two or more amino acids joined to each other by peptide bonds or modified peptide bonds.

The term "body surface" will mean any surface of the human body that may serve as a substrate for the binding of a peptide carrying a benefit agent. Typical body surfaces include but are not limited to hair, skin, nails, and teeth.

The term "benefit agent" is a general term applying to a compound or substance that may be coupled with a complex of calcium carbonate and calcium carbonate-binding peptide in order to provide a desirable characteristic of the benefit agent to the complex. In the most general sense a benefit agent may be any element, molecule or compound that is not a calcium carbonate-binding peptide. Benefit agents typically include colorants such as pigments and dyes as well as pharmaceuticals, markers, conditioners, and fragrances. Calcium carbonate itself may be a benefit agent because it may act as a pigment or a skin conditioning agent.

The term "hair" as used herein refers to human hair, eyebrows, and eyelashes.

The term "skin" as used herein refers to human skin, or substitutes for human skin, such as pig skin, VITRO-SKIN® and EPIDERM™. Skin as used herein as a body surface will generally comprise a layer of epithelial cells and may additionally comprise a layer of endothelial cells.

The term "nails" as used herein refers to human fingernails and toenails.

The terms "coupling" and "coupled" as used herein refer to any chemical association and includes both covalent and non-covalent interactions.

The term "pigment" refers to an insoluble, organic or inorganic colorant.

The term "print medium" refers to any substrate suitable for printing.

The term "dispersant" as used herein refers to a substance that stabilizes the formation of a colloidal solution of solid pigment particles in a liquid medium.

The term "active domain" as used herein applies to a subsequence of amino acids within a calcium carbonate-binding peptide. An active domain is a portion of the calcium carbonate binding peptide that is not responsible for calcium carbonate binding but provides additional functionality or benefit. In one embodiment for example an active domain may have antimicrobial functionality. In another embodiment the active domain may have a linker function between two other domains or between the peptide and a benefit agent. In another embodiment the active domain may serve to bind a specific target analyte (target domain).

The term "linking domain" or "linker domain" as used herein applies to a particular type of active domain that is used to either link two domains together, as a separator between two domains, or a domain and a terminal end. Linking domains may have a function beyond joining or separating two domains of a peptide.

The term "target binding domain" as used herein applies to a particular type of peptide active domain that binds a target molecule, element, compound, or complex. The binding substrate for the target-binding domain is referred to herein as the "target". Typical targets will include but are not limited to biological analytes, (cells, cell membrane fractions, viral proteins, proteins, antibodies, antibody fragments, nucleic acids and the like), plant fibers, synthetic fibers, as well as organic and inorganic target complexes that will typically be found on surfaces or in print media. All target-binding domains are active domains. A "body surface binding domain" is a target domain that has specific affinity for a body surface such as hair, skin, nails, teeth and the like. Similarly a "print media binding domain" will function to bind the elements of print media such as paper and other ink receptive surfaces. Within the context of print media domains, there may be those domains that bind cellulose or cotton or other plant fibers. Additionally the target domains disclosed herein may be selected to bind specific benefit agents such as colorants (pigments, dyes) and conditioners or any other organic or inorganic complex.

As used herein, "calcium carbonate moiety" is abbreviated "CC" means a discrete substance comprising a specific calcium carbonate that serves as a binding site for a calcium carbonate-binding peptide. Calcium carbonate moieties may make up a calcium carbonate particle, or be comprised within various calcium carbonate coatings on surfaces and substrates.

As used herein, the term "linker" or "spacer" or "linker molecule" or "spacer molecule" will be used interchangeably and will mean a molecule or compound used to bind a benefit agent to the calcium carbonate-peptide complex. Any material that can bind said benefit agent to the complex can be used, including peptide-based molecules. A linker molecule is distinct from a linker domain in that linker domains are inherently part of, or are proposed to be part of a peptide further comprising a calcium carbonate-binding domain. A linker molecule, in whole or in part, may be identical to a linking domain, but a linking molecule does not contain a calcium carbonate-binding domain.

As referred to herein a substance has "binding functionality" when it demonstrates specific affinity for a substance or target.

As referred to herein a substance has "catalytic functionality" when it demonstrates the ability to catalyze a chemical reaction.

As referred to herein a substance has "antimicrobial functionality" when it demonstrates the ability to kill microbial cell populations.

As used herein the term "surface" when used in conjunction with a calcium carbonate moiety means the point of contact for the calcium carbonate moiety. Surfaces disclosed herein may be coated with calcium carbonate or will typically themselves comprise calcium carbonate moieties. In some instances the surface disclosed herein may be layered or juxtaposed on a "secondary surface". A "secondary surface" will typically be coated or layered with the calcium carbonate surfaces disclosed herein.

As used herein, the term "affinity complex" refers to a complex between a calcium carbonate and a calcium carbonate-binding peptide reagent. The affinity complex may optionally comprise a benefit agent.

The term "stringency" as it is applied to the selection of calcium carbonate-binding peptides, hair-binding, skin-binding, and nail-binding peptides disclosed herein, refers to the concentration of the eluting agent (usually detergent) used to elute peptides from the substrate to which they are bound or for which they have affinity. Higher concentrations of the eluting agent provide more stringent conditions.

The term "thinstock" refers to a dilute aqueous suspension of cellulosic fibers and filler used in making filled paper.

The term "thickstock" refers to a concentrated aqueous suspension of cellulosic fibers and filler used in making filled paper. The thickstock is diluted, typically whitewater from the drainage stage, to prepare the thinstock.

The term "whitewater" refers to the filtrate water from the papermaking process. The terms thinstock, thickstock and whitewater are well known to those in the paper-making industry.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the process by which a gene's coded information is converted into the structures present and operating in the cell. Expressed genes include those that are transcribed into mRNA and then translated into protein and those that are transcribed into RNA but not translated into protein (e.g., transfer and ribosomal RNAs). Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purposes disclosed herein. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

The term "mRNA display" is an in vitro selection technique used to obtain peptides affinity that have an affinity for a target ligand/material from libraries of diverse sequences of peptides and proteins (U.S. Pat. No. 6,258,558). The process relies on mRNA-protein fusion molecules, which consist of peptide or protein sequences covalently linked via their C-termini to the 3' end of their own mRNA (these molecules are commercially referred to as PROFUSION™ molecules; Adnexus Therapeutics, Weltham, Mass.). The library of PROFUSION™ molecules is preferably subjected to reverse transcription (i.e. transcribed into a library of DNA/RNA-protein fusion molecules) prior affinity selection. The library of fusion molecules is subjected to repetitive rounds of in vitro selection in the presence of target (typically a solid or a material immobilized on a solid support). A series of washing steps are used to select the fusion molecules exhibiting an affinity for the target material. The stringency of the washing is adjusted to select the fusion molecules those with the highest affinity (the affinity of the fusion molecule for the target material is attributed to the specific peptide sequence displayed). Selected fusion molecules are then subsequently subjected to PCR amplification. The end result is a pool of nucleotide sequences encoding peptides which have an affinity for the target ligand. The process is typically repeated for several cycles and may also include mutagenesis (e.g. error prone PCR) to evolve and identify proteins having improved affinity for the target ligand.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

The disclosures herein relate to peptides and peptide reagents that have specific binding affinity to calcium carbonate in various conformations including complexes of the calcium carbonate-binding peptides linked to benefit agents, and optionally where the calcium carbonate-binding peptides comprise active peptide domains or target binding domains having binding or other functionality for other substances or surfaces. The peptide reagents disclosed herein may take a variety of forms including, but not limited to, those represented by the following structures:

a) $(CCBD)_n$;
b) $(CCBD_x\text{-}BA_p)_n$;
c) $(CCBD_x\text{-}AD_y)_n$;
d) $(CCBD_x\text{-}TBD_y)_n$;

e) $[(CCBD_x\text{-}L_s)_q\text{-}(TBD_y\text{-}L_t)_r]_n$;
f) $[(CCBD_x\text{-}L_s)_q\text{-}(CCBD_y\text{-}L_t)_r]_n$;
g) $(CCBD_x\text{-}L\text{-}BA)_n$; and
h) $[(CCBD)_q\text{-}L_x\text{-}(CCBD)_r]_n\text{-}L\text{-}BA$;

wherein:
i) CCBD is a calcium carbonate-binding domain having affinity for a calcium carbonate moiety;
ii) BA is at least one benefit agent;
iii) AD is at least one active domain incorporated into a calcium carbonate-binding peptide;
iv) TBD is at least one target-binding domain incorporated into a calcium carbonate-binding peptide;
v) L is a linker molecule;
vi) n, p, x, y, q, and r independently range from 1-20; and
vii) s and t are each independently 0 or 1, provided that both s and t may not be 0.

Alternatively, the calcium carbonate peptide reagents disclosed herein may be part of an affinity complex between a calcium carbonate and a peptide reagent represented by the general structures:
a) $CC_m\text{-}(CCBD)_n$;
b) $CC_m\text{-}(CCBD_x\text{-}BA_p)_n$;
c) $CC_m\text{-}(CCBD_x\text{-}AD_y)_n$;
d) $CC_m\text{-}(CCBD_x\text{-}TBD_y)_n$;
e) $CC_m\text{-}[(CCBD_x\text{-}L_s)_q\text{-}(TBD_y\text{-}L_t)_r]_n$;
f) $CC_m\text{-}[(CCBD_x\text{-}L_s)_q\text{-}(CCBD_y\text{-}L_t)_r]_n$;
g) $CC_m\text{-}(CCBD_x\text{-}L\text{-}BA)_n$; and
h) $CC_m\text{-}[(CCBD)_q\text{-}Lx\text{-}(CCBD)_r]_n\text{-}L\text{-}BA$;

wherein:
i) CC is a calcium carbonate moiety;
ii) CCBD is a calcium carbonate-binding domain having affinity for the calcium carbonate moiety;
iii) BA is at least one benefit agent;
iv) AD is at least one active domain incorporated into a calcium carbonate-binding peptide;
v) TBD is at least one target-binding domain incorporated into a calcium carbonate-binding peptide;
vi) L is a linker molecule;
vii) m=the number of calcium carbonate moieties available for binding;
viii) n=is less than or equal to m;
ix) p, x, y, q, and r independently range from 1-20; and
x) s and t are each independently 0 or 1, provided that both s and t may not be 0.

Calcium Carbonate Moieties

A calcium carbonate moiety (CC), as defined herein, is the binding site of a calcium carbonate-binding peptide on a surface. The calcium carbonate moiety may be incorporated into a surface in various ways. For example, the surface may be the surface of a calcium carbonate substrate. Alternatively, the calcium carbonate moiety may be imbedded into the surface of another material, such as a polymer, or coated on the surface of another material, such as a metal, polymer, glass, cloth, paper, and the like.

The term "calcium carbonate", as used and defined herein, refers to any calcium carbonate mineral. Suitable calcium carbonate minerals for use in the various embodiments disclosed herein include, but are not limited to, calcite, aragonite, Iceland spar, precipitated calcium carbonate (PCC), ground calcium carbonate (GCC), ankerite $Ca(Fe,Mg,Mn)(CO_3)_2$, benstonite $(Ba,Sr)_6(Ca,Mn)_6Mg(CO_3)_{13}$, dolomite $CaMg(CO_3)_2$, huntite $(CaMg_3(CO_3)_4)$, kutnohorite $(Ca(Mn,Mg,Fe)(CO_3)_2)$, minrecordite $(CaZn(CO_3)_2)$, and norsethite $(BaMg(CO_3)_2)$. Various calcium carbonate minerals are available commercially from companies such as Imerys (Roswell, Ga.), Minerals Technology Inc. (Specialty Minerals, Bethlehem, Pa.), Omya Inc. (Alpharetta, Ga.) and Solvay of Belgium represented by Solvay America, Inc. (Houston, Tex.).

Calcite is the primary calcium carbonate mineral. There are three minerals or phases of $CaCO_3$. Aragonite and vaterite are polymorphs. Aragonite is orthorhombic, vaterite is hexagonal and calcite is trigonal. Aragonite is a common mineral, but vaterite is scarce. Aragonite will convert to calcite over time and calcite pseudomorphs after aragonite are not uncommon.

Precipitated calcium carbonate (PCC) is derived from lime and has many industrial applications. PCC is made by hydrating high-calcium quicklime, and then reacting the resulting slurry, or "milk-of-lime", with carbon dioxide. The resulting product is extremely white and typically has a uniform narrow particle size distribution. PCC is available in numerous crystal morphologies and sizes, which can be tailored to optimize performance in a specific application.

In one embodiment, the calcium carbonate is coated onto another surface, such as metal, polymer, glass, cloth, paper, and the like, using methods known in the art, such as spraying, brushing, dip coating and casting. For example, calcium carbonate minerals are widely used in the paper industry as a coating pigment and as a filler. With the conversion to alkaline processing in the uncoated freesheet market and the continuing trend toward alkaline versus acid process papermaking in the coated, groundwood and paperboard markets, PCC is well established as a filler and coating pigment for premium quality paper products. PCC is typically produced in slurry form at satellite plants located near paper mills. PCC enhances optical properties and print characteristics of paper products, improves paper machine productivity and can reduce papermaking costs through the replacement of more expensive pulp fiber and optical brightening agents. Constantly improving quality targets make paper, and thus PCC, brightness an increasingly important factor. The use of calcium carbonate minerals in the paper industry is described in more detail below.

In another embodiment, the calcium carbonate is imbedded into the surface of another material, such as polymers, ceramics, rubbers, catalysts, and paints. This may be done by adding particles, beads, or fragments of calcium carbonate material into the other material as it is prepared.

Identification of Calcium Carbonate-Binding Peptide Domains

Peptides having affinity for calcium carbonate, referred to herein as calcium carbonate-binding peptides (CCBP), are peptide sequences that bind strongly to a calcium carbonate moiety. The calcium carbonate-binding peptides comprise at least one calcium carbonate binding domain (CCBD) and may further comprises various subdomains, including but not limited to active domains, target domains, and linker domains, as described above. Any given calcium carbonate-binding peptide may contain only the calcium carbonate binding domain or may contain the calcium carbonate binding domain in conjunction with one or more subdomains. The calcium carbonate-binding domain is the segment of the calcium carbonate-binding peptide that has a high binding affinity for a particular calcium carbonate. The calcium carbonate-binding domains are from about 7 amino acids to about 100 amino acids in length, more preferably from about 7 amino acids to about 60 amino acids in length, even more preferably from about 7 to about 30 amino acids in length, and most preferably about 15 to about 30 amino acids in length. Suitable calcium carbonate-binding domains may be selected using methods that are well known in the art.

The calcium carbonate-binding domains may be generated randomly and then selected against a calcium carbonate substrate based upon their binding affinity for a calcium carbonate, using the methods described by O'Brien et al. (co-pending and commonly owned U.S. Patent Application Publication No. 2005/0054752), Adey et al., (*Gene* 156:27-31, (1995)), Murray et al. (U.S. Patent Application Publication No. 2002/0098524) and Grinstaff et al. (U.S. Patent Application Publication No. 2003/0185870), all of which are incorporated herein by reference. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (Nos 5,449,754, 5,480,971, 5,585,275, 5,639,603), phage display technology (U.S. Pat. Nos. 5,223,409, 5,403,484, 5,571,698, 5,837,500), ribosome display technology (U.S. Pat. Nos. 5,643,768; 5,658,754; and 7,074,557), and mRNA display technology (U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; 6,436,665; 6,361,943; and 6,228,994). The calcium carbonate substrate may be in various forms, such as a powdered calcium carbonate, e.g., PCC or GCC, or a single crystal of calcium carbonate, as described below.

Phage Display

Phage display is a selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". As used herein, "biopanning" may be used to describe any selection procedure (phage display, ribosome display, mRNA-display, etc.) where a library of displayed peptides a library of displayed peptides is panned against a specified target material (e.g. a calcium carbonate). In its simplest form, phage display biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

Specifically, the calcium carbonate-binding domains may be selected using the following method. A suitable library of phage-peptides is generated using the methods described above or the library is purchased from a commercial supplier. After the library of phage-peptides has been generated, they are then contacted with an appropriate amount of the calcium carbonate substrate. The library of phage-peptides is dissolved in a suitable solution for contacting the substrate. The test substrate may be suspended in the solution or may be immobilized on a plate or bead. A preferred solution is a buffered aqueous saline solution containing a surfactant. A suitable solution is Tris-buffered saline (TBS) with 0.5% TWEEN® 20. The solution may additionally be agitated by any means in order to increase the mass transfer rate of the peptides to the calcium carbonate substrate, thereby shortening the time required to attain maximum binding.

Upon contact, a number of the randomly generated phage-peptides will bind to the calcium carbonate substrate to form a phage-peptide-substrate complex. Unbound phage-peptide may be removed by washing. After all unbound material is removed, phage-peptides having varying degrees of binding affinities for the calcium carbonate substrate may be fractionated by selected washings in buffers having varying stringencies. Increasing the stringency of the buffer used increases the required strength of the bond between the phage-peptide and calcium carbonate substrate in the phage-peptide-substrate complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P-40, Triton X-100, TWEEN® 20, wherein TWEEN® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that phage-peptides having increasing binding affinities for the calcium carbonate substrate may be eluted by repeating the selection process using buffers with increasing stringencies. The eluted phage-peptides can be identified and sequenced by any means known in the art.

In one embodiment, the following method for generating the calcium carbonate-binding peptides may be used. A library of combinatorially generated phage-peptides is contacted with a calcium carbonate substrate to form phage peptide-substrate complexes. The phage-peptide-substrate complex is separated from uncomplexed peptides and unbound substrate, and the bound phage-peptides from the phage-peptide-substrate complexes are eluted from the complex, preferably by acid treatment. Then, the eluted phage-peptides are identified and sequenced. To identify peptide sequences that bind to calcium carbonate but not to other substrates, a subtractive panning step may be added. Specifically, the library of combinatorially generated phage-peptides is first contacted with the non-target to remove phage-peptides that bind to it. Then, the non-binding phage-peptides are contacted with calcium carbonate and the above process is followed. Alternatively, the library of combinatorially generated phage-peptides may be contacted with the non-target and calcium carbonate simultaneously. Then, the phage-peptide-substrate complexes are separated from the phage-peptide-non-target complexes and the method described above is followed for the desired phage-substrate complexes.

Alternatively, a modified phage display screening method for isolating peptides with a higher affinity for calcium carbonate substrates may be used. In the modified method, the phage-peptide-substrate complexes are formed as described above. Then, these complexes are treated with an elution buffer. Any of the elution buffers described above may be used. Preferably, the elution buffer is an acidic solution. Then, the remaining, elution-resistant phage-peptide-substrate complexes are used to directly infect/transfect a bacterial host cell, such as *E. coli* ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for the substrate of interest. Alternatively, PCR may be used to identify the elution-resistant phage-peptides from the modified phage display screening method, described above, by directly carrying out PCR on the phage-peptide-substrate complexes using the appropriate primers, as described by Janssen et al. in U.S. Patent Application Publication No. 2003/0152976, which is incorporated herein by reference.

mRNA-Display

An in vitro method commonly used for identifying peptides having an affinity for a target material is mRNA-display (U.S. Pat. No. 6,258,558). Briefly, a random library of DNA molecules is generated wherein they encode a peptide of a desired length. The length of the peptide within the display library is may be to be up to 200 amino acids in length and is typically designed to range from about 7 to about 100 amino acids in length. In one embodiment, the library of peptides are designed to be about 7 to about 60 amino acids in length, preferably about 7 to about 30 amino acids in length, more preferably about 15 to about 30 amino acids in length, and most preferably about 27 amino acids in length (i.e. a "27-mer" library). Typically, the nucleic acid molecule encoding the peptide includes (in addition to the coding region) appropriate 5' and 3' regulatory regions necessary for efficient in vitro transcription and translation. The design of the nucleic acid constructs used for preparing the mRNA display library is well known to one of skill in the (see WO2005/051985). The nucleic acid molecules can be designed to optionally encode flexible linkers, cleavage sequences, fusion promoting sequences, and identification/purification tags (e.g., poly-A regions, His tags, etc.) to facility purification and/or processing in subsequence steps.

The library of random nucleic acid fragments is transcribed in vitro to produce an mRNA library. The mRNA is isolated and subsequently fused to a linker molecule (i.e. a puromycin-oligonucleotide linker or a puromycin derivative-oligonucleotide linker is used) using techniques well-known in the art (U.S. Pat. No. 6,258,558; U.S. Pat. No. 6,228,994; and Kurz et al., NAR, 28(18):e83 i-v (2000)). In a preferred embodiment, the puromycin-oligonucleotide linker comprises psoralen for rapid and facile preparation of the mRNA-protein fusions (Kurtz et al., supra). The mRNA-puromycin fusion molecules are then translated in vitro whereby the nascent polypeptide is fused (via the puromycin-oligonucleotide linker) to the mRNA (PROFUSION™ molecules; Adnexus Therapeutics, Weltham, Mass.). In this way, the phenotype (peptide) is linked to the corresponding genotype (RNA).

The mRNA-peptide fusion molecules are typically reverse transcribed into a DNA/mRNA-protein fusion molecules prior to affinity selection. The library (often comprising up to $10^{13}$ different sequences) is contacted with target ligand/material (typically an immobilized target and/or a solid surface). The selection process is carried out in an aqueous medium wherein parameters such as time, temperature, pH, buffer, salt concentration, and detergent concentration may be varied according the stringency of the selection strategy employed. Typically, the temperature of the incubation period ranges from 0° C. to about 40° C. and the incubation time ranges from about 1 to about 24 hours. The selection process is carried out in an aqueous medium wherein additional parameters such as pH, buffer, salt concentration, and detergent concentration may be varied according the stringency of the selection strategy employed.

Several washing steps are typically used to remove the non-binding/low affinity fusion molecules. The stringency of the washing conditions is adjusted to select those fusion molecules having the highest affinity for the target material (e.g. calcium carbonate). The high affinity fusion molecules are isolated and then PCR-amplified in order to obtain the nucleic acid sequences encoding the calcium carbonate-binding peptides. The mRNA display selection cycle is typically repeated for 3 to 10 cycles in order to select/enrich those fusion molecules comprising peptide sequences exhibiting the highest affinity for the target material.

Error prone PCR may optionally be incorporated into mRNA display selection process whereby mutants derived from a previously selected high affinity sequence are used. The process is typically repeated for several cycles in order to obtain the peptides having improved affinity for the target material.

Optionally, any calcium carbonate-binding peptide sequence identified using mRNA display is verified using the free peptide. Typically, the nucleic acid molecule encoding the calcium carbonate-binding peptide is cloned and recombinantly expressed in an appropriate microbial host cell, such as E. coli. The free peptide is then isolated and assayed against the targeted material to validate the binding affinity of the peptide sequence.

Binding Affinity

The present calcium carbonate-binding peptides exhibit a strong affinity for calcium carbonate. The affinity of the peptide for the calcium carbonate material can be expressed in terms of the dissociation constant $K_d$. $K_d$ (expressed as molar concentration) corresponds to the concentration of peptide at which the binding site on the target is half occupied, i.e., when the concentration of target with peptide bound (bound target material) equals the concentration of target with no peptide bound. The smaller the dissociation constant, the more tightly bound the peptide is; for example, a peptide with a nanomolar (nM) dissociation constant binds more tightly than a peptide with a micromolar (µM) dissociation constant. In one embodiment, the present calcium carbonate-binding peptides have a $K_d$ of $10^{-3}$ M or less, preferably $10^{-4}$ M or less, more preferably $10^{-5}$ M or less, even more preferably $10^{-6}$ M or less, yet even more preferably $10^{-7}$ M or less, and most preferably $10^{-8}$ M or less.

Alternatively, one of skill in the art can also use an ELISA-based assay to calculate a relative affinity of the peptide for the target material (reported as an $MB_{50}$ value; see present Example 4 and co-owned U.S. Patent Application Publication 2005/022683, herein incorporated by reference). As used herein, the term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with its corresponding substrate. In one embodiment, the $MB_{50}$ value (reported in terms of molar concentration) for the calcium carbonate-binding peptide is $10^{-5}$ M or less, preferably $10^{-6}$ M or less, more preferably $10^{-7}$ M or less, and most preferably $10^{-8}$ M or less.

Peptides that Bind to a Single Crystallographic Face of a Calcium Carbonate Mineral Calcium carbonate-binding peptide domains that bind selectively to a single crystallographic face of a calcium carbonate mineral may be identified using a slight modification to the methods described herein (as described in detail in Examples 5-7). Specifically, a single crystal of calcium carbonate, such as the rhombohedral, prismatic or scalenohedral forms of calcite, or the acicular form of aragonite, is used as the calcium carbonate substrate in the biopanning method. All but one of the faces of the crystal are masked and then the masked crystal is contacted with a library of combinatorially generated peptides and one of the biopanning methods described herein is followed. The faces of the crystal may be masked using various methods, such as painting them with an acrylic polymer or covering them with a chemically resistant and inert adhesive tape. The simplest method is to simply suspend the crystal above the solution with only the single surface of the crystal in contact with the solution. This approach eliminates the need for a masking composition thereby preventing the generation of peptides selective to that masking material.

Active Domains

As noted above active domains are peptide portions of the calcium carbonate binding peptide that convey an additional functionality to the peptide. Any sequence of amino acids may be used as an active domain, including, but not limited to those functioning as a linker, those having binding functionality, having catalytic functionality and those having antimicrobial functionality.

An antimicrobial active domain may be particularly desirable if the calcium carbonate moiety part of the affinity complex was for instance part of a kitchen countertop surface. Such antimicrobial sequences are well known in the art. Any peptide based antimicrobial sequence could be used as an active domain in the above embodiment. As non-limiting examples, Table 1 provides possible antimicrobial active domain sequences.

TABLE 1

Antimicrobial Active Domain Sequences

| Species of origin | SEQ ID NO. | Sequence |
|---|---|---|
| Artificial | 13 | PKGLKKLLKGLKKLLKL |
| Artificial | 14 | KGLKKLLKGLKKLLKL |
| Artificial | 15 | KGLKKLLKLLKKLLKL |
| Artificial | 16 | LKKLLKLLKKLLKL |
| Artificial | 17 | LKKLLKLLKKLL |
| Artificial | 18 | VAKKLAKLAKKLAKLAL |
| Artificial | 19 | FAKLLAKALKKLL |
| Artificial | 20 | KGLKKGLKLLKKLLKL |
| Artificial | 21 | KGLKKLLKLGKKLLKL |
| Artificial | 22 | KGLKKLGKLLKKLLKL |
| Artificial | 23 | KGLKKLLKLLKKGLKL |
| Artificial | 24 | KGLKKLLKLLKKLGKL |
| Artificial | 25 | FALALKALKKLKKALKKAL |
| Artificial | 26 | FAKKLAKLAKKLAKLAL |
| Artificial | 27 | FAKLLAKLAKKLL |

TABLE 1-continued

Antimicrobial Active Domain Sequences

| Species of origin | SEQ ID NO. | Sequence |
|---|---|---|
| Artificial | 28 | FAKKLAKLALKLAKL |
| Artificial | 29 | FAKKLAKKLL |
| Artificial | 30 | FAKLLAKLAKKVL |
| Artificial | 31 | KYKKALKKLAKLL |
| Artificial | 32 | FALLKALLKKAL |
| Artificial | 33 | KRLFKKLKFSLRKY |
| Artificial | 34 | KRLFKKLLFSLRKY |
| Artificial | 35 | LLLFLLKKRKKRKY |
| H. cecropia | 36 | KWKLFKKIEKVGQNIRDGIIKAGPAVAWGQATQIAK |
| Xenopus sp. | 37 | GIGKFLHSAKKFGKAFVGEIMNS |
| Xenopus sp. | 38 | GIGKFLKKAKKFGKAFVKILKK |
| Bos Taurus | 39 | RLCRIVVIRVCR |
| Bos sp. | 40 | ILPWKWPWWPWRR |
| H. sapiens | 41 | DSHAKRHHGYKRKFHEKHHSHRGY |

Two sub-types of active domains, target binding domains and linking domains, have been given specific names in the discussion disclosed herein. A target-binding domain is an active domain that specifically binds to a known target. Target binding sequences are known in the art and can be developed using known techniques as well as techniques described herein. Non-limiting examples of targets to which target binding domains will bind include, pigments, dyes, chemical functional groups, print media, body surfaces (hair, skin, nails, teeth etc.) and biological analytes (cells, receptors, proteins, nucleic acids, viral particles, prions, etc.) (see FIGS. 4, 5 and 6D).

Linking Domains

A linking domain is an active domain that is specifically used to separate two domains or a domain from a terminal end. Any sequence of amino acids that does not contain a calcium carbonate-binding site can be used as a linking domain. A linking domain can have activity beyond just separating two domains of a peptide. A linking domain may provide a specific structure to the separating portion of the peptide. Conversely, a linking domain may also be selected to provide flexibility to the separating portion of the peptide. Additionally the linking domain may be created to specifically change the rheology of the medium the peptide is immersed in. Also the linking domain may be constructed so that it can be cleaved by, or act as the binding site for, a cleaving molecule or enzyme, for the purpose of releasing a portion of the peptide and/or the calcium carbonate from the complex.

Preferred peptide linker domains are composed of the amino acids proline, lysine, glycine, alanine, and serine, and mixtures thereof. In addition, the linker domain may contain a specific enzyme cleavage site, such as the protease Caspase 3 site, given by SEQ ID NO: 232, which allows for the enzymatic removal of a portion of the peptide and/or the calcium carbonate from the complex. The peptide linker may be from 1 to about 50 amino acids, preferably from 1 to about 20 amino acids in length. Examples of peptide linkers include, but are not limited to, SEQ ID NOs: 176 to 179. These peptide linkers may be linked to the binding peptide sequence by any method know in the art. For example, the peptide reagent may be prepared using the standard peptide synthesis methods described below. In addition, the binding peptide and peptide linker domains may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides. Alternatively, the entire peptide reagent may be prepared using the recombinant DNA and molecular cloning techniques described below. The linker may also be a combination of a peptide linker and an organic linker molecule (described below), which may be prepared using the methods described above. Examples of specific linker peptides are given in Table 2.

TABLE 2

Linker Peptides

| Species of origin | SEQ ID NO. | Sequence |
|---|---|---|
| Artificial | 176 | LESGDEVD |
| Artificial | 177 | TSTSKASTTT TSSKTTTTSS KTTTTTSKTS TTSSSST |
| Artificial | 178 | GQGGYGGLGS QGAGRGGLGG QG |
| Artificial | 179 | GPGGYGPGQQ |

Target Domains

Target domains disclosed herein are another type of active domain comprised within the calcium carbonate binding peptide. Target domains will have binding affinity for various substance such as benefit agents (pigments, dyes, etc.), print media, biological analytes, body surfaces (hair, skin, nails, teeth, etc.), and the like.

Pigment binding domains are target domains that bind various pigments and colorants. Such pigments have application in the personal care as well as the printing industries. Similarly print media binding domains are target-binding domains having specific affinity for various types of print media. Typically the print media will comprise cotton or cellulose targets or may be coated with a polymer such as nylon or calcium carbonate giving rise to cotton, cellulose or polymer binding domains as part of the calcium carbonate-binding peptide.

Target domains may be uni-functional having binding affinity for a single target species or multifunctional, having affinity for a variety of targets. For example it may be desirable to combine a pigment binding domain or a print medium binding domain or both into the peptide part of the calcium carbonate-peptide complex disclosed herein. Such an embodiment that includes a print-medium binding domain may be particularly desirable if the complex already contains a benefit agent that is a colorant or dye. Pigment-binding peptides and print medium-binding peptides have been identified (See Tables 3, 4, and 5, and O'Brien et al., supra, hereby incorporated by reference). The pigment-binding peptides typically comprise at least about 40 mole % of the amino acids: glycine, alanine, valine, leucine, isoleucine, methionine, proline, phenylalanine, and tryptophan Specifically, binding peptides were isolated that have a high affinity for the pigments carbon black, given as SEQ ID NOs: 42-45, CRO-MOPHTHAL® Yellow, given as SEQ ID NOs: 46-53, SUNFAST® Magenta, given as SEQ ID NOs: 55-57, and SUNFAST® Blue, given as SEQ ID NOs: 54, 58-66. The cellulose-binding peptides disclosed herein comprise at least about 14 mole % of the amino acids: serine, threonine and tyrosine. Binding peptides having a high binding affinity for cellulose (a major component of cotton) include SEQ ID NOs: 73-78. The polyester-binding peptides disclosed herein comprise at least about 20 mole % of the amino acids: phenylalanine, tryptophan, and tyrosine. Binding peptides having a high affinity for polyester (poly(ethylene terephthalate)) include SEQ ID NO: 79. Additionally, binding peptides were isolated that have a binding affinity for the following print media: cotton, given as SEQ ID NOs: 67 and 68, polyester/cotton, given as SEQ ID NOs: 67 and 69, and printing paper, given as SEQ ID NOs: 67, and 70-72.

TABLE 3

Pigment-Binding Peptides

| Pigment | Designated Name | Peptide Sequence | SEQ ID NO: |
|---|---|---|---|
| Carbon Black | CB-71 | MPPPLMQ | 42 |
| | CB-72 | FHENWPS | 43 |
| | CB-121 | RTAPTTPLLLSL | 44 |
| | CB-122 | WHLSWSPVPLPT | 45 |
| Cromophtal ® Yellow | CY-71 | PHARLVG | 46 |
| | CY-72 | NIPYHHP | 47 |
| | CY-73 | TTMPAIP | 48 |
| | CY-74 | HNLPPRS | 49 |
| | CY-121 | AHKTQMGVRQPA | 50 |
| | CY-122* | ADNVQMGVSHTP | 51 |
| | CY-123* | AHNAQMGVSHPP | 52 |
| | CY-124* | ADYVGMGVSHRP | 53 |
| | CY-125 | SVSVGMKPSPRP | 54 |
| Sunfast ® Magenta | SM-71 | YPNTALV | 55 |
| | SM-72 | VATRIVS | 56 |
| | SM-121 | HSLKNSMLTVMA | 57 |
| Sunfast ® Blue | SB-71 | NYPTQAP | 58 |
| | SB-72 | KCCYSVG | 59 |
| | SB-121 | RHDLNTWLPPVK | 60 |
| | SB-122 | EISLPAKLPSAS | 61 |
| | SB-123 | SVSVGMKPSPRP | 54 |
| | SB-124** | SDYVGMRPSPRH | 62 |
| | SB-125** | SDYVGMRLSPSQ | 63 |
| | SB-126** | SVSVGIQPSPRP | 64 |
| | SB-127** | YVSVGIKPSPRP | 65 |
| | SB-128** | YVCEGIHPCPRP | 66 |

*These sequences are analogs of CY-121.
**These sequences are either analogs of SB-123 or are similar to the analogs of SB-123.

TABLE 4

Print Medium-Binding Peptides

| Print Medium | Designated Name | Peptide Sequence | SEQ ID NO: |
|---|---|---|---|
| Cotton fabric | COT-71* | SILPYPY | 67 |
|  | COT-72 | STASYTR | 68 |
| Polyester/cotton fabric | P/C-71 | LPVRPWT | 69 |
|  | P/C-72* | SILPYPY | 67 |
| Hammermill ® paper | HCP-71 | GNTPSRA | 70 |
|  | HCP-72 | HAIYPRH | 71 |
|  | HCP-73 | YQDSAKT | 72 |
|  | HCP-74* | SILPYPY | 67 |

*These sequences are identical.

TABLE 5

Cellulose and Poly(ethylene terephthalate)-Binding Peptides

| Print Medium Ingredient | Designated Name | Peptide Sequence | SEQ ID NO: |
|---|---|---|---|
| Cellulose | CEL-71 | VPRVTSI | 73 |
|  | CEL-72 | MANHNLS | 74 |
|  | CEL-73 | FHENWPS | 75 |
|  | CEL-121 | THKTSTQRLLAA | 76 |
|  | CEL-122 | KCCYVNVGSVFS | 77 |
|  | CEL-123 | AHMQFRTSLTPH | 78 |
| Poly(ethylene terephthalate) | PET-121 | GTSDHMIMPFFN | 79 |

Target domains that have binding affinity for body surfaces are particularly useful for the production of personal care compositions comprising colorants, and conditioners with specific binding affinity for the body surface. For example, it may be desirable to attach a calcium carbonate-peptide complex disclosed herein to a body surface such as hair or skin. One method to achieve such a result is to incorporate a target binding domain into the peptide part disclosed herein that binds hair, skin or another body surface. Alternatively, a calcium carbonate-binding peptide comprising a calcium carbonate-binding domain and a body surface-binding domain may be used to deliver a calcium carbonate, which serves as a benefit agent (e.g., a pigment or conditioner), to a body surface. Both hair and skin binding domains can be produced by the methods described here, in the co-pending, commonly owned U.S. patent application Ser. No. 10/935,642 (U.S. Patent Application Publication No. 2005/0050656) hereby incorporated by reference; and in co-pending, commonly owned U.S. patent application Ser. No. 11/074,473 (U.S. Patent Application Publication No. 2005/0226839) also hereby incorporated by reference. Examples of hair and skin binding domains are shown in Table 6.

TABLE 6

Body Surface Binding Peptide Domains

| Body Surface | SEQ ID NO | Sequence |
|---|---|---|
| Skin | 80 | FTQSLPR |
| Skin | 81 | TPFHSPENAPGS |
| Skin | 82 | KQATFPPNPTAY |
| Skin | 83 | HGHMVSTSQLSI |
| Skin | 84 | LSPSRMK |
| Skin | 85 | LPIPRMK |
| Skin | 86 | HQRPYLT |
| Skin | 87 | FPPLLRL |
| Nail | 88 | ALPRIANTWSPS |
| Nail | 89 | YPSFSPTYRPAF |
| Hair | 90 | YPSFSPTYRPAF |
| Hair | 91 | ALPRIANTWSPS |
| Hair | 92 | LESTPKMK |
| Hair | 93 | SVSVGMKPSPRP |
| Hair | 94 | LDVESYKGTSMP |
| Hair | 95 | RVPNKTVTVDGA |
| Hair | 96 | DRHKSKYSSTKS |
| Hair | 97 | KNFPQQKEFPLS |
| Hair | 98 | QRNSPPAMSRRD |
| Hair | 99 | TRKPNMPHGQYL |
| Hair | 100 | KPPHLAKLPFTT |
| Hair | 101 | NKRPPTSHRIHA |
| Hair | 102 | NLPRYQPPCKPL |
| Hair | 103 | RPPWKKPIPPSE |
| Hair | 104 | RQRPKDHFFSRP |
| Hair | 105 | SVPNK(T or P)VTVDG(E or A) |
| Hair | 106 | TTKWRHRAPVSP |
| Hair | 107 | WLGKNRIKPRAS |
| Hair | 108 | SNFKTPLPLTQS |
| Hair | 109 | KELQTRNVVQRE |
| Hair | 110 | GMPAMWIHPFA |
| Hair | 111 | TPTANQFTQSVP |
| Hair | 112 | AAGLSQKHERNR |
| Hair | 113 | ETVHQTPLSDRP |
| Hair | 114 | LPALHIQRHPRM |
| Hair | 115 | QPSHSQSHNLRS |
| Hair | 116 | RGSQKSKPPRPP |

TABLE 6-continued

Body Surface Binding Peptide Domains

| Body Surface | SEQ ID NO | Sequence |
|---|---|---|
| Hair | 117 | THTQKTPLLYYH |
| Hair | 118 | TKGSSQAILKST |
| Hair | 119 | DLHTVYH |
| Hair | 120 | HIKPPTR |
| Hair | 121 | HPVWPAI |
| Hair | 122 | MPLYYLQ |
| Hair | 123 | HLTVPWRGGGSAVPFYSHSQITLPNH |
| Hair | 124 | GPHDTSSGGVRPNLHHTSKKEKRENRKVPFYSHSVTSRGNV |
| Hair | 125 | KHPTYRQ |
| Hair | 126 | HPMSAPR |
| Hair | 127 | MPKYYLQ |
| Hair | 128 | MHAHSIA |
| Hair | 129 | TAATTSP |
| Hair | 130 | LGIPQNL |
| Hair | 131 | AKPISQHLQRGS |
| Hair | 132 | APPTPAAASATT |
| Hair | 133 | DPTEGARRTIMT |
| Hair | 134 | EQISGSLVAAPW |
| Hair | 135 | LDTSFPPVPFHA |
| Hair | 136 | LPRIANTWSPS |
| Hair | 137 | RTNAADHPAAVT |
| Hair | 138 | SLNWVTIPGPKI |
| Hair | 139 | TDMQAPTKSYSN |
| Hair | 140 | TIMTKSPSLSCG |
| Hair | 141 | TPALDGLRQPLR |
| Hair | 142 | TYPASRLPLLAP |
| Hair | 143 | AKTHKHPAPSYS |
| Hair | 144 | TDPTPFSISPER |
| Hair | 145 | CAAGCCTCAGCGACCGAATA |
| Hair | 146 | WHDKPQNSSKST |
| Hair | 147 | NEVPARNAPWLV |
| Hair | 148 | NSPGYQADSVAIG |
| Hair | 149 | TQDSAQKSPSPL |
| Hair | 150 | TPPELLHGDPRS |
| Hair | 151 | TPPTNVLMLATK |
| Hair | 152 | NTSQLST |
| Hair | 153 | NTPKENW |
| Hair | 154 | NTPASNR |
| Hair | 155 | PRGMLST |
| Hair | 156 | PPTYLST |
| Hair | 157 | TIPTHRQHDYRS |
| Hair | 158 | TPPTHRL |
| Hair | 159 | LPTMSTP |
| Hair | 160 | LGTNSTP |
| Hair | 161 | TPLTGSTNLLSS |
| Hair | 162 | TPLTKET |
| Hair | 163 | QQSHNPP |
| Hair | 164 | TQPHNPP |
| Hair | 165 | STNLLRTSTVHP |
| Hair | 166 | HTQPSYSSTNLF |
| Hair | 167 | SLLSSHA |
| Hair | 168 | QQSSISLSSHAV |
| Hair | 169 | NASPSSL |
| Hair | 170 | HSPSSLR |
| Hair | 171 | K(H, R or N)SHHTH |
| Hair | 172 | E(H, R, or N)SHHTH |
| Hair | 173 | LESTSLL |
| Hair | 174 | TPLTKET |
| Hair | 175 | KQSHNPP |
| Hair | 195 | STLHKYKSQDPTPHH |
| Hair | 196 | HDHKNQKETHQRHAA |
| Hair | 197 | HNHMQERYTDPQHSPSVNGL |
| Hair | 198 | TAEIDSSKNPNPHPQRSWTN |

Table 7 presents amino acid sequences displaying high affinity binding to poly(methyl methacrylate) (PMMA) that will find utility as described below.

TABLE 7

Amino Acid Sequences of High Affinity PMMA-Binding Peptides

| Clone ID | Amino Acid Sequence | SEQ ID NO: |
|---|---|---|
| A09 | IPWWNIRAPLNA | 1 |
| D09 | TAVMNVVNNQLS | 2 |
| A03 | VPWWAPSKLSMQ | 3 |

TABLE 7-continued

Amino Acid Sequences of High Affinity PMMA-Binding Peptides

| Clone ID | Amino Acid Sequence | SEQ ID NO: |
|---|---|---|
| A06 | MVMAPHTPRARS | 4 |
| B04 | TYPNWAHLLSHY | 5 |
| B09 | TPWWRIT | 6 |
| B01 | DLTLPFH | 7 |
| PB411 | GTSIPAM | 8 |
| P307 | HHKHVVA | 9 |
| P410 | HHHKHFM | 10 |
| P202 | HHHRHQG | 11 |
| PNM407 | HHWHAPR | 12 |

Using similar methods, target-binding domains having an affinity for cellulosic materials, lignin materials, and ligno-cellulosic materials may be identified. Suitable cellulosic materials, lignin materials, and ligno-cellulosic materials include, but are not limited to, wood pulp fibers; non-woody paper-making fibers from cotton; straws and grasses, including rice and esparto; canes and reeds, including bagasse; bamboos; stalks with bast fibers, including jute, flax, kenaf, cannabis, linen and ramie; and leaf fibers, including abaca and sisal; paper or polymer-coated paper and recycled paper. The cellulosic materials may be obtained from one or more soft-wood or hardwood wood sources, including pines, spruces, firs, oaks, maples, eucalyptuses, poplars, beeches, and aspens. The cellulosic material may be in the form of sawdust, wood chips, or wood flour.

Target domains may also be identified using the methods described above for polymers such as poly(methyl methacrylate) (PMMA; see Table 7), other acrylates and urethanes for use in automotive finishes or other paint products; natural or synthetic rubbers for use in rubber products; silicone materials for use in sealant products; and other polymers such as nylons (see Table 8), polyesters (see Table 5), polycarbonates, polyolefins, polyhydroxyalkanoates, and fluoropolymers (see Table 9). For additional examples of target domains, see Grinstaff et al. (U.S. Patent Application Publication No. 2003/0185870). Additionally, target domains may be identified for benefit agents used in personal care including, but not limited to, chelating agents, coloring agents, dispersants, emollients, emulsifiers, fragrances, humectants, opacifying agents, preservatives, skin conditioners, and thickeners for use in personal care products.

TABLE 8

Amino Acid Sequences of High Affinity Nylon-Binding Peptides

| Amino Acid Sequence | SEQ ID NO: |
|---|---|
| KTPPTRP | 180 |
| VINPNLD | 181 |
| KVWIVST | 182 |
| AEPVAML | 183 |
| AELVAML | 184 |
| HSLRLDW | 185 |

TABLE 9

Amino Acid Sequences of High Affinity Poly(tetrafluoroethylene)-Binding Peptides

| Amino Acid Sequence | SEQ ID NO: |
|---|---|
| ESSYSWSPARLS | 186 |
| GPLKLLHAWWQP | 187 |
| NALTRPV | 188 |
| SAPSSKN | 189 |
| SVSVGMKPSPRP | 190 |
| SYYSLPPIFHIP | 191 |
| TFTPYSITHALL | 192 |
| TMGFTAPRFPHY | 193 |
| TNPFPPPPSSPA | 194 |

Production of Calcium Carbonate-Binding Peptides

The calcium carbonate-binding peptides disclosed herein may be prepared using standard peptide synthesis methods, which are well known in the art (see for example Stewart et al., Solid Phase Peptide Synthesis, Pierce Chemical Co., Rockford, Ill., 1984; Bodanszky, Principles of Peptide Synthesis, Springer-Verlag, New York, 1984; and Pennington et al., Peptide Synthesis Protocols, Humana Press, Totowa, N.J., 1994). Additionally, many companies offer custom peptide synthesis services.

Alternatively, the calcium carbonate-binding peptides disclosed herein may be prepared using recombinant DNA and molecular cloning techniques. Genes encoding the calcium carbonate-binding peptides may be produced in heterologous host cells, particularly in the cells of microbial hosts, as described by Huang et al. (U.S. Patent Application Publication No. 2005/0050656) and O'Brien et al., supra.

Preferred heterologous host cells for expression of the binding peptides disclosed herein are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as Aspergillus, Trichoderma, Saccharomyces, Pichia, Candida, Hansenula, or bacterial species such as Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium and Klebsiella.

A variety of expression systems can be used to produce the peptides disclosed herein. Such vectors include, but are not limited to, chromosomal, episomal and virus-derived vectors, e.g., vectors derived from bacterial plasmids, from bacteriophage, from transposons, from insertion elements, from yeast episome, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these can be used to construct chimeric genes for production of the any of the binding peptides disclosed herein. These chimeric genes can then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in $E.\ coli$.

Initiation control regions or promoters which are useful to drive expression of the chimeric gene in the desired host cell are numerous and familiar to those skilled in the art. Virtually any promoter capable of driving the gene is suitable for producing the binding peptides disclosed herein including, but not limited to: CYC1, HIS3, GAL1, GAL10, ADH1, PGK, PHO5, GAPDH, ADC1, TRP1, URA3, LEU2, ENO, TPI (useful for expression in $Saccharomyces$); AOX1 (useful for expression in $Pichia$); and lac, ara, tet, trp, $P_L$, $P_R$, T7, tac, and trc (useful for expression in $Escherichia\ coli$) as well as the amy, apr, npr promoters and various phage promoters useful for expression in $Bacillus$.

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the peptides disclosed herein. Cell-free translation systems can also be employed to produce such peptides using RNAs derived from the DNA constructs disclosed herein. Optionally, it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Benefit Agents

Benefit agents are any material or substance that may be complexed with the calcium carbonate-binding peptide in a manner so as to deliver a benefit at the point where the calcium carbonate-binding peptide is attached. In the most general sense the benefit agent will be a component of an affinity complex comprising the calcium carbonate binding peptide. Any complex, compound or element may be used with the materials described herein as a benefit agent. If a user disclosed herein desires to have the features of a benefit agent combined with calcium carbonate then an affinity complex may be constructed to include the benefit agent in the formation with calcium carbonate and a calcium carbonate-binding peptide. A benefit agent may be selected for the purpose of adding the physical, chemical and/or biological properties of said agent to the calcium carbonate-peptide complex disclosed herein. The result of this construct will be said benefit agent closely associated with calcium carbonate and the activity of said benefit agent will be included within the affinity complex.

The affinity complex embodiment disclosed herein is composed of at least one member of each component but may also have multiple copies of identical or different members of one, two or all three components. Benefit agents can be used singularly or in a plurality. In some embodiments a plurality of peptide binding domains or a plurality of calcium carbonate particles or a plurality of both components may be added to a single benefit agent or a number of benefit agents. For some small benefit agents, for non-limited example, those composed of an element, as many as 10,000 benefit agents could be added to a single calcium carbonate-complex. For some large benefit agents, for non-limiting example, a dye embedded in a plastic bead as many as 100 calcium carbonate complexes might be attached to a single benefit agent.

Benefit agents may be inorganic or organic in nature, this includes being polymer or peptide based. The calcium carbonate itself may be a benefit agent which is delivered to another surface, such as a body surface. Some preferred embodiments include benefit agents that are pigments, pharmaceuticals, markers, conditioners, colorants, and fragrances.

Pharmaceuticals

A pharmaceutical generally means a substance dosed to an organism or thing to treat or prevent a disease or condition. A pharmaceutical benefit agent includes, in a non-limiting sense, the topical, internal or intracellular administration of a compound to an organism as a treatment or a prophylactic. A non-limiting example of this embodiment disclosed herein would be the attachment of an anti-acne medication to formulation disclosed herein designed to be a skin conditioner. A pharmaceutical benefit agent also includes a treatment to surface or item to prevent an infectious germ from being transmitted after contacting said surface or item. The addition of an antimicrobial compound to a construction disclosed herein to be used on countertops would be a non-limiting example of this embodiment. Suitable pharmaceuticals are well known in the art. An extensive list is given by Kabonov et al. in U.S. Pat. No. 6,696,089, which is incorporated herein by reference (in particular, columns 16 to 18). Examples include, but are not limited to, antibacterial agents, antiviral agents, antifungal agents, anti-cancer agents, vaccines, radiolabels, anti-inflammatories, anti-glaucomic agents, local anesthetics, anti-neoplastic agents, antibodies, hormones, and the like.

Markers

Markers as used and defined herein refer to a class of benefit agents that provide aid in detecting the presence of the calcium carbonate-peptide complex to which they are, or were, attached. The marker benefit agent might be a dye, fluorescent label, radioactive element or some other signal. Radioactive $P^{32}$ is a non-limiting example of this type of marker benefit agent. Also the marker benefit agent might also be a substance that reacts with a dye, fluorescent label or other signal. Biotin used in connection with a labeled-streptavidin compound is a non-limiting example of this type of marker benefit agent. Additionally a marker benefit agent might also provide, or help to provide aid to detect, the presence or lack of presence of another specific chemical, compound, element or complex. By way of non-limiting example, the marker benefit agent might be a compound that is metabolized by a specific enzyme to produce a metabolite that reacts with a fluorescently labeled phosphine. The Staudinger ligation is a non-limiting example of this type of marker benefit agent.

Conditioners

Conditioner benefits agents as referred to in discussion disclosed herein generally mean benefit agents that provide an improvement to the appearance, texture or quality of the substance they are designed to condition. Conditioner benefit agents may be used with the materials described herein to condition any substance including but not limited to hair, skin, lips, leather, and upholstery. In the preferred embodiment described herein are used in combination with a benefit agent that provides a conditioning effect to hair and skin. In the most preferred embodiment said hair and skin are human hair and human skin.

Hair conditioning agents as herein defined are agents that improve the appearance, texture, and sheen of hair as well as increasing hair body or suppleness. In the peptide-based hair conditioners disclosed herein, any known hair conditioning agent may be used. Hair conditioning agents are well known in the art, see for example Green et al. (WO 0107009), incorporated herein by reference, and are available commercially from various sources. Suitable examples of hair conditioning agents include, but are not limited to, cationic polymers, such as cationized guar gum, diallyl quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and volumizing agents, such as nanoparticles (e.g., silica nanoparticles and polymer nanoparticles). The preferred hair conditioning agents disclosed herein contain amine or hydroxyl functional groups to facilitate coupling to the hair-binding peptides. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

Skin conditioning agents as herein defined include, but are not limited to astringents, which tighten skin; exfoliants, which remove dead skin cells; emollients, which help maintain a smooth, soft, pliable appearance; humectants, which increase the water content of the top layer of skin; occlusives, which retard evaporation of water from the skin's surface; and miscellaneous compounds that enhance the appearance of dry or damaged skin or reduce flaking and restore suppleness. In the peptide-based skin conditioners disclosed herein, any known skin conditioning agent may be used. Skin conditioning agents are well known in the art, see for example Green et al. supra, and are available commercially from various sources. Suitable examples of skin conditioning agents include, but are not limited to, alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils and triglyceride esters. The preferred skin conditioning agents disclosed herein are polysalicylates, propylene glycol (CAS No. 57-55-6, Dow Chemical, Midland, Mich.), glycerin (CAS No. 56-81-5, Proctor & Gamble Co., Cincinnati, Ohio), glycolic acid (CAS No. 79-14-1, DuPont Co., Wilmington, Del.), lactic acid (CAS No. 50-21-5, Alfa Aesar, Ward Hill, Mass.), malic acid (CAS No. 617-48-1, Alfa Aesar), citric acid (CAS No. 77-92-9, Alfa Aesar), tartaric acid (CAS No. 133-37-9, Alfa Aesar), glucaric acid (CAS No. 87-73-0), galactaric acid (CAS No. 526-99-8), 3-hydroxyvaleric acid (CAS No. 10237-77-1), salicylic acid (CAS No. 69-72-7, Alfa Aesar), and 1,3 propanediol (CAS No. 504-63-2, DuPont Co., Wilmington, Del.). Polysalicylates may be prepared by the method described by White et al. in U.S. Pat. No. 4,855,483, incorporated herein by reference. Glucaric acid may be synthesized using the method described by Merbouh et al. (*Carbohydr. Res.* 336:75-78 (2001). The 3-hydroxyvaleric acid may be prepared as described by Bramucci in WO 02012530. Additionally, the calcium carbonate may serve as a skin conditioning agent.

The calcium carbonate may also serve as a conditioning agent for hair or skin. In this embodiment, the calcium carbonate is attached to the body surface using a calcium carbonate-binding peptide reagent comprising a calcium carbonate-binding domain and a body surface-binding domain. The body surface-binding domain binds to the body surface while the calcium carbonate-binding domain binds to the calcium carbonate, thereby attaching the calcium carbonate conditioning agent to the body surface. The calcium carbonate can serve as the conditioning agent directly or can serve to carry bound conditioning agents.

Colorants

The term colorant generally refers to a coloring agent. Colorants may be chemically organic or inorganic and may include pigments, lakes, or dyes. The peptide-based colorants disclosed herein may be prepared by covalently attaching a specific calcium carbonate-binding peptide to a coloring agent, either directly or via a linker, using any of the coupling methods known in the art (see for example, U.S. Patent Application Publication No. 2005/0226839).

Pigments are a particularly suitable benefit agent. Pigments generally means an insoluble colorant. A wide variety of organic and inorganic pigments alone or in combination may be used in the materials or methods described herein. Examples of organic pigments which are particularly useful for printing applications include, but are not limited to Cyan, Yellow, Red, Blue, Orange, Magenta, Black, Green, Violet, Light Cyan, and Light Magenta. Preferred organic pigments are carbon black, such as Carbon Black FW18, and colored pigments such as CROMOPHTHAL® Yellow 131AK (Ciba Specialty Chemicals), SUNFAST® Magenta 122 (Sun Chemical) and SUNFAST® Blue 15:3 (Sun Chemical). Examples of inorganic pigments which are particularly useful for printing applications include, but are not limited to finely divided metals, such as copper, iron, aluminum, and alloys thereof; and metal oxides, such as silica, alumina, and titania. Additional examples of suitable pigments are given by Ma et al. in U.S. Pat. No. 5,085,698, incorporated herein by reference.

The preferred coloring agents for use in the skin based applications disclosed herein include but are not limited to the following dyes: eosin derivatives such as D&C Red No. 21 and halogenated fluorescein derivatives such as D&C Red No. 27, D&C Red Orange No. 5 in combination with D&C Red No. 21 and D&C Orange No. 10, and the pigments: titanium dioxide, zinc oxide, D&C Red No. 36, D&C Red No. 30, D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red Nos. 12, the strontium lake D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; iron oxides, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, ultramarine blue, and carbon black.

The preferred coloring agents for use with the methods or materials described herein in the nail based applications include but are not limited to D&C Red Nos. 8, 10, 30 and 36, the barium lakes of D&C Red Nos. 6, 9 and 12, the calcium lakes of D&C Red Nos. 7, 11, 31 and 34, the strontium lake of D&C Red No. 30 and D&C Orange No. 17 and D&C Blue No. 6.

Suitable hair coloring agents for use with the methods or materials described herein include, but are not limited to dyes, such as 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36, D&C Red No. 30, and D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, iron oxides, zinc oxide, barium oxide, ultramarine blue, bismuth citrate, and carbon black particles.

The calcium carbonate may also serve as a pigment because of its inherent color. Additionally, the calcium carbonate may serve as a carrier for a dye, thus forming a lake pigment. In this embodiment, the calcium carbonate pigment is attached to the body surface using a calcium carbonate-binding peptide reagent comprising a calcium carbonate-binding domain and a body surface-binding domain. The body surface-binding domain binds to the body surface while the calcium carbonate-binding domain binds to the calcium carbonate pigment, thereby attaching the colorant to the body surface.

Fragrances

A fragrance is a complex, compound or element that releases, a substance which may be perceived by the sense of olfaction or chemical detection in any organism, but preferably, in humans. The object sensed or detected may be a part of or the whole of the fragrance benefit agent. In the preferred embodiment the odor is perceived as desirable to humans. However, some uses may combine the methods or materials described herein with a fragrance benefit agent that is repellent to a class of organisms, including a class that contains or is humans. Any known fragrance or odor may be use as a benefit agent. It may be desirable to attach a fragrance benefit agent to the calcium carbonate-peptide complex by a bond structure or linking molecule that allows the benefit agent to be released, in part or in whole, so that it may be perceived by a sensing organ or chemical detector.

Numerous fragrances, both natural and synthetic, are well known in the art. For example, Secondini (*Handbook of Perfumes and Flavors*, Chemical Publishing Co., Inc., New York, 1990), incorporated herein by reference, describes many of the natural and synthetic fragrances used in cosmetics. Suitable natural fragrances include, but are not limited, to jasmines, narcissus, rose, violet, lavender, mint, spice, vanilla, anise, amber, orange, pine, lemon, wintergreen, rosemary, basil, and spruce. Suitable synthetic fragrances include, but are no limited to, acetaldehyde, C7 to C16 alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

Organic Linker Molecules

Organic linker molecules may optionally be used with some embodiments disclosed herein for the purpose of attaching the benefit agent to the calcium carbonate-peptide complex (see FIG. 3, reference number 225). Additionally, the organic linker may be used instead of a peptide linker domain to couple the calcium carbonate-binding domain to another active domain. Multiple copies of the calcium carbonate-binding domain and the other active domain may be coupled through the linker molecule to enhance the strength of the interaction with the substrates. Any molecule, compound or complex that will attach the benefit agent to the complex or attach the two binding domains together can be used as a linking molecule provided the linking molecule does not contain calcium carbonate or a calcium carbonate-binding domain. The benefit agent may be attached to the complex to either the calcium carbonate moiety or the peptide portion or in the case of a plurality of benefit agent possibly to both. The linking molecules may be designed to bond the benefit agent in a stable form or in the alternative they may be designed to break and release the benefit agent from the complex in a given circumstance. Such circumstances could be, for non-limiting example, a range of pH, a range of temperatures, a range of pressure, while immersed in a certain media, the presence of a particular element, molecule or compound at a certain range of concentration, after a given passage of time, or at a certain average rate for a population of linker molecules.

Specifically the organic linker may be any of a variety of organic molecules, such as alkyl chains, phenyl compounds, ethylene glycol, amides, esters and the like. Preferred linkers are hydrophilic and have a chain length from 1 to about 100 atoms, more preferably, from 2 to about 30 atoms. Examples of preferred linkers include, but are not limited to, ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The linker may be covalently attached to the peptide and the benefit agent or the two binding domains using any of the coupling chemistries described above. In order to facilitate incorporation of the linker, a bifunctional cross-linking agent that contains a linker and reactive groups at both ends for coupling to the peptide and the benefit agent may be used. Suitable bifunctional cross-linking agents are well known in the art and include, but are not limited to diamines, such as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used.

Applications of Calcium Carbonate-Binding Peptides

It will be appreciated by the skilled person that calcium carbonate-binding peptides comprising active and target domains having specific functionality may be used in a multiplicity of formats including as delivery means for delivering benefits agents, in assays for diagnostic applications as well as in materials applications for coating substrate surfaces, such as printing on paper. Additionally, aqueous slurries of fine particle size calcium carbonates are used in a diverse range of end-use products. In many cases, the end-use performance is governed by the fineness of the particle size distribution. In turn, the maximum fineness of the particle size distribution is primarily determined by the efficiency of the dispersants used during the production process. The compositions described herein may be excellent dispersing agents and compatibilizers as a result of the high degree of stabilization achieved through biological selection of stabilizing affinity reagents. This may be utilized to produce more effective dispersant systems which provide added value, higher solids and finer particle size calcium carbonate slurry products.

The following description of the figures presents a limited number of additional examples of the methods disclosed herein, but is by no means inclusive of all possible applications and formats.

Referring to FIG. 1 panel A, there is shown a surface 1 comprising, in whole or in part, a calcium carbonate moiety 3. At least some of the calcium carbonate moieties 3 are exposed in various orientations on the exterior of the surface. The calcium carbonate-binding peptide 5 comprises at least one, but not limited to one, calcium carbonate-binding domain 7. The calcium carbonate-binding domain 7 further comprises at least one, but not limited to one, calcium carbonate-binding site 15. Calcium carbonate-binding peptides 5 will bind specifically to calcium carbonate moieties 3, this binding will occur at the calcium carbonate-binding site 15 of the calcium carbonate domain 7 within the calcium carbonate-binding peptide 5.

FIG. 1 panel B depicts another embodiment disclosed herein. In this embodiment, a calcium carbonate-binding peptide 5 also binds to a surface 1 comprising, in whole or in part, calcium carbonate moieties 3. A benefit agent 19 is coupled to the calcium carbonate-binding peptide 5 covalently, ionically or otherwise as described elsewhere herein. Although bound to the calcium carbonate-binding peptide 5, the benefit agent 19 generally retains the biological, chemical and physical properties that it exhibited before being coupled to the calcium carbonate-binding peptide 5. The combination of the calcium carbonate particle 3, the calcium carbonate-binding peptide 5, and the benefit agent 19 forms an affinity complex. The proximity of the benefit agent 19 to the surface 1 after binding allows the benefit agent 19 to be active at that location, and provides the chemical property of the benefit agent 19 on the calcium carbonate-containing surface 1. Non-limiting examples of the benefit agents 19 are colorants such as dyes and pigments, conditioners, fragrances, pharmaceuticals and the like.

FIG. 1 panel C depicts still another embodiment disclosed herein. The calcium carbonate-binding peptide 5 binds to a surface 1 comprising calcium carbonate moieties 3 as above. Panel C, as in panels A and B, shows the calcium carbonate-binding peptide 5 comprising at least one, but not limited to one, calcium carbonate-binding domain 7 within its structure. The calcium carbonate-binding domain 7 comprises at least one, but not limited to one, calcium carbonate-binding site 15. The calcium carbonate-binding peptide 5 of panel C further comprises at least one, but not limited to one, active domain 9 different from the calcium carbonate-binding domain 7, yet within the same calcium carbonate-binding peptide 5. By having an active domain 9 within the peptide 5 and the peptide 5 being bound to a calcium carbonate-containing surface 1 this embodiment disclosed herein allows the property of the active domain 9 to be transmitted to the surface 1. One non-limiting example of an active domain as exemplified here is a domain having antimicrobial properties.

FIG. 1 panel D depicts still another embodiment disclosed herein. The calcium carbonate-binding peptide 5 binds to a surface 1 comprising calcium carbonate moieties 3 as described above. In this embodiment, the calcium carbonate-binding peptide 5 comprises a specific target-binding domain 11 targeting other molecules other than calcium carbonate. In this embodiment, the calcium carbonate-binding peptide 1 acts as an intermediary to bring the target molecules close to the surface 1. This may be used to provide the chemical, biologic or physical function of target molecule 17 on the surface 1. However, this embodiment may also be employed to isolate the target molecule 17 from the surrounding media. Another use may be to sample the surrounding media for the presence of the target molecule 17. Non-limiting examples of the other target molecules 17 include benefit agents such as colorants (e.g., dyes and pigments) and conditioners as well as biological analytes, (cells, membrane fractions, viral particles, proteins, nucleic acids and the like), body surfaces, (hair, skin, nails, teeth and the like) as well as other organic and inorganic target complexes.

FIG. 1 panel E depicts still another embodiment disclosed herein. The calcium carbonate-binding peptide 5 binds to a surface 1 comprising calcium carbonate moieties 3 as above. Panel E depicts a calcium carbonate-binding peptide 5 that contains a linker domain 13 that serves to connect the calcium carbonate-binding peptide 5 to a benefit agent 19. The linker domain 13 is a domain that selected to physically separate the benefit agent 19 from the calcium carbonate-binding domain(s) 7. Alternatively, although not depicted in the FIG. 1, a single linker domain or many linker domains may be provided to separate various domains within the calcium carbonate-binding peptide. For instance, it may be advantageous to separate the calcium carbonate-binding domain from an active domain, or to separate two or more active domains, a linker could be utilized to achieve this separation. The linker domain 13 may simply provide a steric benefit. Although in some uses of this embodiment the linker provides a specific structure or orientation between the calcium carbonate-binding peptide 5 and the benefit agent 19 or to limit the conformation of the benefit agent-calcium carbonate-binding peptide-calcium carbonate affinity complex. In other uses of this embodiment the linker 13 provides a flexible region so that the benefit agent-calcium carbonate-binding peptide-calcium carbonate affinity complex can form a particular conformation or a variety of different conformations. Still, in other uses of this embodiment the chemical and physical nature of the linker 13 may be used to change the rheology of the environment surrounding the surface 1 to which the peptide 5 is bound. Non-limiting examples of linker domains 13 that would alter the rheology of the surrounding surface include hydrophobic, hydrophilic, or charged molecules. Additionally a linker domain 13 may be employed to release a benefit agent 19 from the calcium carbonate-binding peptide 5 under various circumstances. Such circumstances may include for example, a certain range of pH, or a certain range of temperatures, or a certain range of pressures. Such circumstances may also include response to shock, response to the presence of a particular molecule, especially a peptide cleaving molecule, or the passage of time.

Referring to FIG. 2 panel A, a surface 101 is shown that could be comprised of any surface material. Non-limiting examples of such surfaces are metal, paper, glass, rubber and cloth. A coating 121 comprised of in whole or in part, calcium carbonate moieties 103 have been applied to the surface 101 as shown. In this embodiment disclosed herein, a calcium carbonate-binding peptide 105 is targeted to the coating. As in the above descriptions the calcium carbonate-binding peptide 105 comprises, in whole or in part, at least one calcium carbonate-binding domain 107, which itself comprises, in whole or in part, at least one calcium carbonate-binding site 115. As described elsewhere herein the calcium carbonate-binding site 115 binds specifically to calcium carbonate moieties 103. In this embodiment the calcium carbonate-binding site 115 binds to exposed portions of calcium carbonate 103 in a calcium carbonate coating 121 on attached to the surface 101. In this embodiment the calcium carbonate-binding peptide 105 is useful to provide an additional coating to calcium carbonate coating 103 already applied to the surface 101. Non-limiting examples of the uses for this embodiment include a sacrificial layer to protect the calcium carbonate coating or in the case of multiple calcium carbonate domains 107 and/or binding sites 115 to act as an adhesive between the calcium carbonate coat 121 and other calcium carbonate moieties 103 or surfaces 101.

Similar to Panel A, FIG. 2 Panel B depicts a calcium carbonate-binding peptide 105 coupled to a calcium carbonate coating 121 on a surface 101. The calcium carbonate-binding peptide 105 depicted in panel B further comprises a benefit agent 119. In this embodiment disclosed herein, at least one, but not limited to one, benefit agent 119 is coupled to the calcium carbonate-binding peptide 105 by a covalent, ionic or other interactive means. The calcium carbonate-binding peptide-benefit agent affinity complex is in turn coupled to a calcium carbonate moiety 103 within the calcium carbonate coating 121 on the surface 101. As described elsewhere herein the benefit agent 119 has some activity or functionally that persists while it is bound to the calcium carbonate-binding peptide 105 and the complex is bound to the calcium carbonate coating 121. The active benefit agent 119 being brought to or near the coating 121 by the calcium carbonate-binding peptide 105 conveys its activity to the coating modifies the coating or enhances the coating. In a similar embodiment, a plurality of different types of calcium carbonate-binding peptides 105 may be used in combination so that the different benefit agents 119 corresponding to the different calcium carbonate-binding peptides 105 may interact, or act in concert to produce a desirable result. A non-limiting example of a use for this embodiment is to deliver a pigment to a calcium carbonate coating on paper for printing applications.

Similar to Panel A, FIG. 2 Panel C depicts a calcium carbonate-binding peptide 105 bound to a calcium carbonate coating 121 on a surface 101. The calcium carbonate-binding peptide 105 comprises all of the features of the calcium carbonate-binding peptide 105 depicted in Panel A, with the added feature that the peptide includes an active domain 109 separate from the calcium carbonate-binding domain. This active domain 109, remains active as part of the calcium carbonate-binding peptide 105, and further continues to be active when the calcium carbonate-binding peptide 105 binds to calcium carbonate moieties 103 within the calcium carbonate coating 121. The active domain 109, by virtue of being part of the affinity complex containing the calcium carbonate-binding peptide 105 and the calcium carbonate coating 121, is active in the proximity of the coating 121. This allows the coating 121 to exhibit the activity of the active domain 109 contained in the calcium carbonate-binding peptide 105 bound to the calcium carbonate moieties 103 contained within the coating 121. Additionally, as in panel B, a benefit agent 119 may also be chemically attached to the functional domain containing calcium carbonate-binding peptide 105 (not shown). As stated above, an additional embodiment would be the use of a plurality of different types of calcium carbonate-binding peptides 105 to interact or act in concert to produce a desirable result.

Referring to FIG. 3, another embodiment disclosed herein is shown in which the calcium carbonate is not bound to a larger surface. In this embodiment the calcium carbonate exists as a calcium carbonate moiety 203 which may be suspended in solution, such as cell growth media, air, water, oil, biological fluids, gels and the like. A calcium carbonate-binding peptide 205 is depicted bound to the calcium carbonate moiety 203. The calcium carbonate-binding peptide 205 contains within its peptide structure at least one, but not limited to one calcium carbonate-binding domain 207. The calcium carbonate-binding domain 207 contains within its structure a calcium carbonate-binding site 215. calcium carbonate-binding domains 207 and calcium carbonate-binding sites 215 bind calcium carbonate moieties 203 specifically as described elsewhere herein. Binding of the calcium carbonate-binding peptide 205 to the calcium carbonate 203 occurs at the calcium carbonate-binding site 215 with the calcium carbonate-binding domain 207. The binding of calcium carbonate moieties 203 to the calcium carbonate-binding peptide 205 forms an affinity complex. A non-limiting example of this embodiment is the use of the calcium carbonate-binding peptide as a dispersant to disperse calcium carbonate particles in solution, as described above.

Other embodiments disclosed herein add additional elements to the affinity complex of calcium carbonate moiety 203 and calcium carbonate-binding peptide 205. One such embodiment, involves binding a benefit agent 219 to the calcium carbonate-binding peptide 205. The benefit agent 219 may be coupled to the calcium carbonate-binding peptide 205 by any known means, as described above. The function of benefit agents 219 is discussed in greater detail elsewhere herein.

Alternatively the benefit agent 223 may be attached to the calcium carbonate moiety 203. In this format, the benefit agent 223 is attached to the calcium carbonate moiety or bead 203 typically by chemical means or bonds 225. The bond may be part of the benefit agent 223 or may be an independent structure that is bound to the calcium carbonate 203 for the purpose of binding the benefit agent 223. In the alternative, the bond structure 225 may be bound to the benefit agent 223 for the purpose of binding it to the calcium carbonate 203. The binding structure 225 may be a permanent bond, but in some forms of the embodiment may be easily broken under certain conditions. In other forms of the embodiment, the bond 225 may allow the benefit agent 223 to be leached from the calcium carbonate moiety or bead 203 under certain conditions. In still other forms of the embodiment, the bond 225 may allow the benefit agent 223 to be released over time at regular or specific time intervals. Alternatively, the bond 225, itself, may be in whole or in part be composed of calcium carbonate. In this way, the calcium carbonate moiety or bead 203 may be in whole or in part the binding structure 225. The benefit agent 223 may be partially or fully embedded with the calcium carbonate moiety or bead 203.

In another embodiment described by FIG. 3, the calcium carbonate-binding peptide 205 is bound the calcium carbonate 203 as described above and the complex may optionally be bound to a benefit agent 219 and/or 223 by any method described elsewhere herein. The additional feature of this embodiment is at least one or a plurality of additional active peptide domains 209 within the calcium carbonate-binding peptide 205. Any known peptide active domain 209 can be used in this embodiment. Alternatively, the active domain 209 may be a linker domain or may function as a target domain and bind a target 217. A non-limiting example of this embodiment is the attachment of calcium carbonate particles to the surface of paper or other print medium using a calcium carbonate-binding peptide that comprises a calcium carbonate-binding domain and a print medium binding domain.

Figure 4:
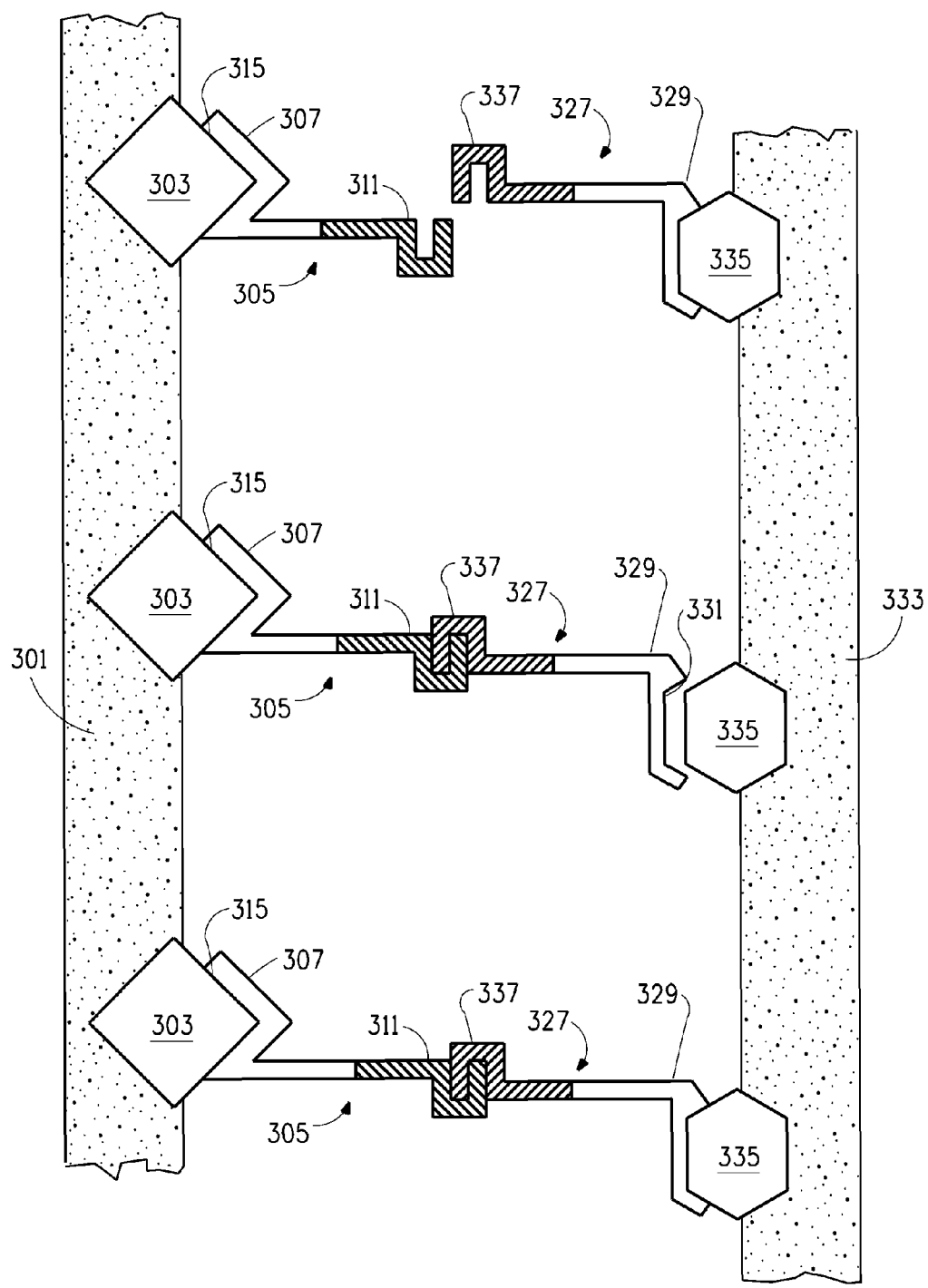
FIG. 4 depicts some embodiments disclosed herein used to bond a calcium carbonate containing surface with another surface which may contain calcium carbonate or another known target molecule.
Figure 5:
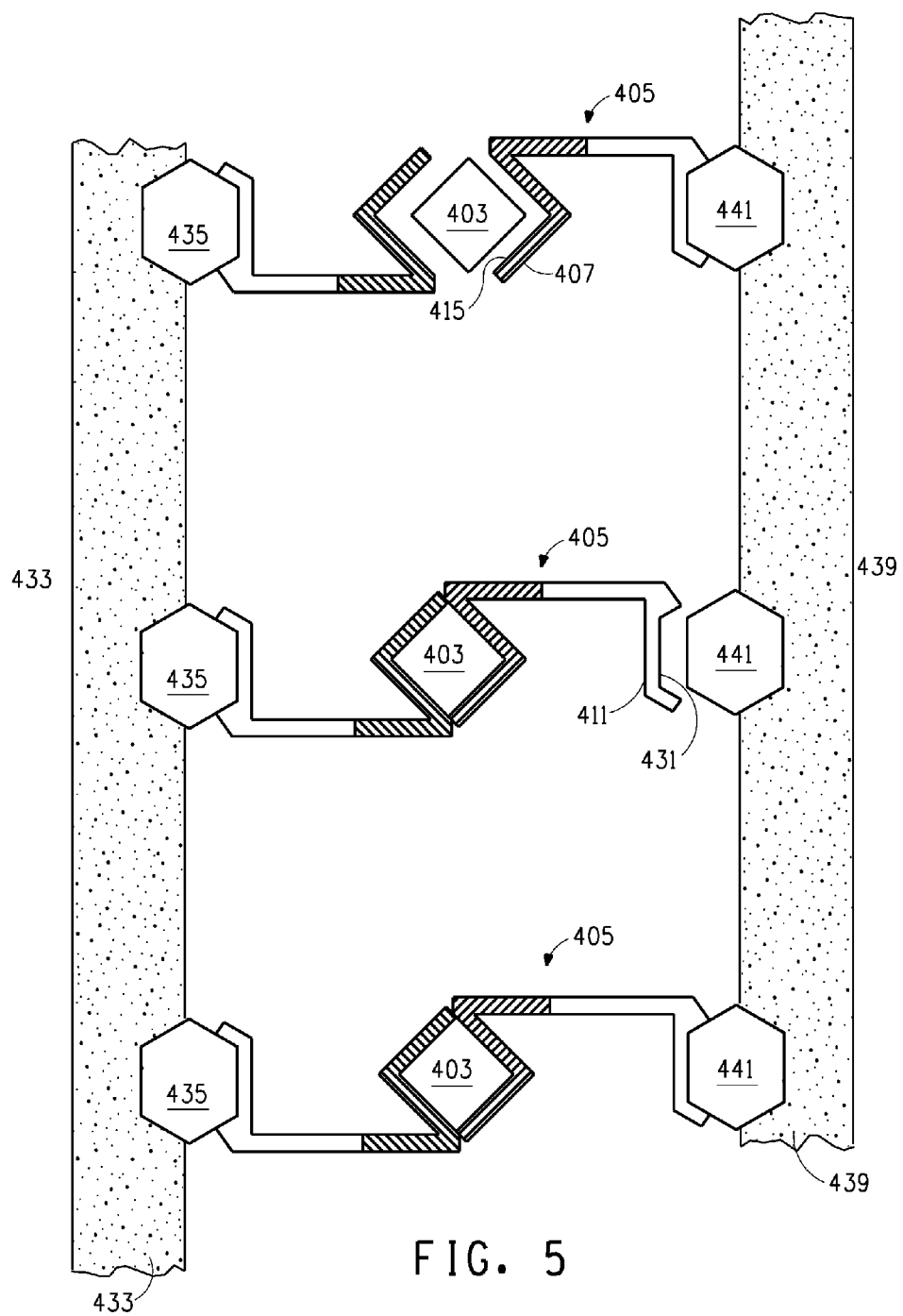
FIG. 5 depicts some embodiments disclosed herein used to bond two surfaces together wherein neither necessarily contains calcium carbonate.
Figure 6A:
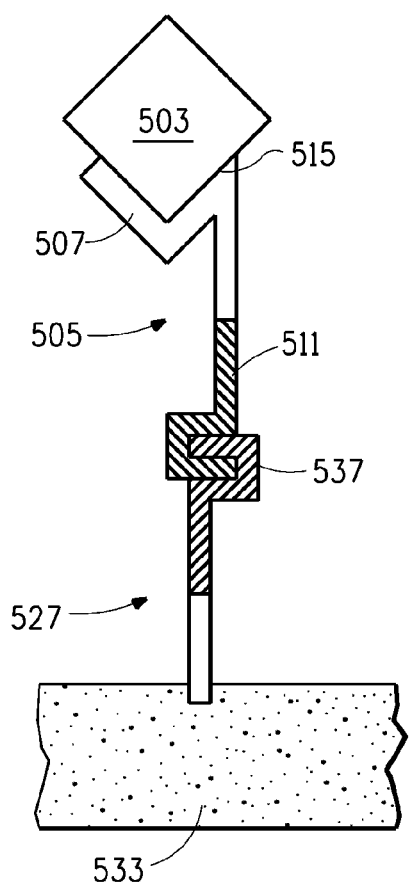
FIG. 6 is a set of panels A-D which depict some embodiments disclosed herein used to coat a surface with calcium carbonate.
Figure 6B:
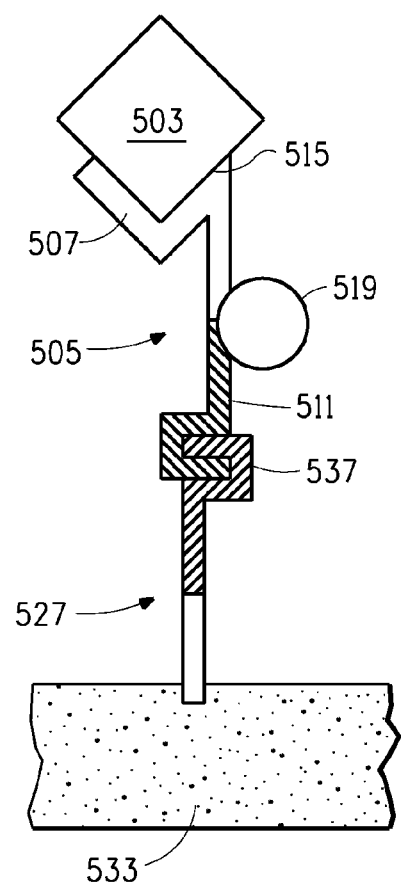
Figure 6C:
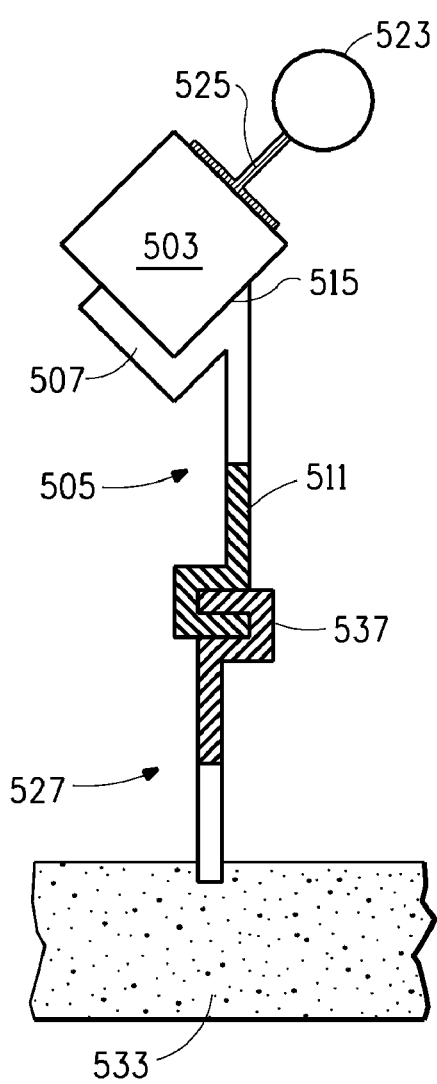
Figure 6D:
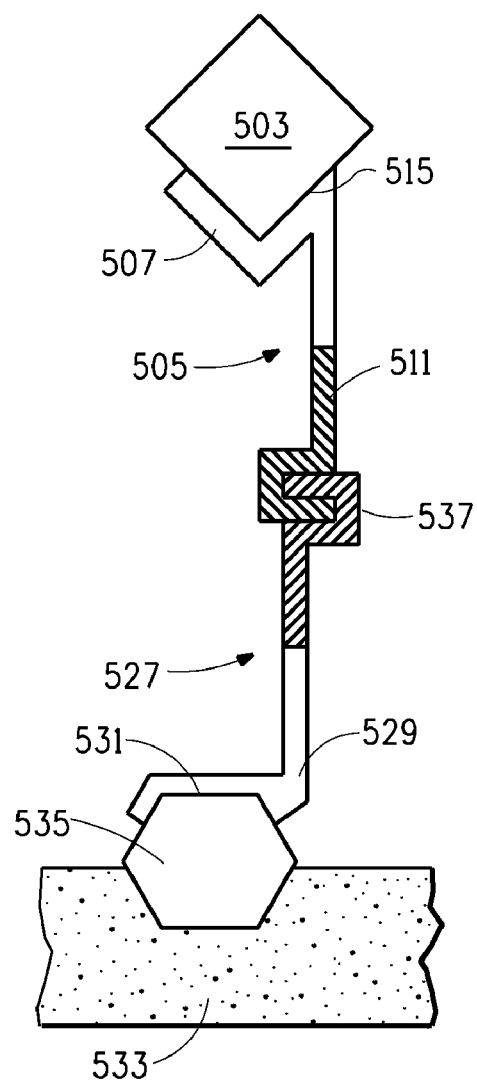

Additional embodiments disclosed herein are illustrated in FIGS. 4 and 5. Referring to FIGS. 4 and 5, a plurality of calcium carbonate-binding peptides 305 may be employed to bring substances together. FIG. 4 depicts a calcium carbonate-binding peptide 305 used to bring a calcium carbonate-containing surface 301 together with another surface 333. The calcium carbonate-containing surface 301 is comprised in whole or in part of calcium carbonate moieties 303. At least some calcium carbonate moieties 303 are exposed in part or in full on the at least one side of the surface 301. Likewise, the non-calcium carbonate surface or complementary surface 333 is comprised in whole or in part of a known moiety 335 for which there exists a peptide binding-domain 329 or for which a peptide binding domain 329 can be designed using the methods described elsewhere herein. The amino acid structure of the calcium carbonate-binding peptides 305 comprises in whole or in part of at least one calcium carbonate-binding domain 307, but possibly more than one. The calcium carbonate-binding domain 307, itself, comprises at least one or a plurality of calcium carbonate-binding sites 315. Calcium carbonate-binding sites 315 are able to bind to the exposed calcium carbonate moieties 303 of the calcium carbonate-containing surface 301 and in such way to adhere the calcium carbonate-binding peptides 305 to surface 301. In addition to comprising one or more calcium carbonate-binding domains 307, the calcium carbonate-binding peptide 305 of this embodiment also comprises at least one, but possibly more, target binding domains 311. The target binding domain 311 specifically binds another target domain 337 in a handshake fashion allowing the complex to serve as an adhesive binding the calcium carbonate and non-calcium carbonate-containing surfaces together. The target binding domain 311 in some uses may be capable of binding to itself. In that case, the target binding domain 311 and the target domain 337 could be identical.

The complementary surface 333 is composed a known surface-exposed moiety or a complementary moiety 335, for which there is a known peptide binding domain 329, a complementary peptide binding domain 329. A complementary moiety binding peptide 327 is composed of at least one, but possibly more than one, complementary moiety binding domain 329, which itself is composed of at least one but possibly more than one complementary moiety binding site 331. The complementary moiety binding site 331 binds specifically to complementary moieties 335 exposed on the complementary surface 333. The complementary moiety binding peptide 327 is bound to the complementary surface 333 because it is composed of at least one complementary moiety binding domain 329 which contains at least one complementary moiety binding site 331. In addition to the complementary moiety binding domain 329, the complementary moiety binding peptide 327 also contains at least one but possibly more than one target domain 337. As discussed above, the target binding domain 311 of the calcium carbonate-binding peptide 305 binds to the target domain 337.

It should be clear to one skilled in the art that the complementary surface 333 may be composed of calcium carbonate itself and the complementary moiety binding domain 327 could be a calcium carbonate-binding domain. This embodiment is useful because it provides an adhesive that is specific and functional even in adverse circumstances among such circumstances, as not limiting examples, are the presence of water, oil, or dirt.

FIG. 5 depicts another embodiment disclosed herein useful for binding two surfaces together. In this embodiment neither surface needs to necessarily contain calcium carbonate, although that possibility is not excluded. The primary structure of the peptide based adhesive is similar to that shown in FIG. 4. Two surfaces are provided 433, 439. Each surface comprising a target molecule 435, 441 either of which may or may not be the same and may or not be calcium carbonate. A reagent is provided comprising in each case a target binding peptide 405 with a target binding domain 411 comprising a target binding site 431. The target binding peptide 405 comprises a calcium carbonate-binding domain 407 having a calcium carbonate-binding site 415, useful for binding calcium carbonate moieties. Juxtaposing of the two surfaces in the presence of calcium carbonate moieties 403 results in adhesion of the surfaces though the calcium carbonate.

It will be apparent to the skilled person that this embodiment may also be practiced with the addition of a benefit agent(s) and/or peptide domain(s) as describe above. This embodiment is useful because it provides an adhesive that is specific and functional even in adverse circumstances among such circumstances, as not limiting examples, are the presence of water, oil, or dirt.

FIG. 6 depicts an embodiment disclosed herein in which a surface 533 may be coated with calcium carbonate 503 using calcium carbonate-binding peptide 505 containing a target binding domain 511. FIG. 6 panel A depicts a surface 533 coated with a target peptide 527 that contains in part or whole a target domain 537. The target peptide 527 may be applied to the surface 533 by any method either described herein or known in the art; one method will be described in detail later when discussing FIG. 6 panel D. The calcium carbonate-binding peptides 505 used in this embodiment each contain, as described above, at least one calcium carbonate-binding domain 507 which in turn contains at least one calcium carbonate-binding site 515. The calcium carbonate-binding site 515 binds calcium carbonate 503 specifically as described elsewhere herein. In addition to the calcium carbonate-binding domain 507, the calcium carbonate-binding peptides 505 also each contain at least one but possibly more than one target binding domain 511. The target binding domain used is selected, or created, using methods described or known, to bind specifically to the target domain 537 of the target peptide 527 on the surface 533. If the calcium carbonate-binding peptide 505 and calcium carbonate moieties 503 as described are allowed to move freely in a medium around the exposed surface 533, calcium carbonate-binding peptide 505 will adhere to the peptides 527 on the surface 533 through the bonding of the target binding domain 511 of the calcium carbonate-binding peptide 505 to the target domain 537 of the surface peptide 527. Calcium carbonate moieties in the media will bind to the calcium carbonate-binding site 515 of the calcium carbonate-binding domain 507 of the calcium carbonate-binding peptide 505 forming an affinity complex. With calcium carbonate 503 bound to the calcium carbonate-binding peptide 505 and it in turn bound to the surface peptides 527 that are bound to the surface 533, calcium carbonate 503 moieties will coat the surface 533.

FIG. 6 panel B, depicts the same interactions of calcium carbonate-binding peptide 505, calcium carbonate 503 and a peptide coated surface 533, as described in panel A, with the addition of a benefit agent 517 coupled to the calcium carbonate-binding peptide 505 which itself contains at least one target binding domain 511. Using methods described herein this embodiment couples a benefit agent 517 to the calcium carbonate-binding peptide 505. When the complex of the benefit agent 517 and the calcium carbonate-binding peptide 505 bind a calcium carbonate moiety 503 an affinity complex is formed. The affinity complex does not prevent the benefit agent 517 from being functionally active or from the target binding domain 511 from binding the target peptide 527. The addition of a benefit agent 517 to the calcium carbonate-binding peptide 505 allows the surface to be coated with both a benefit agent 519 and calcium carbonate moieties 503. Non-limiting examples of benefits agents 517 that may be used with this embodiment are dyes, colorants, antimicrobials, and stain repelling moieties.

FIG. 6, panel C, depicts the same interactions as in panel A, and provides the addition of a benefit agent 523 bound to calcium carbonate. In this embodiment, the benefit agent 523 is attached to the calcium carbonate moiety or bead 503 with a bond structure 525. The bonding structure may be part of the benefit agent 523 or may be an independent structure that is bound to the calcium carbonate 503 for the purpose of binding the benefit agent 523. Or in the alternative, the bond structure 525 may be bound to the benefit agent 523 for the purpose of binding it to the calcium carbonate 503. The binding structure 523 may be a permanent bond, but in some forms of the embodiment may be easily broken under certain conditions. In other forms of the embodiment the binding structure 525 may allow the benefit agent 523 to be leached from the calcium carbonate 503 under certain conditions. In still other forms of the embodiment the binding structure might allow the benefit agent 523 to be released over time at regular or specific time intervals or upon certain triggering events. In an alternative form of this embodiment the binding structure 525, itself, may be in whole or in part be composed of calcium carbonate. In this form, the calcium carbonate 503 may be in whole or in part the binding structure 525. The benefit agent 523 may be partially or fully embedded with the calcium carbonate 503. An affinity complex is formed when the benefit agent 523 coupled to the calcium carbonate moiety 503 that is in turn bound to the calcium carbonate-binding peptide 505. The affinity complex is capable of binding the target peptide as described above.

FIG. 6 panel D, Depicts a calcium carbonate-binding peptide 505 and calcium carbonate moiety or bead 503 similar to the calcium carbonate-binding peptide 505 described in panel A. In this embodiment, the target peptide 527 depicted is not attached directly to the surface 533. The target peptide 527 contains a target binding domain 537 as in panels A, B, and C and additionally contains a surface moiety binding domain 529. The surface moiety binding domain 529 is selected to bind specifically to a known moiety that is known to be exposed on the surface 533. The surface binding moiety domain 529 contains at least one, but possibly more than one, surface moiety binding site 531. The surface moiety binding site 531 is the point of attachment between the surface moiety 535 and the surface moiety binding domain 529. Through the interaction of the surface moiety binding domain 529 and the surface moiety 535 the calcium carbonate-binding peptide 505 is attached to the surface 533. Further through the binding interaction of the calcium carbonate moieties or beads 503 and calcium carbonate-binding peptide 505 bound to the surface 503, the surface 503 is coated with calcium carbonate moieties or beads 503.

Application of Calcium Carbonate-Binding Peptides in the Paper Industry

Industrial minerals have long been associated with paper-making and were originally used to reduce costs. For example, calcium carbonates are considerably cheaper than fiber, and this factor is still a consideration today. However, minerals also impart specific properties to the paper, such as improved printability, brightness, opacity, smoothness and dimensional stability.

Calcium carbonate fillers are considered a functional additive and are usually added to paper to enhance the optical (opacity and brightness) properties. Additional benefits of fillers include improved sheet formation, surface smoothness, printability and dimensional stability as well as reducing the furnish cost because of the favorable cost differential between fillers and fiber. However, the addition of filler interferes with the fiber-to-fiber bonding, as well as replacing some of the fiber, resulting in sheet strength reduction.

Consequently, the papermaker must manage the calcium carbonate filler level to optimize the benefits without sacrificing too much strength. Filler suppliers can manipulate the mineral properties such as particle size, particle shape, particle size distribution etc. in order to minimize the impact on strength. However, there are limits to these manipulations, especially with naturally occurring mineral fillers. Additionally, changes that improve strength generally reduce the optical and other benefits.

Kaolin was formerly the predominant mineral used in paper manufacturing, but with the advent of changes in papermaking chemistry in which the pH of the system switched from an acid regime to a neutral/alkaline one, calcium carbonate has taken over. Other mineral systems that may be employed include titanium dioxide and zirconium orthosilicate. Such systems are used more as a specialty chemical to impart specific end-use properties rather than as filler due to cost considerations. Titanium dioxide is used for its opacity properties, particularly in lightweight papers such as Bible paper.

Fillers are not simply inert optical entities; they interact with other additives, not only in terms of their own distribution but also to influence sheet structure, e.g. formation, bulk, pore structure and surface topography (texture). Aside from their optical effects, fillers or filler blends can be used to improve aspects of product uniformity and quality. Mastery of this technology requires an understanding of filler interactions with retention aids, sizing agents, cationic starch and the dynamics of the wet end forming system.

The main disadvantage of higher calcium carbonate filler level is the deterioration of fiber-to-fiber bonding. This leads to lower stiffness and strength (above that resulting from higher density). The main thrust of high filler technology is to overcome the problems with reduced strength. As mentioned earlier, apart from the loss in strength, changes in product quality are seen to be aesthetic: poor "feel", low rattle and a general feeling of limpness. Surface dusting is higher as well as a tendency to an increased propensity to pick. As mentioned previously, the need for refining is increased to achieve the same strength levels. Finally a more efficient retention system will be necessary to cope with the increase.

Filled paper may be made by a process comprising providing a dilute aqueous suspension (termed a thinstock) of cellulosic fibers and filler, draining the thinstock suspension to form a sheet, and drying the sheet. It is desirable to retain as much as possible of the filler and fiber, including fiber fines, in the sheet and it is normal to add a retention aid to the thinstock in order to promote retention.

The thinstock is usually made by diluting with water (typically whitewater from the drainage stage if paper-making) a more concentrated suspension of filler and cellulosic fiber. This more concentrated suspension is normally called the thickstock. The thickstock may be made by blending together the desired amounts of fiber, filler and water. Typically, the thickstock suspension comprises about 2.5% to about 20% by weight of calcium carbonate and cellulosic fiber in a dry weight ratio of about 10:1 to about 1:50. Typically, the thinstock is formed in an amount of about 0.02% to about 2% dry weight based on the dry weight of the suspension.

Some of the feed to the thickstock can be recycled material, for instance deinked pulp, and if the recycled pulp contains filler this previously used filler will be incorporated into the thickstock. Often additional, previously unused, filler is incorporated into the thickstock or thinstock.

Polymers of a wide range of molecular weights can be used as retention aids, and it is also known to add a high weight polymeric retention aid to the thinstock after incorporating a lower molecular weight polymeric coagulant into the thinstock or even the thickstock.

For instance it is known to treat unused filler with polymeric coagulant before adding that filler to the thickstock. The purpose of this coagulant addition is to coagulate the filler and thereby improve its retention. Unfortunately the process tends to result in the filler being less satisfactory (e.g. it gives less opacification to the paper) and so the addition of coagulant in this manner is not entirely satisfactory.

In many processes for making filled paper, a cationic, high weight, retention aid is added to the thinstock formed from good quality pulp (of low cationic demand). In such processes, the addition of retention aid usually results in improved retention of both filler and fines.

In order to improve filler and fines retention in papermaking processes to improve the yield on the starting materials and also to reduce the volume of the waste stream from paper-making, one or more calcium carbonate-binding peptide reagents as described herein may be added to the thickstock. Suitable calcium carbonate-binding peptides for this use include, but are not limited to, those having the general structure:

wherein the calcium carbonate-binding domain is specific for the calcium carbonate employed in the process. The calcium carbonate-binding peptide reagent may be added to the thickstock at a concentration of about 0.001% to about 5% dry weight based on the dry weight of the suspension. The calcium carbonate-binding peptide reagent may also be added to the diluted thinstock, to the whitewater utilized in the dilution of the thickstock to thinstock, to the calcium carbonate before addition of the calcium carbonate to the thickstock, or any combination thereof.

In papermaking, it is often desirable to coat one or both surfaces of the paper or paperboard to impart desirable properties to that surface. The coating process can improve one or more of the properties such as gloss, opacity, color, barrier properties, ink reception, hand, or density. Generally, polymeric or surfactant compounds are added to a calcium carbonate or other particulate material in the formulation of the coating suspension. In this embodiment, peptide reagents such as those having the structures:

wherein the TBD is specific to cellulose and the CCBD is specific to the particular calcium carbonate being used may be employed to promote adhesion of the particulate calcium carbonate materials to the cellulose of the paper. Subsequent to the process of making the paper and the coating suspension, the coating process includes the actual coating, drying and calendering.

In papermaking, the finishing operation may be a calendering process, in which a paper web is passed between the nips formed between one or more pairs of rolls and the surface of the web is thereby flattened to form a smooth surface. Simultaneously, the thickness, or caliper, of the paper web is reduced and the web is densified.

Calendering generally reduces caliper, and, as a result, a higher density is obtained in the finished paper product. Bulk is inversely related to density, therefore when the density is increased, the bulk of finished paper product will be reduced. Calendering may generally be accomplished using a gloss calender, a soft calender or a supercalender.

The gloss calender is typically comprised of a hard, non-resilient, heated roll made, for example, of steel, positioned proximally to a soft roll so as to form a narrow gap or nip. As the web passes through the nip it is exposed to a nip load in the range of from about 100 to about 900 pounds per lineal inch (pli). Nip pressures in this type of device are usually in the range of less than about 2000 pounds per square inch (psi). A wide range of processing temperatures can be used in a gloss calender, with the typical maximum temperature being in the range of about 200° C. The finishing effect achieved using the gloss calender, however, is not as smooth or as flat, and therefore not as glossy, as the surface produced using an apparatus capable applying higher pressure.

It is therefore often useful to increase the nip load or the roll temperature, or both, to plasticize and smooth the surface layers of the paper. Such modifications are incorporated, for example, in the design and operation of the conventional soft calender. The soft calender is usually constructed as having one to two nips per coated side, or as a two- or four-nip device, with each nip being formed between a heated hard roll and an unheated soft roll.

Alternatively, supercalendering may be used as the finishing operation. In such a process, the web is sequentially passed between a series of nips formed between the vertically stacked rolls of a supercalender. The supercalender typically comprises a frame having an upper roll and a lower roll between which are positioned intermediate rolls. The rolls of the supercalender may be heated hard rolls or unheated soft rolls, in serial or alternating arrangement. As the web is passed through each nip, the web is compacted to form paper of substantially uniform density and high gloss by virtue of the repeated pressurization and heat exposure. In a supercalender, the nips are loaded initially by gravity, i.e., gravitational forces acting on the weight of the rolls themselves produce a distribution of the weight from the upper nip to the bottom nip that is substantially linear and increasing. This has the consequence that the load present in the bottom nip actually determines the loading capacity of the calender stack.

As used herein, "paper product" includes all varieties of finished paper or paperboard materials. The term "high gloss" means a TAPPI gloss value of greater than 60, as determined at a 75° angle of reflectance.

In one embodiment disclosed herein, a coating formulation is applied to the surface of a base stock before finishing. The "base stock" may be a dried web or sheet or material otherwise formed from a paper furnish comprised of wood pulp and, optionally, other additives. Preferably, the pulp is a comprised mainly of chemical pulp, but the furnish may contain, if desirable, other types of pulp including mechanical pulp, semi-chemical pulp, recycled pulp, pulp containing other natural fibers, synthetic fibers, and any combination thereof. The base stock may be of any suitable fiber composition having a uniform dispersion of cellulosic fibers alone or in combination with other fiber materials, such as natural or synthetic fiber materials. Examples of suitable substrates include previously coated or uncoated paper or paperboard stock.

The coating formulation comprises a solid particulate pigment in a suitable solvent, and in the case of this disclosure the particulate pigment is a calcium carbonate or a pigment coated with a calcium carbonate. Suitable solvents include water, and mixtures of water with water-miscible organic solvents, such as glycols and alcohols. The coating formulation further comprises one or more peptide reagents, including but not limited to, those having the structures:

(wherein the TBD is specific to cellulose and the CCBD is specific to the particular calcium carbonate being used. The peptide reagent is employed to promote adhesion of the particulate calcium carbonate materials to the cellulose of the paper. The brightness of the calcium carbonate may be selected based on the brightness requirement for the finished product, and accordingly, high or regular brightness calcium carbonate may be used. Examples of high brightness calcium carbonates are Carbital 90® GCC or OPTI-CAL HP® PCC, while a regular brightness material is G400®, all available from Imrys. Preferably, regular or high brightness calcium carbonate is used. The amount of calcium carbonate added to the coating formulation may be up to about 90 parts by weight based on the total weight of the dry pigment. Other conventional additives, such as binders, opacifiers, whitening agents, pigments, starch, polyvinyl alcohol may be added to improve various properties of the coating process or the final coated paper product.

In one embodiment, a base stock is formed and at least one side of the base stock is coated with the coating formulation described above, which comprises a calcium carbonate-binding peptide reagent. The base stock may be coated using methods known in the art, such as applying the coating with a jet applicator blade metering coater, a film coater, or a combination of these coating methods to obtain multiple layer coatings. The coated base stock is then passed through a calendering device, as described above, to form the calcium carbonate-coated paper or paperboard.

In one embodiment, the CCBD is specific to the particular calcium carbonate being employed and the TBD is specific to cellulose.

In another embodiment, CCBD is specific to the particular calcium carbonate being employed and the TBD is specific to an ink pigment.

Preparation of Precipitated Calcium Carbonate (PCC) Slurries

The calcium carbonate-binding peptide reagents disclosed herein may also be used in the preparation of a precipitated calcium carbonate (PCC) slurry. As generally appreciated in typical PCC forming chemistry, burnt lime (calcium oxide) first is slaked by the addition of water to form an aqueous slurry of calcium hydroxide. The lime is fed into a slaker fitted with a coarse screen at its outlet to form an aqueous suspension of calcium hydroxide, i.e., milk of lime ("MOL") or lime milk for short.

Calcium carbonate is commonly precipitated in the form of calcite, aragonite, or vaterite crystalline forms. This morphology can be controlled partially by the operating condition as well known to those skilled in the art, but may be further controlled by adding to the aqueous suspension of lime milk, one or more calcium carbonate-binding peptide reagents as described herein, which is designed to control the crystallization process by binding selectively to particular crystallographic faces of the available mineral forms. Calcium carbonate-binding peptide domains that bind selectively to a single crystallographic face of calcium carbonate crystals may be identified using the methods described above. Suitable peptide reagents for this use include, but are not limited to, those having the general structure:

wherein the TBD has high affinity for one or more of the following: acrylics or urethanes for use in automotive finishes or other paint products; natural or synthetic rubbers for use in rubber products; silicone materials for use in sealant products; any of the functional ingredients selected from chelating agents, colorants, dispersants, emollients, emulsifiers, fragrances, humectants, opacifying agents, preservatives, skin conditioners, or thickeners for use in cosmetics; a polymer, including, nylons, polyesters, polycarbonates, acrylics, polyolefins, fluoropolymers or polyvinylchloride; or cellulose or ligno-cellulosic materials.

Calcite crystals are typically either rhombohedral, prismatic or scalenohedral in shape, while the aragonite crystal form is acicular or needle shaped. The PCC crystals may be aggregated into larger particles or be essentially non-aggregated depending on the precipitation reaction conditions and mechanical post-processing of the PCC particles. In this disclosure, calcite type crystals are preferred, and especially rhombohedral shapes, although the invention is not limited thereto and may also involve the production of scalenohedral shapes of calcite, or aragonite crystals of PCC. In general, the use of rhombohedral character crystal structures of PCC is often favored for paper coating applications since the aqueous PCC slurries prepared according to this disclosure may have very good rheological and stability properties.

In one embodiment, the calcium carbonate-binding peptide domain of the peptide reagent used in the process is selective to the crystal faces of aragonite crystals.

In another embodiment, the calcium carbonate-binding peptide domain of the peptide reagent used in the process is selective to the crystal faces of calcite crystals.

The aqueous suspension of lime milk containing the peptide reagent is then carbonated by exposure to carbon dioxide under high shear conditions to precipitate calcium carbonate at approximately 15-25% solids. The cabonating step may comprise two phases, a seed phase and a growth phase. In the seed phase, the temperature of the lime milk slurry is adjusted to a suitable value, typically about 50° C. The slurry is vigorously agitated and carbon dioxide gas, typically mixed with air, is introduced until the reaction is substantially complete. In the growth phase, additional amounts of lime milk are added while agitating the seed and introducing carbon dioxide gas. The lime milk and carbon dioxide gas are added continuously at a controlled rate until the desired amount of lime milk has been added and the desired amount of the seeding material has been produced.

Optionally, the precipitated calcium carbonate slurry may be further processed in a number of ways. For example, the precipitated calcium carbonate slurry may be withdrawn from the carbonation reactor and fed through a fine screen. Dewatering may be performed in a decanter, such as a wet centrifugal classifier, or alternatively with a vacuum filter or other conventional dehydrating machine used for this purpose, to provide a partially dewatered PCC slurry having a higher solids content than the PCC slurry produced by the method described above (i.e., typically about a 50 wt % PCC slurry). An organic dispersant may be added to the resulting partially dewatered PCC slurry to produce a dispersed, partially dewatered PCC slurry having a shear viscosity.

The organic dispersant may be selected from the organic dispersants and dispersing aids generally known in the art for the dispersion of calcium carbonate. The dispersant may comprise for example a polycarboxylate which may be homopolymers or copolymers that contain monomer units comprising a vinyl or olefinic group, or a water soluble thereof (e.g., sodium polyacrylate). Examples of suitable monomers include acrylic acid, methacrylic acid, itaconic acid, maleic acid, fumaric acid, crotonic acid, maleic anhydride, hydroxyacrylic acid, and the like. The dispersant can be a sodium polyacrylate, such as commercially available as COLLOID 211® manufactured by Vinings Industries Inc. of Marietta, Ga., or ACUMER 9300® manufactured by Rohm & Haas, Philadelphia Pa., or DISPEX 2695® dispersant available from Allied Colloids, Suffolk, Va.

One or more peptide reagents, such as those described above for use in the preparation of the PCC slurry, may also be used as the organic dispersant, either alone or in combination with a standard organic dispersant. The dispersed, partially dewatered PCC slurry may be subjected to fluid shear forces to reduce the shear viscosity. Additionally, any of the PCC slurries described above may be processed by wet grinding in a plurality of steps to produce a ground slurry. The ground slurry may be further processed by adding an organic dispersant, such as those described above.

The PCCs prepared by the process described may be especially suitable for use as coating pigments in paper coating compositions. When used in that manner, the PCC slurry is used together with a binder, such as any known paper coating binders, including, but not limited to, latexes, proteins, starches, casein, acrylic polymers, and styrene butadiene rubbers. Additionally, the calcium carbonate-binding peptide domain may be included in a peptide reagent that is further designed to selectively bind to cellulosics materials, obviating the need for additional binders. The binder, peptide, or combination thereof may be used in an amount of generally between about 1 to 20 parts by weight as based on the total dry weight of all pigments present in the coating. The pigment slurry contains at least 65 wt % PCC, as indicated above, and more preferably between 70-80 wt % PCC before addition of the binder and other optional paper coating ingredients described herein. Optional paper coating ingredients include a thickener, e.g., sodium carboxymethyl cellulose or synthetic acrylic thickeners known in the paper coating field. The thickener, if used, is added in an amount of no more than about 2 parts by weight as based on the total dry weight of all pigments present. Also, other pigments besides PCC, such as kaolin clay, ground calcium carbonate, titanium dioxide, zirconium orthosilicate, calcined clay, talc, calcium sulfate, and the like, may be used in combination with the PCC in the paper coating composition. It may be advantageous to have the calcium carbonate-binding domain incorporated into a peptide which has further specific binding affinity for any of these materials. These other pigments can be used in amounts of about 20 to 80 wt % based on the total weight of dry pigment in the coating.

Additionally, the PPCs prepared according to the method described above may be incorporated into polyvinylchloride and other polymer products as a filler, using methods known in the art.

Personal Care Compositions

Compositions for use in personal care include cosmetic applications including, but not limited to blush, bronzers, concealers, foundations, makeup primers, mascaras, powders, shimmers, paste masks, cleansing preparations, and eyeliners comprising a calcium carbonate mineral treated with a suitable calcium carbonate-binding peptide including, but not limited to, those having the general structure:

In this embodiment, the TBD has a high affinity for a variety of functional ingredients including, but not limited to, chelating agents, colorants, dispersants, emollients, emulsifiers, fragrances, humectants, opacifying agents, preservatives, skin conditioners, or thickener. Similarly, personal care compositions may comprise a calcium carbonate mineral treated with one or more calcium carbonate-binding peptide reagents such as those having the general structure:

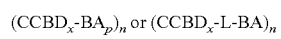

wherein the benefit agent is covalently linked, either directly or through a linking molecule, to the calcium carbonate-binding peptide domain. In the two examples above, the calcium carbonate may also serve the function of a chelating agent.

As described above, calcium carbonate-binding peptides such as those having the general structure:

wherein the TBD has affinity for a body surface, such as skin, hair, nails, and the like, may be used in various personal care compositions to color body surfaces. In this embodiment, either the natural color of the calcium carbonate or a colored calcium carbonate is used. Additionally, these peptides may be used to deliver the calcium carbonate, which serves as a conditioning agent, to a body surface.

A number of the embodiments described herein may be used in hair care compositions. Hair care compositions are herein defined as compositions for the treatment of hair, including but not limited to shampoos, conditioners, lotions, aerosols, gels, mousses, and hair dyes. If the calcium carbonate-binding peptides are desired to be used in connection with a hair care composition, an effective amount of the peptide reagent for use in a hair care composition is herein defined as a proportion of from about 0.01% to about 10%, preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hare care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments.

A number of embodiments disclosed herein may be used in a skin care composition. Skin care compositions are herein defined as compositions comprising an effective amount of a skin conditioner or a mixture of different skin conditioners in a cosmetically acceptable medium. The uses of these compositions include, but are not limited to, skin care, skin cleansing, make-up, and anti-wrinkle products. If it is desired to use the methods or materials disclosed herein in connection with a skin care composition an effective amount of the peptide reagent for skin care compositions is herein defined as a proportion of from about 0.001% to about 10%, preferably about 0.01% to about 5% by weight relative to the total weight of the composition. This proportion may vary as a function of the type of skin care composition. Suitable compositions for a cosmetically acceptable medium are described by Philippe et al. supra. For example, the cosmetically acceptable medium may be an anhydrous composition containing a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Printing Applications

One application of the peptide reagents described herein is in aqueous inks, such as ink jet inks. These inks may be used to print onto a calcium carbonate-coated paper. In this embodiment, the peptide reagent comprises a calcium carbonate-binding domain coupled to a pigment or a calcium carbonate-binding domain and a pigment-binding domain. In either case, the calcium carbonate-binding domain binds to a calcium carbonate-coated paper surface, thereby attaching the pigment to the paper.

Aqueous ink formulations are well known in the art. For example suitable formulations are described by Ma et al. in U.S. Pat. No. 5,272,201 and by Ma et al. in U.S. Pat. No. 5,085,698, both of which are incorporated herein by reference. Aqueous ink formulations typically comprise an aqueous carrier medium, a pigment or a mixture of pigments, a dispersant, and various other ingredients.

The aqueous carrier medium comprises water or a mixture of water and at least one water-soluble organic solvent. Deionized water is commonly used. Representative examples of water-soluble organic solvents are disclosed by Ma et al. in U.S. Pat. No. 5,085,698. The selection of a suitable mixture of water and water-soluble organic solvent depends upon the requirements of the specific application, such as the desired surface tension and viscosity, the selected pigment, drying time of the ink, and the type of media substrate onto which the ink will be printed. A mixture of a water-soluble polyhydric alcohol having at least 2 hydroxyl groups, e.g., diethylene glycol, and deionized water is preferred as the aqueous carrier medium, with water comprising between about 30% and about 95%, preferably about 60% to about 95%, by weight, based on the total weight of the aqueous carrier medium. The amount of aqueous carrier medium is in the range of about 70% to about 99.8%, preferably about 94% to about 99.8%, based on total weight of the ink when an organic pigment is selected, and about 25% to about 99.8%, preferably about 70 to about 99.8% when an inorganic pigment is selected.

The pigment may be a single pigment or a mixture of pigments. Suitable pigments for printing applications are described above. The ink may contain up to about 30% pigment by weight, preferably the amount of pigment is between about 0.1% to about 15% by weight.

The peptide reagents described herein may be used alone or in combination in the ink formulation. The peptide reagent is present in the ink composition in the range of about 0.1% to about 30% by weight.

The peptide reagent may serve as a dispersant for the pigment, or conventional dispersants or self-dispersing pigments may be used. When a dispersant is used to disperse the pigment, the dispersant may be any suitable dispersant known in the art, including, but not limited to, random or structured organic polymeric dispersants, as described below; protein dispersants, such as those described by Brueckmann et al. (U.S. Pat. No. 5,124,438); and peptide-based dispersants, such as those described by O'Brien et al (co-ending and commonly owned U.S. Patent Application Publication No. 2005/0054752). Preferred random organic polymeric dispersants include acrylic polymer and styrene-acrylic polymers. Most preferred are structured dispersants, which include AB, BAB and ABC block copolymers, branched polymers and graft polymers. Preferably the organic polymers comprise monomer units selected from the group consisting of acrylate, methacrylate, butyl methacrylate, 2-ethylhexyl methacrylate, benzylmethacrylate, phenoxyethyl acrylate, and ethoxytriethyleneglycolmethacrylate, such as those described by Nigan (U.S. Patent Application Publication No. 2004/0232377). Some useful structured polymer dispersants are disclosed in U.S. Pat. No. 5,085,698, EP-A-0556649 and U.S. Pat. No. 5,231,131 (the disclosures of which are incorporated herein by reference). Additionally, pigments may be dispersed using a surface active agent comprising lignin sulfonic acids and a polypeptide, as described by Cioca et al. in U.S. Pat. No. 4,494,994, which is incorporated herein by reference.

A self-dispersing pigment is a pigment that has been surface modified with chemically attached, dispersibility imparting groups to allow stable dispersion without a separate dispersant. For dispersion in an aqueous carrier medium, surface modification involves addition of hydrophilic groups and most typically ionizable hydrophilic groups. The self-dispersing pigment may be prepared by grafting a functional group or a molecule containing a functional group onto the surface of the pigment, by physical treatment (such as vacuum plasma), or by chemical treatment (for example, oxidation with ozone, hypochlorous acid or the like). A single type or a plurality of types of hydrophilic functional groups may be bonded to one pigment particle. Self-dispersing pigments are described, for example, in U.S. Pat. Nos. 5,571,311, 5,609,671, 5,968,243, 5,928,419, 6,323,257, 5,554,739, 5,672,198, 5,698,016, 5,718,746, 5,749,950, 5,803,959, 5,837,045 5,846,307, 5,895,522, 5,922,118, 6,123,759, 6,221,142, 6,221,143, 6,281,267, 6,329,446, 6,332,919, 6,375,317, 6,287,374, 6,398,858, 6,402,825, 6,468,342, 6,503,311, 6,506,245, and 6,852,156The disclosures of the preceding references are incorporated herein by reference.

Consistent with the requirements for the particular application, various types of aqueous additives can be used to modify the properties of the ink composition. Surfactant compounds may be used in addition to the peptide reagents described herein. These may be anionic, cationic, nonionic, or amphoteric surfactants. It is known in the art that certain surfactants may be incompatible with certain ink compositions and may destabilize the pigment dispersion. The choice of a specific surfactant is also highly dependent on the type of print medium substrate to be printed. It is expected that one skilled in the art can select the appropriate surfactant for the specific substrate to be used in the particular ink composition. In aqueous inks, the surfactants may be present in the amount of about 0.01% to about 5% and preferably about 0.2% to about 2%, based on the total weight of the ink. Co-solvents to improve penetration and pluggage inhibition properties of the ink composition may also be added, and in fact are preferred. Such co-solvents are well known in the prior art. Additionally, biocides may be used in the ink compositions to inhibit growth of microorganisms. Sequestering agents such as ethylenediaminetetraacetic acid (EDTA) may also be included to eliminate deleterious effects of heavy metal impurities. Other known additives, such as humectants, viscosity modifiers and other acrylic or non-acrylic polymers may also be added to improve various properties of the ink compositions as desired.

The ink compositions described herein may be prepared in the same manner as other aqueous ink compositions, such as described by Ma et al. in U.S. Pat. No. 5,272,201.

The ink compositions may be applied to a calcium carbonate-coated paper using methods well known in the art, such as ink jet printing, screen printing, or gravure roll printing.

Additionally, new pigment compounds, coating compounds and methods for making the new compounds, such as coatings for ink jet receiving materials are facilitated by the use of peptide-modified calcium carbonate materials. The coated ink jet receiving material can provide improved printability, water fastness and reduced spreading. In one embodiment, the print medium is coated with one or more suitable calcium carbonate-binding peptides including, but not limited to those having the general structure:

$(CCBD_x\text{-}TBD_y)_n$ or $[(CCBD_x\text{-}L_s)_q\text{-}(TBD_y\text{-}L_t)_r]_n$ wherein the calcium carbonate-binding domain has affinity for a calcium carbonate coating on the print medium and the TBD has affinity for the pigment used in the ink formulation. Then, the print medium is used as a receiving material for the application of the ink.

Additional Applications of Calcium Carbonate-Binding Peptides

Calcium carbonates treated with peptides comprising binding domains specific for the binding of calcium carbonates and target binding domains having affinity for other materials may find utility in a variety of other applications. These applications are detailed in the following paragraphs.

Primary or sedimentary calcium carbonate may be purified by providing a dispersed aqueous suspension containing the calcium carbonate particulate material and having at least one selective flocculation polymer having two CCBDs at opposite ends of a long tether. The impurities removed by the process include titania, anatase, smectite, iron oxide, and mica.

Calcium carbonates modified with calcium carbonate-binding peptides may find use in pharmaceutical applications as an adsorbent, suspending agent, tablet disintegrant and tablet/capsule diluent, or in oily suspension filled capsules to reduce the sedimentation rate of the incorporated powders. Modified calcium carbonates may also be employed in nutraceutical applications to prevent the alteration of the absorption of orally administered drugs such as amoxicillin, ampicillin, cimetidine, digoxin, lincomycin, phenyloin, and tetracycline There are a wide variety of applications for the peptide-modified calcium carbonates in agrochemical and agricultural applications. The calcium carbonates may be coated on seeds to provide a number of beneficial effects during planting. The calcium carbonates can be modified to provide timed release of insecticides. The modified calcium carbonates can be modified to act as simple carriers of insecticides and pesticides. The calcium carbonates may also be modified to selectively bind to chitin so that they selectively bind to insects in close proximity to the seeds. Calcium carbonates can also be modified to act as carriers of fungicides and biocides or humidity-controlled release of fertilizers and/or herbicides, fungicides or insecticides.

As mined materials, calcium carbonates show considerable variation from mine to mine and even from different locations within a single mine. These variations include the associated impurities that may be removed by selective complexation with peptides. This is particularly important in food and medicinal grades of calcium carbonates. This will certainly include the refining of the calcium carbonates to remove harmful materials as described above. It can also include the incorporation of benefit agents that simply make the calcium carbonate materials more palatable or add flavorants, etc. It can also include means of binding the calcium carbonates to other foods such as soy protein to improve texture, processability, appearance, and marketability. The modified calcium carbonates may also be useful as bonding agents in animal feeds designed to carry selected benefit agents.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The methods or materials described herein are further defined in the following Examples. It should be understood that these Examples, while indicating preferred embodiments disclosed herein, are given by way of illustration only. From the above discussion and these Examples, one skilled in the art can ascertain the essential characteristics of methods or materials described herein, and without departing from the spirit and scope thereof, can make various changes and modifications disclosed herein to adapt it to various uses and conditions.

The meaning of abbreviations used is as follows: "min" means minute(s), "sec" means second(s), "h" means hour(s), "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "g" means the gravitation constant, "rpm" means revolutions per minute, "pfu" means plaque forming unit, "BSA" means bovine serum albumin, "PEG" means polyethylene glycol, "ELISA" means enzyme linked immunosorbent assay, "IPTG" means isopropyl β-D-thiogalacto-pyranoside, "A" means absorbance, "$A_{450}$" means the absorbance measured at a wavelength of 450 nm, "TBS" means Tris-buffered saline, "TBST-X" means Tris-buffered saline containing TWEEN® 20 where "X" is the weight percent of TWEEN® 20, "Xgal" means 5-bromo-4-chloro-3-indolyl-beta-D-galactopyranoside, "SEM" means standard error of the mean, "vol %" means volume percent, and "mS" means millisiemens.

General Methods:

Standard recombinant DNA and molecular cloning techniques used in the Examples are well known in the art and are described by Sambrook, J., and Russell, D., *Molecular Cloning: A Laboratory Manual*, 3$^{rd}$ Ed. Cold Spring Harbor Laboratory Press, Cold Spring Harbor, N.Y., 2001, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Prophetic

Selection of Calcium Carbonate-Binding Peptides Using Phage Display Biopanning

The purpose of this prophetic Example is to describe how to identify phage peptides that bind to calcium carbonate using a modified phage display biopanning method.

Phage Display Peptide Libraries:

The phage libraries described herein, Ph.D.-12™ Phage Display Peptide Library Kit and Ph.D.-7™ Phage Display Library Kit, are purchased from New England BioLabs (Beverly, Mass.). These kits are based on a combinatorial library of random peptide 7 or 12-mers fused to a minor coat protein (pIII) of M13 phage. The displayed peptide is expressed at the N-terminus of pIII, such that after the signal peptide is cleaved, the first residue of the coat protein is the first residue of the displayed peptide. The Ph.D.-7 and Ph.D.-12 libraries consist of approximately $2.8 \times 10^9$ and $2.7 \times 10^9$ sequences, respectively. A volume of 10 μL contains about 55 copies of each peptide sequence. Each initial round of experiments is carried out using the original library provided by the manufacturer in order to avoid introducing any bias into the results.

Biopanning Against a Calcium Carbonate Surface:

The calcium carbonate sample is OPTI-CAL 400 PCC, available from Imerys (Roswell, Ga.). The following protocol is used for biopanning against the calcium carbonate particles. The calcium carbonate particles are suspended in a tube filled with 5 mL of 90% isopropanol for 30 min at room temperature and then washed 5 times for 10 min each with deionized water before being collected by vacuum filtration. Then, 5 mL of blocking buffer consisting of 1 mg/mL BSA in TBST containing 0.5% TWEEN® 20 (TBST-0.5%) is added to the tube and incubated for 1 h at 4° C.

The calcium carbonate particles are filtered and washed 5 times with TBST-0.5% and then 2 mL of TBST-0.5% containing 1 mg/mL BSA is added to the tube. Then, 10 μL of the original phage library ($2 \times 10^{11}$ pfu), either the 12-mer or 7-mer library, is added to the calcium carbonate particles and incubated for 15 min at room temperature. The calcium carbonate particles are filtered and washed 10 times with TBST-0.5%. The calcium carbonate is then transferred to a clean tube, 2 mL of a non-specific elution buffer consisting of 1 mg/mL BSA in 0.2 M glycine-HCl, pH 2.2, is added to the tube and incubated for 10 min. The calcium carbonate particles are filtered and washed three more times with the elution buffer and then washed three times with TBST-0.5%. The calcium carbonate, which has acid resistant phage peptides still attached, is used to directly infect the host cells *E. coli* ER 2738 (New England BioLabs, Beverly, Mass.), for phage amplifications. The calcium carbonate is incubated with an overnight *E. coli* ER2738 culture diluted 1:100 in LB medium, at 37° C. for 4.5 h. After this time, the cell culture is centrifuged for 30 s and the upper 80% of the supernatant is transferred to a fresh tube, 1/6 volume of PEG/NaCl (20% polyethylene glycol-800, obtained from Sigma Chemical Co. St. Louis, Mo., 2.5 M sodium chloride) is added, and the phage is allowed to precipitate overnight at 4° C. The precipitate is collected by centrifugation at 10,000×g at 4° C. and the resulting pellet is resuspended in 1 mL of TBS. This is the first round of amplified stock. The amplified first round phage stock is then titered according to the method described below. For the next round of biopanning, more than $2 \times 10^{11}$ pfu of phage stock from the first round is used. The biopanning process is repeated for 3 to 4 rounds depending on the experiments.

After the acid wash steps in the final round of biopanning, the calcium carbonate is used to directly infect 500 µL of mid-log phase bacterial host cells, *E. coli* ER2738, which are then grown in LB medium for 20 min and then mixed with 3 mL of agarose top (LB medium with 5 mM $MgCl_2$, and 0.7% agarose) at 45° C. This mixture is spread onto a LB medium/IPTG/S-Gal™ plate (LB medium with 15 g/L agar, 0.05 g/L IPTG, and 0.04 g/L S-Gal™) and incubated overnight at 37° C. The black plaques are counted to calculate the phage titer. The single black plaques are randomly picked for DNA isolation and sequencing analysis. The peptide sequences identified will have a high binding affinity for PCC. This same procedure may be used to identify peptide sequences that bind to other types of calcium carbonate minerals.

Example 2

Selection of Calcium Carbonate-Binding Peptides Using mRNA-Display Biopanning

The purpose of this Example is to describe how calcium carbonate-binding peptides were selected using an mRNA display biopanning method.

mRNA-Display Peptide Libraries:

Methods to make libraries of DNA molecules suitable as starting materials for mRNA-display are well-known in the art (see WO2005/051985). The following procedure was used to identify 27-mer peptides that have a specific affinity for a calcium carbonate target material (crushed Calcite crystal ($CaCO_3$). The calcite crystal was a clear, colorless Iceland Spar widely available in local mineral shops. It was initially cleaved into 1 mm planes using a knife and hammer. Those planes were further cleaved into small rhombohedra and the resulting material was ground in an agate mortar and pestle to the consistency of a fine white sand. Microscopic examination showed that the rhomohedra persisted down to this scale Briefly, a library of random nucleic acid molecules (ds-DNA) encoding a peptide of desired length was generated. A linear peptide library containing 27 randomized amino acid positions was used ("p27 library"). The DNA molecules were designed to include appropriate 5' and 3' regions for efficient in vitro transcription, translation, purification, and coupling to the MHA-oligonucleotide linker (MHA is 3'-[α-amino-p-methoxy-hydrocinnamido]-3'-deoxy-N,N-dimethyl-adenosine (Cosmix GmbH, Braunschweig, Germany).

The DNA encoding the linear peptide library was designed to include a T7 promoter and a tobacco mosaic virus (TMV) translation initiation sequence operably linked to the coding sequence (CDS) (Liu et al., *Methods in Enzymology*, 318: 268-293 (2000)). The CDS was designed to encode: (1) a constant N-terminal flaking region comprising a hexa-histidine tag followed by a flexible linker (italicized) sequence (MHHHHHH*SGSSSGSGSG*; SEQ ID NO: 199), (2) the randomized 27-mer linear peptide, and (3) a constant C-terminal flanking region (TSGGSSGSSLGV<u>ASAI</u>; SEQ ID NO: 200) comprising another flexible linker region (bold) and a C-terminal sequence optimized for efficient coupling to the MHA-oligonucleotide linker (underlined).

In Vitro Transcription

Double stranded DNA as result of the PCR reactions were transcribed into RNA using the RiboMax Express in vitro transcription kit (Promega Madison, Wis.). After incubation for at least 45 min at 37° C., DNase I was added and the incubation continued at 37° C. for additional 30 minutes to degrade all template DNA. The reaction mixture was purified by phenol/chloroform extraction. Then free nucleotides were removed by gel filtration using G25 microspin columns (Pharmacia; Milwaukee, Wis.). Concentration of purified RNA was determined by photometry at 260 nm.

Library Preparation:

Approximately 10 pmol of highly purified RNA was produced by in vitro transcription from the p27 DNA library and purified after DNase I digestion (by phenol/chloroform extraction and gel filtration, methods described below). The 3'-end of the p27 library RNA was modified by attachment of a MHA-linker molecule (as described below) and translated in vitro by means of a rabbit reticulocyte lysate. Covalent fusion products between peptide and coding RNA were purified on magnetic oligo(dT) beads, reverse transcribed, and again purified on a Ni-NTA purification matrix to remove uncoupled RNA and free peptides. About 8 pmol of peptide-RNA-cDNA-fusions were used as input for the first contact with target material during selection round 1.

Chemical Coupling of RNA and MHA-Oligonucleotide Linker

Purified RNA was annealed (by heat denaturation for 1 minute at 85° C. and cooling down to 25° C. for 10 minutes) with a 1.5-fold excess of MHA-oligonucleotide linker-$PEG_2A18$ (5'-psoralen-*UAG CGG AUG C*$A_{18}$ $(PEG-9)_2$ CC-MHA [nucleotides shown in italics represent 2'-O-methyl-derivatives] (SEQ ID NO: 201). The covalent coupling was induced by radiation with UV-light (365 nm) for 15 min at room temperature. Aliquots of this reaction mixture before and after irradiation with UV were analyzed on a 6%-TBE-Urea-polyacrylamidgel to control the coupling efficiency (usually at least 60%).

In Vitro Translation and $^{35}$S-Labelling of Peptide-RNA Fusions

Ligated RNA was translated using a rabbit reticulocyte lysate from Promega in presence of 15 µCi $^{35}$S-methionine (1000 Ci/mmole). After a 30 min incubation at 30° C., KCl and $MgCl_2$ were added to a final concentration of 530 mM and 150 mM respectively in order to promote formation of mRNA-peptide-fusions.

Oligo(dT) Purification

For the purification of peptide-RNA-fusions from translation mixtures molecules were hybridized to magnetic oligo (dT) beads (Miltenyi Biotec; Bergisch Gladbach, Germany) in annealing buffer (100 mM Tris-HCl pH 8.0, 10 mM EDTA, 1 M NaCl and 0.25% Triton X-100) for 5 min at 4° C. Beads were separated from the mixture using MiniMACS-filtration columns (Miltenyi Biotec), repetitively washed with 100 mM Tris-HCl pH 8.0, 1 M NaCl, 0.25% Triton X-100 and finally eluted with water. A sample of this reaction was analyzed on 4-20% Tris/glycine-SDS-PAGE; radioactive bands were visualized using a PhosphoroImager.

Reverse Transcription (RT)

The RNAs of Oligo(dT)-purified peptide-RNA-fusions were reverse transcribed using SuperScript II Reverse Transcriptase (Invitrogen, Carlsbad, Calif.) according to the manufacturers recommendations. RT reactions contained about 1.5-fold excess of 3'-ReversePrimer. A sample of this reaction was analyzed on 4-20% Tris/glycine-SDS-PAGE; radioactive bands were visualized using a Phosphorimager.

His-Tag Purification

Reverse transcribed mRNA-peptide-fusion molecules were mixed with Ni-NTA-agarose (QIAGEN; Valencia, Calif.) in HBS buffer (20 mM HEPES pH 7.0, 150 mM NaCl, 0.025% Triton X-100, 100 µg/mL sheared salmon sperm DNA, 1 mg/mL BSA) and incubated for 60 min at room temperature under gentle shaking. Ni-NTA was then filtrated and washed with HNT buffer (20 mM HEPES pH 7.0, 150 mM NaCl, 0.025% Triton X-100) containing 5 mM imidazole. Finally peptide-RNA-cDNA-fusions were eluted with 150 mM imidazole in HNT buffer (20 mM HEPES pH 7.0, 150 mM NaCl, 0.025% Triton X-100). A sample of this reaction was analyzed on 4-20% Tris/glycine-SDS-PAGE; radioactive bands were visualized using a Phosphorimager. BSA (final concentration 1 mg/mL) and shared salmon sperm DNA (final concentration 100 µg/mL) were added to the eluates before contacting with target materials during selection step.

Selection by Binding to Target Materials and Washing

A. Incubation of Peptide-RNA-cDNA-Fusion Library with Target Material:

Purified peptide-RNA-cDNA-fusions (PROFUSION™ molecules; Adnexus Therapeutics, Waltham, Mass.) after Ni-NTA purification were incubated for 60 minutes at room temperature in 1 mL (final volume) of HNTween buffer (20 mM HEPES, pH 7.4, 150 mM NaCl, 0.5% Tween-20) in the presence of 1 mg/mL BSA, 100 µg/mL shared Salmon sperm DNA and DEPC-treated, blocked target material. Input activities of purified peptide-RNA-cDNA-fusions was determined by scintillation measurement.

B. Washing:

Non-binding variants were washed away by one of the following washing procedures listed below:

Washing procedure A: used for washing the target material during selection rounds 1-4 and the control selection for round 10:
  5×5 sec. each with HNTween buffer (20 mM HEPES, pH 7.4, 150 mM NaCl, 0.5% Tween-20); 1 tube change during the last wash
  1×5 sec 150 mM NaCl (for buffer removal before elution with KOH)

Washing procedure B: used for washing the target material during selection rounds 5-10:
  2×5 sec. each with HNTween buffer (20 mM HEPES, pH 7.4, 150 mM NaCl, 0.5% Tween-20)
  1×5 min. with 1% shampoo in HNTriton buffer (20 mM HEPES, pH 7.4, 150 mM NaCl, 0.025% Triton-X100)
  1×5 sec with HNTween buffer including tube change
  1×5 min with 1% shampoo in HNTriton buffer
  3×5 sec with HNTween buffer; 1 tube change during the third wash
  1×5 sec 150 mM NaCl (for buffer removal before elution with KOH)
  During selection rounds 8-10, eluates were additionally purified by gel filtration using G25 Microspin columns in order to remove residual CaCO₃ or concomitant impurities which might influence the error rate of Taq polymerase during PCR reactions.

The shampoo used in the above washing procedures was a commercially available hair shampoo having the following composition:

| | |
|---|---|
| Water | 51% |
| Ammonium lauryl sulfate | 20% |
| Sodium lauryl ether sulfate | 15% |
| Cocamidopropyl betaine | 7% |
| Cocamide MEA | 2.5% |
| Miscellaneous minor components** | ~4.5% |

**(e.g. pH adjusters, preservatives, vitamins, chelating agents, dispersants, lubricants, fragrances, and dyes)

cDNA Elution:

cDNAs of binding variants were eluted by incubation of target material in 50 µL of 100 mM KOH at 60° C. for 30 minutes. After centrifugation, supernatant was removed from target material and transferred into a fresh tube. KOH eluates were subsequently neutralized by addition of 1 µL of 1 M Tris/HCl, pH 7.0 and 3.8 µL of 1 M HCl (per 50 µL 100 mM KOH).

Polymerase Chain Reaction (PCR):

After elution in KOH and neutralization, the recovered cDNAs were amplified by quantitative PCR with increasing numbers of amplification cycles (12, 15, 18, 21, 24 and 27 cycles). Products were subsequently analyzed by agarose gel electrophoresis over 2% agarose gels. Optimized conditions (minimal cycle number to get good enrichment of DNA of correct length) were then applied for a preparative PCR reaction and controlled again by agarose gel electrophoresis.

Analytical and preparative PCR reactions were performed in presence of 10 mM Tris-HCl (pH 8.8 at 25° C.), 50 mM KCl, 0.08% Nonidet P40, 2 mM MgCl₂, 2.5 mM dNTPs, 1 µM of each forward and reverse primer (5'-TAATACGACT-CATAGGGACAATTACTATTTACAATTACAATG-3'; SEQ ID NO: 202) and (5'-AATTAAATAGCGGATGCTACAC-CAAGACTAGAACCGCTG-3'; SEQ ID NO: 203), 1/5 volume of neutralized cDNA eluate and 0.05 U/µL Taq polymerase (Promega). Temperature program of PCR reaction is given below: Initial denaturation: 90 sec at 94° C.; cycling: 15 sec at 94° C. (denaturation), 20 sec at 60° C. (annealing), 30 sec at 72° C. (extension); post treatment: 3 min at 72° C. (post-treatment); hold at 4° C.

Enrichment of cDNA-RNA-Peptide Fusion Molecules Binding to Calcium Carbonate

Initial selection was conducted using stringent washing conditions (Washing Procedures A and B). Ten rounds of selection were conducted and the relative binding of radioactively labeled cDNA-RNA-peptide fusion molecules to the calcium carbonate target material was measured. The amount of target used per round was 3 mg (crushed Calcite crystal).

Rounds 1-4 of selection used washing procedure A. Rounds 5-10 used washing procedure B. The relative amount of enrichment (reported as percent enrichment of binding molecules relative to their respective input signals [activity of cDNA-RNA-peptide fusions before contacting with the target material]) is provided in Table 10.

TABLE 10

| Selection Round | Washing Procedure | % Enrichment of cDNA-RNA-peptide fusion molecules having an affinity for calcium carbonate |
|---|---|---|
| R1 | A | 0.124 |
| R2 | A | 0.595 |
| R3 | A | 1.373 |

TABLE 10-continued

| Selection Round | Washing Procedure | % Enrichment of cDNA-RNA-peptide fusion molecules having an affinity for calcium carbonate |
|---|---|---|
| R4 | A | 1.473 |
| R5 | B | 0.274 |
| R6 | B | 0.453 |
| R7 | B | 0.461 |
| R8 | B | 0.466 |
| R9 | B | 0.604 |
| R10[a] | B | 0.900[a] |
| R10 control | A | 3.519 |

[a] = enriched binder sequences of respective round analyzed

Sequencing of 27-mer Calcium Carbonate-Binding Peptides

The cDNA molecules from the enriched pool of calcium carbonate-binding fusion molecules were isolated and PCR amplified as described above. The sequences of the DNA molecules encoding the calcium carbonate-binding peptides were determined (~39 samples) and are provided in Tables 11, 12, and 13. Several samples were identified encoding an identical or nearly identical amino acid sequence (Tables 11 and 12).

TABLE 11

Enriched Calcium Carbonate-binding Peptides Sharing Significant Sequence/Structural Homology (Group A)

| Sample No. | Amino Acid Sequence[1] | SEQ ID NO: |
|---|---|---|
| 2, 3, 11, 12, 15, 17, 22, 23, 27, 34, 38 | RNNKGSKKVDDKRRKTVHNTKSRAKYS | 204 |
| 5 | RNNKGSKKVDDKRRKTVHNTKSRAKHS | 205 |
| 13 | RDNKGSKKVDDKRRKTVHNTKSRAKYS | 206 |
| 18 | RNNKGSKKVDDKRRKTVHSTKSRAKYS | 207 |
| 21 | RNNKGSRKVDDKRRKTVHNTKSRAKYS | 208 |
| 28 | RNNKGSKKADDKRRKTVHSTKSRAKYS | 209 |
| 29 | RNNKGSKKVDDKRRKAVHNKKSRAKYS | 210 |
| 30 | RNNKGSKKVDDKRRKTVHNTRSRAKYS | 211 |
| 37 | RNNKGSKKVDDKRRKTVHNTKSRAKFS | 212 |
| Consensus Group A | RXNKGSXKXDDKRRKXVHXXXSRAKXS | 213 |

[1] = bold indicates difference between conserved sequence SEQ ID NO: 204.

TABLE 12

Enriched Calcium Carbonate-binding Peptides Sharing Significant Sequence/Structural Homology (Group B)

| Sample No. | Amino Acid Sequence[2] | SEQ ID NO: |
|---|---|---|
| 4, 10, 25 | QRRKLRHPKEKWFGWSEKKVIKKWSRK | 214 |
| 19 | QRRKFRHPKEKWFGWSEKKVIKXNGRP | 215 |
| Consensus Group B | QRRKXRHPKEKWFGWSEKKVIKXXXRX | 216 |

[2] = bold indicates difference between sequence and conserved sequence SEQ ID NO: 214.

TABLE 13

Additional Enriched Calcium Carbonate-binding Peptides

| Sample No. | Amino Acid Sequence | SEQ ID NO: |
|---|---|---|
| 6 | HKRLVQNKPHRTRKIEGWIKHMVKRQH | 217 |
| 8 | TRGHIMRPCWIGAMKQGVKKKRTPGWR | 218 |
| 9 | WKVKRRMVTRTYEFMGKKPCMMLTKRL | 219 |
| 14 | KKSNKGHHSKAKQKRPHGGKAQNKNT | 220 |
| 16 | RAHKERFVVRQIGRSQGYKTWQCVRVA | 221 |
| 20 | SQKPKGHKVKVVVKLCKRPYWRMLNTA | 222 |
| 24 | NHGCPVNWKVXNPPRGWQRLNHCKWWN | 223 |
| 26 | RNSRHKEWRRYKRTHVHSHEFYHVECW | 224 |
| 31 | HRSEKPKNVNYKRGYWERGNQKKHGPG | 225 |
| 32 | HERTRRGKPDRQKTTHEKRRQGLWIFM | 226 |
| 33 | PWGTNKRQKHKVHEAKALKKSLWYSNS | 227 |
| 35 | RRGVVLCHTHRNKRIRLAYSVTKKAWA | 228 |
| 36 | ERIRWRRLSAEIRAHKWSVLKFRLSCM | 229 |
| 39 | KTKEKKKEVKLHKKSLSLVLLADLWRL | 230 |
| 40 | LGKKHKQHSKVGHGKLSTRFLRRSKLF | 231 |

Example 3

Prophetic

Characterization of Calcium Carbonate-Binding Peptide Clones by ELISA

The purpose of this prophetic Example is to describe how to evaluate the calcium carbonate binding affinity of the selected peptide clones identified by the methods described in Example 1 or Example 2 using enzyme-linked immunosorbent assay (ELISA).

Compressed pellets of the crushed Iceland Spar calcium carbonate sample are placed in a 96-well apparatus, a Minifold I Dot-Blot System from Schleicher & Schuell, Inc. (Keene, N.H.) and are used as the target. For each clone to be tested, the well is incubated for 1 h at room temperature with 200 μL of blocking buffer, consisting of 2% non-fat dry milk in TBS. The blocking buffer is removed by inverting the systems and blotting them dry with paper towels. The wells are rinsed 6 times with wash buffer consisting of TBST-0.5%.

The wells are filled with 200 μL of TBST-0.5% containing 1 mg/mL BSA and then 10 μL (over $10^{12}$ copies) of purified phage stock are added to each well. A skin-binding phage clone (skin-1) having a skin-binding peptide sequence given as SEQ ID NO:81, serves as the control. The samples are incubated at 37° C. for 15 min with slow shaking. The non-binding peptides are removed by washing the wells 10 to 20 times with TBST-0.5%. Then, 100 μL of horseradish peroxidase/anti-M13 antibody conjugate (Amersham USA, Piscataway, N.J.), diluted 1:500 in the blocking buffer, is added to each well and incubated for 1 h at room temperature. The conjugate solution is removed and the wells are washed 6 times with TBST-0.05%. TMB substrate (200 μL), obtained from Pierce Biotechnology (Rockford, Ill.) is added to each well and the color is allowed to develop for between 5 to 30 min, typically for 10 min, at room temperature. Then, stop solution (200 μL of 2 M $H_2SO_4$) is added to each well and the solution is transferred to a 96-well plate and the $A_{450}$ is measured using a microplate spectrophotometer (Molecular Devices, Sunnyvale, Calif.).

The results will demonstrate that all of the calcium carbonate-binding peptides tested have a significantly higher binding affinity for calcium carbonate than the control skin-1 peptide.

Example 4

Prophetic

Determination of the Calcium Carbonate-Binding Affinity of Calcium Carbonate-Binding Peptides The purpose of this prophetic Example is to describe how to determine the affinity of the calcium carbonate-binding peptides for calcium carbonate surfaces, measured as $MB_{50}$ values, using an ELISA assay. The term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with the calcium carbonate substrate.

A calcium carbonate-binding peptide, identified using the method described in Example 1 or Example 2, is synthesized by Synpep Inc. (Dublin, Calif.). The peptide is biotinylated by adding a biotinylated lysine residue at the C-terminus of the amino acid binding sequence for detection purposes and an amidated cysteine is added to the C-terminus of the sequence.

$MB_{50}$ Measurement of Calcium Carbonate-Binding Peptide:

The $MB_{50}$ measurements of biotinylated peptide binding to calcium carbonate are done using the 96-well plate format. Compressed pellets of the crushed Iceland Spar calcium carbonate sample are added to the wells. The wells containing the calcium carbonate samples are blocked with blocking buffer (SUPERBLOCK™ from Pierce Chemical Co., Rockford, Ill.) at room temperature for 1 h, followed by six washes with TBST-0.5%, 2 min each, at room temperature. Various concentrations of biotinylated, binding peptide are added to each well, incubated for 15 min at 37° C., and washed six times with TBST-0.5%, 2 min each, at room temperature. Then, streptavidin-horseradish peroxidase (HRP) conjugate (Pierce Chemical Co., Rockford, Ill.) is added to each well (1.0 μg per well), and incubated for 1 h at room temperature. After the incubation, the wells are washed six times with TBST-0.5%, 2 min each at room temperature. Finally, the color development and the absorbance measurements are performed as described in Example 3.

The results are plotted as $A_{450}$ versus the concentration of peptide using GraphPad Prism 4.0 (GraphPad Software, Inc., San Diego, Calif.). The $MB_{50}$ values are calculated from Scatchard plots. The results will demonstrate that the calcium carbonate-binding peptide has a high affinity for PCC, as indicated by a low $MB_{50}$ value (i.e., less than about $1 \times 10^{-4}$ M).

Example 5

Prophetic

Selection of Calcite-Binding Peptides Selective for a Single Crystallographic Face Using Biopanning The purpose of this prophetic Example is to describe how to identify peptides that bind to a specific face of a calcium carbonate mineral using a modified phage display biopanning method.

Biopanning Against a Calcite Surface:

The phage display libraries described in Example 1 are used in a modified biopanning process. The calcium carbonate substrate used is a natural, museum-quality single crystal of the trigonal scalenohedral (dog-tooth) form of calcite features adjacent crystal faces having enantiomorphic surface structures based upon the [21$\bar{3}$1] crystallographic faces. The markedly acentric surface structures of both the (3$\bar{1}$21) face (B) and the (21$\bar{3}$1) face (C) consist of corner-linked chains of $CaO_6$ octahedra, cross-linked by planar $CO_3$ groups, which are seen almost on edge. As described below, it is expected that one set of peptides will bind preferentially on the (3$\bar{1}$21) face, whereas others will bind preferentially on the (21$\bar{3}$1) face.

The following protocol is used for biopanning against the particular faces selectively. The single crystal is suspended in a tube filled with 5 mL of 90% isopropanol for 30 min at room temperature and then washed 5 times for 10 min each with deionized water. Then all but one of the faces of the crystal (the [21$\bar{3}$1] crystallographic face) are masked using a (perfluorohexyl)ethyl methacrylate polymer to make the surface hydrophobic. The remainder of the procedure is carried out on that one unmasked face.

First, 5 mL of blocking buffer consisting of 1 mg/mL BSA in TBST containing 0.5% Tween® 20 (TBST-0.5%) is added to a tube in which the crystal is immersed and the system incubated for 1 h at 4° C. The crystal is removed and is washed 5 times with TBST-0.5% and then 2 mL of TBST-0.5% containing 1 mg/mL BSA is added to the tube. Then, 10 μL of the original phage library ($2 \times 10^{11}$ pfu), either the 12-mer or 7-mer library, is added to the system and incubated for 15 min at room temperature. The crystal is removed and washed 10 times with TBST-0.5%. The crystal is then transferred to a clean tube, 2 mL of a non-specific elution buffer consisting of 1 mg/mL BSA in 0.2 M glycine-HCl, pH 2.2, is added to the tube and incubated for 10 min. The crystal is removed and washed three more times with the elution buffer and then washed three times with TBST-0.5%. The crystal, which has acid resistant phage peptides still attached, is used to directly infect the host cells *E. coli* ER 2738 (New England BioLabs, Beverly, Mass.), for phage amplifications. The crystal is incubated with an overnight *E. coli* ER2738 culture diluted 1:100 in LB medium, at 37° C. for 4.5 h. After this time, the cell culture is centrifuged for 30 s and the upper 80% of the supernatant is transferred to a fresh tube, ⅙ volume of PEG/

NaCl (20% polyethylene glycol-800, obtained from Sigma Chemical Co. St. Louis, Mo., 2.5 M sodium chloride) is added, and the phage is allowed to precipitate overnight at 4° C. The precipitate is collected by centrifugation at 10,000×g at 4° C. and the resulting pellet is resuspended in 1 mL of TBS. This is the first round of amplified stock. The amplified first round phage stock is then titered according to the method described below. For the next round of biopanning, more than $2 \times 10^{11}$ pfu of phage stock from the first round is used. The biopanning process is repeated for 3 to 4 rounds depending on the experiments.

After the acid wash steps in the final round of biopanning, the crystal is used to directly infect 500 μL of mid-log phase bacterial host cells, *E. coli* ER2738, which are then grown in LB medium for 20 min and then mixed with 3 mL of agarose top (LB medium with 5 mM $MgCl_2$, and 0.7% agarose) at 45° C. This mixture is spread onto a LB medium/IPTG/S-GAL™ plate (LB medium with 15 g/L agar, 0.05 g/L IPTG, and 0.04 g/L S-GAL™) and incubated overnight at 37° C. The black plaques are counted to calculate the phage titer. The single black plaques are randomly picked for DNA isolation and sequencing analysis. The peptide sequences identified are expected to have a high binding affinity for the specific face of the calcite crystal. This same procedure may be used to identify peptide sequences that bind to other faces of the same crystal or to crystalline faces of other calcite minerals.

Example 6

Prophetic

Preparation of Precipitated Calcium Carbonate Having Selected Crystallographic Faces The purpose of this prophetic Example is to describe how to prepare a precipitated calcium carbonate having selected crystallographic faces using a calcium carbonate-binding peptide reagent that comprises a calcium carbonate-binding domain that is selective for the desired crystal face.

SEED PHASE: Into a stainless steel reactor equipped with a stirrer, a gas injection tube and a liquid injection tube there is introduced a milk-of-lime ($Ca(OH)_2$) slurry and a calcium carbonate-binding peptide identified as described in Example 5 having a binding affinity to the common [21$\bar{3}$1] trigonal scalenohedra face of dogtooth calcite. The temperature of the $Ca(OH)_2$ slurry is adjusted to about 50° C. Vigorous agitation is commenced and a 15% $CO_2$/85% air gas mixture is introduced to effect carbonation of the $Ca(OH)_2$. Carbonation is continued until the pH of the slurry becomes 7.5 indicating that the reaction is substantially complete. Using electron microscopy it is possible to determine that the resulting product is a $CaCO_3$ having a scalenohedral morphology.

GROWTH PHASE: The growth phase is conducted in the stainless steel reactor as described above by the introduction of further amounts of $Ca(OH)_2$ while agitating the seed and introducing a 15% $CO_2$/85% air mixture into the reactor. The $Ca(OH)_2$ slurry concentration is 7.6% by weight and is added at a rate stoichiometric with the $CO_2$/air gas mixture being added simultaneously. The rate of $Ca(OH)_2$ addition is controlled to keep the slurry conductivity constant at about 3 mS. The growth phase is continued until the desired amount of $Ca(OH)_2$ had been added and the desired amount of growth the seeding material has been obtained. Electron microscopy may be used to demonstrate that the product is about 90 percent converted to the prismatic morphology.

Example 7

Prophetic

Selection of Calcite-Binding Peptides Selective for a Single Crystallographic Face Using mRNA Display Biopanning The purpose of this prophetic Example is to describe how to identify peptides that bind to a specific face of a calcium carbonate mineral using a modified mRNA display biopanning method.

Biopanning Against a Calcite Surface:

Unless otherwise noted, the mRNA display biopanning procedure described in Example 2 is repeated using the following material. The calcium carbonate substrate used is a natural, museum-quality single crystal of the trigonal scalenohedral (dog-tooth) form of calcite features adjacent crystal faces having enantiomorphic surface structures based upon the [21$\bar{3}$1] crystallographic faces. The markedly acentric surface structures of both the (3$\bar{1}\bar{2}$1) face (B) and the (21$\bar{3}$1) face (C) consist of corner-linked chains of $CaO_6$ octahedra, cross-linked by planar $CO_3$ groups, which are seen almost on edge. As described below, it is expected that one set of peptides will bind preferentially on the (3$\bar{1}\bar{2}$1) face, whereas others will bind preferentially on the (21$\bar{3}$1) face.

All but one of the faces of the crystal (the [21$\bar{3}$1] crystallographic face) are masked using a (perfluorohexyl)ethyl methacrylate polymer to make the surface hydrophobic. The remainder of the procedure is carried out on that one unmasked crystallographic face.

The mRNA display procedure described in Example 2 is conducted to identify peptides that selectively bind to the unmasked crystallographic face. This same procedure may be used to identify peptide sequences that bind to other faces of the same crystal or to crystalline faces of other calcite minerals.

What is claimed is:

1. A peptide reagent having a general structure selected from the group consisting of:
   a) $(CCBD)_n$;
   b) $(CCBD_x\text{-}BA_p)_n$;
   c) $(CCBD_x\text{-}AD_y)_n$;
   d) $(CCBD_x\text{-}TBD_y)_n$;
   e) $[(CCBD_x\text{-}L_s)_q\text{-}(TBD_y\text{-}L_t)_r]_n$;
   e) $[(CCBD_x\text{-}L_s)_q\text{-}(CCBD_y\text{-}L_t)_r]_n$;
   g) $(CCBD_x\text{-}L\text{-}BA)_n$; and
   h) $[(CCBD)_q\text{-}L_x\text{-}(CCBD)_r]_n\text{-}L\text{-}BA$;
   wherein:
   i) CCBD is a calcium carbonate-binding domain, comprising a sequence selected from the group consisting of SEQ ID Nos: 204-231;
   ii) BA is at least one benefit agent;
   iii) AD is at least one active domain incorporated into a calcium carbonate-binding peptide;
   iv) TBD is at least one target binding domain incorporated into a calcium carbonate-binding peptide;
   v) L is a linker molecule;
   vi) n, p, x, y, q, and r independently range from 1-20; and
   vii) s and t are each independently 0 or 1, provided that both s and t may not be 0.

2. An affinity complex between a calcium carbonate and a peptide reagent having a general structure selected from the group consisting of:
   a) $CC_m\text{-}(CCBD)_n$;
   b) $CC_m\text{-}(CCBD_x\text{-}BA_p)_n$;
   c) $CC_m\text{-}(CCBD_x\text{-}AD_y)_n$;
   d) $CC_m\text{-}(CCBD_x\text{-}TBD_y)_n$;
   e) $CC_m\text{-}[(CCBD_x\text{-}L_s)_q\text{-}(TBD_y\text{-}L_t)_r]_n$;
   f) $CC_m\text{-}[(CCBD_x\text{-}L_s)_q\text{-}(CCBD_y\text{-}L_t)_r]_n$;
   g) $CC_m\text{-}(CCBD_x\text{-}L\text{-}BA)_n$; and
   h) $CC_m\text{-}[(CCBD)_q\text{-}L_x\text{-}(CCBD)_r]_n\text{-}L\text{-}BA$;
   wherein:
   i) CC is a calcium carbonate moiety;
   ii) CCBD is a calcium carbonate-binding domain having affinity for the calcium carbonate moiety;
   iii) BA is at least one benefit agent;
   iv) AD is at least one active domain incorporated into a calcium carbonate-binding peptide;
   v) TBD is at least one target binding domain incorporated into a calcium carbonate-binding peptide;
   vi) L is a linker molecule;
   vii) m=the number of calcium carbonate moieties available for binding;
   viii) n=is less than or equal to m;
   ix) p, x, y, q, and r independently range from 1-20; and
   x) s and t are each independently 0 or 1, provided that both s and t may not be 0.

3. A composition comprising one or more of the peptide reagents of claim 1.

4. The composition according to claim 3 wherein the composition is selected from the group consisting of a personal care composition, an aqueous ink composition, and a paper composition.

5. The composition of claim 3, wherein the calcium carbonate is one or more calcium carbonate materials chosen from calcite, aragonite, Iceland spar, precipitated calcium carbonate, ground calcium carbonate, ankerite, benstonite, dolomite, huntite, kutnohorite, minrecordite, and norsethite.

6. The composition of claim 3, wherein said TBD is directed to binding one or more cellulosic materials, lignin materials and ligno-cellulosic materials.

7. The composition of claim 6 wherein said cellulosic materials, lignin materials and ligno-cellulosic materials are chosen from a group of cellulosic materials including wood pulp fibers; non-woody paper-making fibers from cotton; straws and grasses, including rice and esparto; canes and reeds, including bagasse; bamboos; stalks with bast fibers, including jute, flax, kenaf, cannabis, linen and ramie; and leaf fibers, including abaca and sisal; paper or polymer-coated paper including recycled paper and polymer-coated paper.

8. The composition of claim 7, wherein said cellulosic material is from one or more soft-wood or hardwood wood sources, including pines, spruces, firs, oaks, maples, eucalyptuses, poplars, beeches, and aspens.

9. The composition of claim 8, wherein said one or more wood source is in the form of sawdust, wood chips, or wood flour.

10. The composition of claim 4 wherein the composition is an aqueous ink composition that further comprises:
    a) an aqueous carrier medium; and
    b) a pigment;
    wherein said peptide reagent has the general structure:
    i) $(CCBD_x\text{-}BA_p)_n$ wherein BA is the pigment; or
    ii) $(CCBD_x\text{-}TBD_y)_n$; or $[(CCBD_x\text{-}L_s)_q\text{-}(TBD_y\text{-}L_t)_r]_n$ wherein the TBD has affinity for the pigment.

11. The composition of claim 4 wherein the composition is a personal care composition selected from the group consisting of: hair care, skin care, and cosmetic compositions and said TBD has affinity for a body surface.

12. The composition of claim 11 wherein the body surface is selected from the group consisting of hair, skin, nails, and teeth.

13. A process for applying a pigment to a calcium carbonate-coated paper comprising:

a) providing an aqueous ink composition according to claim 10; and
b) applying the aqueous ink composition to the calcium carbonate-coated paper, whereby the calcium carbonate-binding peptide binds to the calcium carbonate-coated paper, thereby attaching the pigment to the paper.

14. A process for making paper containing a calcium carbonate comprising:
a) preparing a thickstock comprising cellulosic fibers, and a specific calcium carbonate;
b) making an aqueous thinstock suspension by diluting with water said aqueous thickstock suspension;
c) draining the water from the thinstock to form a sheet; and
d) drying the sheet;
wherein one or more peptide reagents according to claim 1 having a general structure: $(CCBD_x\text{-}TBD_y)_n$ or $[(CCBD_x\text{-}L_s)_q\text{-}(TBD_y\text{-}L_t)_r]_n$ where CCBD is specific to the calcium carbonate used in step (a) and TBD is specific to cellulose, are added to:
i) the calcium carbonate of (a) before it's added to the thickstock;
ii) the thickstock of (a);
iii) the thinstock of (b); or
iv) any combination of (i), (ii), and (iii).

15. The process of claim 14 wherein the thickstock contains about 2.5% to about 20% by weight of calcium carbonate and cellulosic fiber in a dry weight ratio of 10:1 to 1:50.

16. The process of claim 14 wherein the $(CCBD_x\text{-}TBD_y)_n$ or $[(CCBD_x\text{-}L_s)_q\text{-}(TBD_y\text{-}L_t)_r]_n$ is present in the thickstock at a concentration from about 0.001% to about 5% dry weight based upon the dry weight of the suspension.

17. The process of claim 14 wherein the thinstock is formed in an amount of about 0.02 to about 2% dry weight based upon dry weight of the suspension.

18. The process of claim 14 wherein the water used to dilute the thickstock to thinstock is whitewater recycled from the papermaking process.

19. The process of claim 18 wherein the $(CCBD_x\text{-}TBD_y)_n$ or $[(CCBD_x\text{-}L_s)_q\text{-}(TBD_y\text{-}L_t)_r]_n$ is present in the whitewater utilized in the dilution of the thickstock to thinstock.

20. The paper made according to the process of claim 14.

21. A process for producing a beneficiated and dewatered calcium carbonate comprising:
(a) providing a calcium carbonate for which beneficiation is desired;
(b) forming an aqueous suspension of said calcium carbonate;
(c) deflocculating said aqueous suspension;
(d) adding one or more peptide reagents according to claim 1 having the general structure:
$(CCBD)_n$ or $[(CCBD_x\text{-}L_s)_q\text{-}(CCBD_y\text{-}L_t)_r]_n$ where CCBD is specific to the calcium carbonate used in step (a) to produce a flocculated calcium carbonate product in the suspension; and
(e) separating said flocculated calcium carbonate product from the suspension.

22. The process of claim 21 wherein the process further comprises one or more additional steps, in combination or alone, said steps including:
(i) adding a reducing agent to said deflocculated aqueous suspension of step (c);
(ii) redispersing the separated flocculated calcium carbonate product of step (e) to form a deflocculated calcium carbonate product having a higher weight percent solids content than the deflocculated aqueous suspension of step (c); and
(iii) further dewatering or drying said deflocculated calcium carbonate product of step (ii).

23. The beneficiated and dewatered calcium carbonate produced by the process of claim 21.

24. A process for producing a calcium carbonate-coated paper or paperboard comprising the steps of:
a) forming a base stock;
b) preparing a coating formulation comprising a calcium carbonate and one or more peptide reagents according to claim 1 having the general structure $(CCBD_x\text{-}TBD_y)_n$ or $[(CCBD_x\text{-}L_s)_q\text{-}(TBD_y\text{-}L_t)_r]_n$, in water;
c) coating at least one side of the base stock with the coating formulation; and
d) passing the coated base stock through a calender device.

25. The process of claim 24 wherein the TBD of the peptide $(CCBD_x\text{-}TBD_y)_n$ or $[(CCBD_x\text{-}L_s)_q\text{-}(TBD_y\text{-}L_t)_r]_n$ is specific to cellulose and the CCBD is specific to the particular calcium carbonate being employed.

26. The process of claim 24 wherein the TBD of the peptide $(CCBD_x\text{-}TBD_y)_n$ or $[(CCBD_x\text{-}L_s)_q\text{-}(TBD_y\text{-}L_t)_r]_n$ is specific to an ink pigment and the CCBD is specific to the particular calcium carbonate being employed.

27. The calcium carbonate-coated paper or paperboard prepared according to the process of claim 24.

28. A coating formulation comprising:
a) a calcium carbonate;
b) one or more peptide reagents according to claim 1 having the general structure $(CCBD_x\text{-}TBD_y)_n$ or $[(CCBD_x\text{-}L_s)_q\text{-}(TBD_y\text{-}L_t)_r]_n$; and
c) a solvent.

29. The composition of claim 3, wherein the TBD has a high affinity for one or more of the following:
a) acrylics or urethanes for use in automotive finishes or other paint products;
b) natural or synthetic rubbers for use in rubber products;
c) silicone materials for use in sealant products;
d) any of the functional ingredients selected from chelating agents, colorants, dispersants, emollients, emulsifiers, fragrances, humectants, opacifying agents, preservatives, skin conditioners, or thickeners for use in cosmetics; or
e) a polymer, including, nylons, polyesters, polycarbonates, acrylics, polyolefins, polyhydroxyalkanoates, and fluoropolymers.

30. The peptide reagent of claim 1 or the affinity complex of claim 2 wherein the linker molecule is selected from the group consisting of: a peptide linker and an organic linker.

31. The peptide reagent of claim 1 or the affinity complex of claim 2 wherein the active domain has one or more functionality selected from the group consisting of: a linker, a binding functionality, a catalytic functionality and an antimicrobial functionality.

32. The peptide reagent according to claim 1 or an affinity complex of claim 2 wherein the target binding domain has an affinity for one or more members of the group consisting of affinity for pigments, affinity for benefit agents, affinity for print media, affinity for chemical functional groups, affinity for body surfaces, and affinity for biological analytes.

33. The peptide reagent or affinity complex according to claim 32 wherein the target binding peptide binds to a target selected from the group consisting of: proteins, nucleic acids, cells, cell membrane fractions, antibodies, antibody fragments, viral proteins, plant fibers, synthetic fibers, and organic and inorganic complexes.

34. The peptide reagent or an affinity complex according to claim 32 wherein the target binding domain is a body surface binding domain.

35. The peptide reagent or an affinity complex according to claim 34 wherein the body surface binding domain binds to a body surface selected from the group consisting of hair, skin, nails and teeth.

36. The peptide reagent of claim 1 or an affinity complex of claim 2 wherein the calcium carbonate moiety is incorporated into a surface.

37. The peptide reagent or an affinity complex of claim 36 wherein the surface is selected from the group consisting of paper, a solid support, a bead, a microsphere, a sheet, and a fiber.

38. The peptide reagent or an affinity complex of claim 37 wherein said paper, solid support, bead, microsphere, sheet, and fiber comprises a dye.

39. The peptide reagent of claim 1 or an affinity complex of claim 2 wherein the calcium carbonate moiety is comprised within a calcium carbonate film.

40. The peptide reagent of claim 1 or an affinity complex of claim 2 wherein the calcium carbonate moiety is comprised within a print medium.

41. The peptide reagent or an affinity complex of claim 40 wherein the print medium is selected from the group consisting of paper, sheets, films, nonwovens, and textile fabrics.

42. The composition of claim 3, wherein said composition further comprises one or more of the following, pharmaceuticals, cosmetic, nutraceutical, cancer treatment, markers, colorants, conditioners, fragrances, antibacterial agents, antiviral agents, antifungal agents, anti-cancer agents, vaccines, radiolabels, anti-inflammatories, anti-glaucomic agents, anesthetics, anti-neoplastic agents, antibodies, and hormones.

43. A method for binding a substrate comprising at least one calcium carbonate moiety to a target comprising:
 (a) providing a peptide reagent according to claim 1: and
 (b) contacting the peptide reagent of (a) with a substrate comprising said calcium carbonate moiety under conditions whereby the peptide reagent binds to the calcium carbonate moiety.

44. A method for delivering a benefit agent to a substrate comprising calcium carbonate or a calcium carbonate moiety comprising:
 a) providing one or more peptide reagents, $(CCBD_x\text{-}TBD_y)_n$ or $[(CCBD_x\text{-}L_s)_q\text{-}(TBD_y\text{-}Lt)_r]_n$; according to claim 1;
 b) contacting said target with said peptide reagent of (a) thereby forming a complex between said target and said peptide;
 c) contacting said complex with said substrate comprising said calcium carbonate moiety thereby binding said substrate to said target.

45. A method according to claim 44 wherein the benefit agent is selected from the group consisting of pharmaceuticals, markers, colorants, conditioners, and fragrances.

46. A method for adhering two surfaces comprising:
 a) providing a first surface comprising calcium carbonate comprising a first peptide reagent according to claim 1 having the general formula: $((CCBD_x\text{-}AD1_y)_n;$
 wherein:
  i) CCBD is a calcium carbonate-binding domain;
  ii) AD1 is a first active domain; and
  iii) x, y, and n independently range from 1-20; and
 b) providing a second surface comprising a target molecule comprising a second peptide reagent have the general formula (TBD-AD2) wherein:
  i) TBD is a target binding domain; and
  ii) AD2 is a second active domain having affinity for the first active domain; and
 c) juxtaposing the first and second surfaces wherein the first and second peptide reagents adhere to each other through the first and second active domains, whereby the surfaces are adhered.

47. A method for adhering two surfaces comprising:
 (a) providing a first surface comprising a first target molecule comprising a first peptide reagent having the general formula $(CCBD_x\text{-}TBD1_y)_n$ wherein:
  i) TBD1 is a first target binding domain;
  ii) CCBD is a calcium carbonate-binding domain; and
  iii) x, y, and n independently range from 1-20;
 b) providing a second surface comprising a second target molecule comprising a second peptide reagent having the general formula $(CCBD_x\text{-}TBD2_y)_n)$ wherein:
  i) TBD2 is a second target binding domain;
  ii) CCBD is a calcium carbonate-binding domain; and
  iii) x, y, and n independently range from 1-20; and
 c) juxtaposing the first and second surfaces in the presence of a calcium carbonate moiety wherein the first and second peptide reagents adhere to the calcium carbonate moiety through the calcium carbonate binding domain, whereby the surfaces are adhered.

48. The peptide reagent of claim 1 or an affinity complex of claim 2 wherein the calcium carbonate-peptide binding domain is isolated by a process comprising the steps of:
 (a) providing a library of combinatorially generated peptides;
 (b) contacting the library of (a) with a calcium carbonate sample to form a reaction solution comprising:
  (i) peptide-calcium carbonate complex;
  (ii) unbound calcium carbonate, and
  (iii) uncomplexed peptides;
 (c) isolating the peptide-calcium carbonate complex of (b);
 (d) eluting the weakly bound peptides from the isolated peptide complex of (c) whereby the calcium carbonate-binding peptide domain is isolated.

\* \* \* \* \*

UNITED STATES PATENT AND TRADEMARK OFFICE
CERTIFICATE OF CORRECTION

PATENT NO. : 7,754,680 B2
APPLICATION NO. : 11/828539
DATED : July 13, 2010
INVENTOR(S) : Scott D. Cunningham et al.

Page 1 of 1

It is certified that error appears in the above-identified patent and that said Letters Patent is hereby corrected as shown below:

Column 149, line 47, after "peptide;" insert --and--

Column 150, line 48, after "(b);" insert --and--

Signed and Sealed this

Thirtieth Day of November, 2010

David J. Kappos
*Director of the United States Patent and Trademark Office*

SEQUENCE LISTING

<160> NUMBER OF SEQ ID NOS: 232

<210> SEQ ID NO 1
<211> LENGTH: 12
<212> TYPE: PRT
<213> ORGANISM: Artificial sequence
<220> FEATURE:
<223> OTHER INFORMATION: Polymethylmethacrylate binding peptides

```
<400> SEQUENCE: 1

Ile Pro Trp Trp Asn Ile Arg Ala Pro Leu Asn Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 2

Thr Ala Val Met Asn Val Val Asn Asn Gln Leu Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 3

Val Pro Trp Trp Ala Pro Ser Lys Leu Ser Met Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 4

Met Val Met Ala Pro His Thr Pro Arg Ala Arg Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 5

Thr Tyr Pro Asn Trp Ala His Leu Leu Ser His Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 6

Thr Pro Trp Trp Arg Ile Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Polymethylmethacrylate-binding peptide
```

```
<400> SEQUENCE: 7

Asp Leu Thr Leu Pro Phe His
1               5

<210> SEQ ID NO 8
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 8

Gly Thr Ser Ile Pro Ala Met
1               5

<210> SEQ ID NO 9
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 9

His His Lys His Val Val Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 10

His His His Lys His Phe Met
1               5

<210> SEQ ID NO 11
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 11

His His His Arg His Gln Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 12

His His Trp His Ala Pro Arg
1               5

<210> SEQ ID NO 13
<211> LENGTH: 17
<212> TYPE: PRT
<213> ORGANISM: Artificial sequence
<220> FEATURE:
<223> OTHER INFORMATION: antimicrobial peptide sequence
```

```
<400> SEQUENCE: 13

Pro Lys Gly Leu Lys Lys Leu Leu Lys Gly Leu Lys Lys Leu Leu Lys
1               5                   10                  15

Leu

<210> SEQ ID NO 14
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 14

Lys Gly Leu Lys Lys Leu Leu Lys Gly Leu Lys Lys Leu Leu Lys Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 15

Lys Gly Leu Lys Lys Leu Leu Lys Leu Leu Lys Lys Leu Leu Lys Leu
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 16

Leu Lys Lys Leu Leu Lys Leu Leu Lys Lys Leu Leu Lys Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Antimicrobial peptide sequence

<400> SEQUENCE: 17

Leu Lys Lys Leu Leu Lys Leu Leu Lys Lys Leu Leu
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Antimicrobial peptide sequences

<400> SEQUENCE: 18

Val Ala Lys Lys Leu Ala Lys Leu Ala Lys Lys Leu Ala Lys Leu Ala
1               5                   10                  15

Leu

<210> SEQ ID NO 19
<211> LENGTH: 13
<212> TYPE: PRT
<213> ORGANISM: Artificial Sequence
```

```
<220> FEATURE:
<223> OTHER INFORMATION: Antimicrobial peptide sequences

<400> SEQUENCE: 19

Phe Ala Lys Leu Leu Ala Lys Ala Leu Lys Lys Leu Leu
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 20

Lys Gly Leu Lys Lys Gly Leu Lys Leu Leu Lys Lys Leu Leu Lys Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 21

Lys Gly Leu Lys Lys Leu Leu Lys Leu Gly Lys Lys Leu Leu Lys Leu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 22

Lys Gly Leu Lys Lys Leu Gly Lys Leu Leu Lys Kys Leu Leu Lys Leu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 23

Lys Gly Leu Lys Lys Leu Leu Lys Leu Leu Lys Lys Gly Leu Lys Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 24

Lys Gly Leu Lys Lys Leu Leu Lys Leu Leu Lys Leu Gly Lys Lys Leu
1               5                   10                  15

<210> SEQ ID NO 25
<211> LENGTH: 19
<212> TYPE: PRT
<213> ORGANISM: Artificial Sequence
```

```
<220> FEATURE:
<223> OTHER INFORMATION: Antimicrobial peptide sequences

<400> SEQUENCE: 25

Phe Ala Leu Ala Leu Lys Ala Leu Lys Lys Leu Lys Lys Ala Leu Lys
1               5                   10                  15

Lys Ala Leu

<210> SEQ ID NO 26
<211> LENGTH: 17
<212> TYPE: PRT
<213> ORGANISM: Artificial Sequence
<220> FEATURE:
<223> OTHER INFORMATION: Antimicrobial peptide sequence

<400> SEQUENCE: 26

Phe Ala Lys Lys Leu Ala Lys Leu Ala Lys Lys Leu Ala Lys Leu Ala
1               5                   10                  15

Leu

<210> SEQ ID NO 27
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 27

Phe Ala Lys Leu Leu Ala Lys Leu Ala Lys Lys Leu Leu
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Antimicrobial peptide sequences

<400> SEQUENCE: 28

Phe Ala Lys Lys Leu Ala Lys Leu Ala Leu Lys Leu Ala Lys Leu
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Antimicrobial peptide sequences

<400> SEQUENCE: 29

Phe Ala Lys Lys Leu Ala Lys Lys Leu Leu
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Antimicrobial peptide sequence

<400> SEQUENCE: 30

Phe Ala Lys Leu Leu Ala Lys Leu Ala Lys Lys Val Leu
1               5                   10
```

```
<210> SEQ ID NO 31
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 31

Lys Tyr Lys Lys Ala Leu Lys Lys Leu Ala Lys Leu Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Antimicrobial peptide sequences

<400> SEQUENCE: 32

Phe Ala Leu Leu Lys Ala Leu Leu Lys Lys Ala Leu
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 33

Lys Arg Leu Phe Lys Lys Leu Lys Phe Ser Leu Arg Lys Tyr
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 34

Lys Arg Leu Phe Lys Lys Leu Leu Phe Ser Leu Arg Lys Tyr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 35

Leu Leu Leu Phe Leu Leu Lys Lys Arg Lys Lys Arg Lys Tyr
1               5                   10

<210> SEQ ID NO 36
<211> LENGTH: 36
<212> TYPE: PRT
<213> ORGANISM: Hyalophora cecropia

<400> SEQUENCE: 36

Lys Trp Lys Leu Phe Lys Lys Ile Glu Lys Val Gly Gln Asn Ile Arg
1               5                   10                  15
```

```
Asp Gly Ile Ile Lys Ala Gly Pro Ala Val Ala Trp Gly Gln Ala Thr
            20                  25                  30

Gln Ile Ala Lys
        35

<210> SEQ ID NO 37
<211> LENGTH: 23
<212> TYPE: PRT
<213> ORGANISM: Xenopus sp.

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 22
<212> TYPE: PRT
<213> ORGANISM: Xenopus sp.

<400> SEQUENCE: 38

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 39
<211> LENGTH: 12
<212> TYPE: PRT
<213> ORGANISM: Bos taurus

<400> SEQUENCE: 39

Arg Leu Cys Arg Ile Val Val Ile Arg Val Cys Arg
1               5                   10

<210> SEQ ID NO 40
<211> LENGTH: 13
<212> TYPE: PRT
<213> ORGANISM: Bos sp.

<400> SEQUENCE: 40

Ile Leu Pro Trp Lys Trp Pro Trp Trp Pro Trp Arg Arg
1               5                   10

<210> SEQ ID NO 41
<211> LENGTH: 24
<212> TYPE: PRT
<213> ORGANISM: Homo sapiens

<400> SEQUENCE: 41

Asp Ser His Ala Lys Arg His His Gly Tyr Lys Arg Lys Phe His Glu
1               5                   10                  15

Lys His His Ser His Arg Gly Tyr
            20

<210> SEQ ID NO 42
<211> LENGTH: 7
<212> TYPE: PRT
<213> ORGANISM: Artificial Sequence
<220> FEATURE:
<223> OTHER INFORMATION: Pigment binding peptide sequence
```

-continued

```
<400> SEQUENCE: 42

Met Pro Pro Pro Leu Met Gln
1               5

<210> SEQ ID NO 43
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 43

Phe His Glu Asn Trp Pro Ser
1               5

<210> SEQ ID NO 44
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 44

Arg Thr Ala Pro Thr Thr Pro Leu Leu Leu Ser Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 45

Trp His Leu Ser Trp Ser Pro Val Pro Leu Pro Thr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 46

Pro His Ala Arg Leu Val Gly
1               5

<210> SEQ ID NO 47
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 47

Asn Ile Pro Tyr His His Pro
1               5

<210> SEQ ID NO 48
<211> LENGTH: 7
<212> TYPE: PRT
<213> ORGANISM: Artificial Sequence
<220> FEATURE:
<223> OTHER INFORMATION: Pigment binding peptide sequences
```

```
<400> SEQUENCE: 48

Thr Thr Met Pro Ala Ile Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 49

His Asn Leu Pro Pro Arg Ser
1               5

<210> SEQ ID NO 50
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 50

Ala His Lys Thr Gln Met Gly Val Arg Gln Pro Ala
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 51

Ala Asp Asn Val Gln Met Gly Val Ser His Thr Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 52

Ala His Asn Ala Gln Met Gly Val Ser His Pro Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 53

Ala Asp Tyr Val Gly Met Gly Val Ser His Arg Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Pigment binding peptide sequence
```

```
<400> SEQUENCE: 54

Ser Val Ser Val Gly Met Lys Pro Ser Pro Arg Pro
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 55

Tyr Pro Asn Thr Ala Leu Val
1               5

<210> SEQ ID NO 56
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 56

Val Ala Thr Arg Ile Val Ser
1               5

<210> SEQ ID NO 57
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 57

His Ser Leu Lys Asn Ser Met Leu Thr Val Met Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 58

Asn Tyr Pro Thr Gln Ala Pro
1               5

<210> SEQ ID NO 59
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 59

Lys Cys Cys Tyr Ser Val Gly
1               5

<210> SEQ ID NO 60
<211> LENGTH: 12
<212> TYPE: PRT
<213> ORGANISM: Artificial Sequence
<220> FEATURE:
<223> OTHER INFORMATION: Pigment binding peptide sequences
```

```
<400> SEQUENCE: 60

Arg His Asp Leu Asn Thr Trp Leu Pro Pro Val Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 61

Glu Ile Ser Leu Pro Ala Lys Leu Pro Ser Ala Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 62

Ser Asp Tyr Val Gly Met Arg Pro Ser Pro Arg His
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 63

Ser Asp Tyr Val Gly Met Arg Leu Ser Pro Ser Gln
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 64

Ser Val Ser Val Gly Ile Gln Pro Ser Pro Arg Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 65

Tyr Val Ser Val Gly Ile Lys Pro Ser Pro Arg Pro
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Pigment binding peptide sequences
```

-continued

```
<400> SEQUENCE: 66

Tyr Val Cys Glu Gly Ile His Pro Cys Pro Arg Pro
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 67

Ser Ile Leu Pro Tyr Pro Tyr
1               5

<210> SEQ ID NO 68
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 68

Ser Thr Ala Ser Tyr Thr Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 69

Leu Pro Val Arg Pro Trp Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 70

Gly Asn Thr Pro Ser Arg Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Print Medium-Binding Peptides

<400> SEQUENCE: 71

His Ala Ile Tyr Pro Arg His
1               5

<210> SEQ ID NO 72
<211> LENGTH: 7
<212> TYPE: PRT
<213> ORGANISM: Artificial Sequence
<220> FEATURE:
<223> OTHER INFORMATION: Print Medium-Binding Peptides
```

```
<400> SEQUENCE: 72

Tyr Gln Asp Ser Ala Lys Thr
1               5

<210> SEQ ID NO 73
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 73

Val Pro Arg Val Thr Ser Ile
1               5

<210> SEQ ID NO 74
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 74

Met Ala Asn His Asn Leu Ser
1               5

<210> SEQ ID NO 75
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 75

Phe His Glu Asn Trp Pro Ser
1               5

<210> SEQ ID NO 76
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 76

Thr His Lys Thr Ser Thr Gln Arg Leu Leu Ala Ala
1               5                   10

<210> SEQ ID NO 77
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 77

Lys Cys Cys Tyr Val Asn Val Gly Ser Val Phe Ser
1               5                   10

<210> SEQ ID NO 78
<211> LENGTH: 12
<212> TYPE: PRT
<213> ORGANISM: Artificial sequence
<220> FEATURE:
<223> OTHER INFORMATION: Cellulose-Binding Peptide
```

```
<400> SEQUENCE: 78

Ala His Met Gln Phe Arg Thr Ser Leu Thr Pro His
1               5                  10

<210> SEQ ID NO 79
<211> LENGTH: 12
<212> TYPE: PRT
<213> ORGANISM: Artificial sequence
<220> FEATURE:
<223> OTHER INFORMATION: Poly(ethylene terephthalate)-Binding Peptide

<400> SEQUENCE: 79

Gly Thr Ser Asp His Met Ile Met Pro Phe Phe Asn
1               5                  10

<210> SEQ ID NO 80
<211> LENGTH: 7
<212> TYPE: PRT
<213> ORGANISM: Artificial sequence
<220> FEATURE:
<223> OTHER INFORMATION: Skin Binding Peptide Domain

<400> SEQUENCE: 80

Phe Thr Gln Ser Leu Pro Arg
1               5

<210> SEQ ID NO 81
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 81

Thr Pro Phe His Ser Pro Glu Asn Ala Pro Gly Ser
1               5                  10

<210> SEQ ID NO 82
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 82

Lys Gln Ala Thr Phe Pro Pro Asn Pro Thr Ala Tyr
1               5                  10

<210> SEQ ID NO 83
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 83

His Gly His Met Val Ser Thr Ser Gln Leu Ser Ile
1               5                  10

<210> SEQ ID NO 84
<211> LENGTH: 7
<212> TYPE: PRT
<213> ORGANISM: Artificial Sequence
<220> FEATURE:
<223> OTHER INFORMATION: Skin Binding Peptide Domain
```

```
<400> SEQUENCE: 84

Leu Ser Pro Ser Arg Met Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 85

Leu Pro Ile Pro Arg Met Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 86

His Gln Arg Pro Tyr Leu Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 87

Phe Pro Pro Leu Leu Arg Leu
1               5

<210> SEQ ID NO 88
<211> LENGTH: 12
<212> TYPE: PRT
<213> ORGANISM: Artificial Sequence
<220> FEATURE:
<223> OTHER INFORMATION: Nail Binding Peptide Domain

<400> SEQUENCE: 88

Ala Leu Pro Arg Ile Ala Asn Thr Trp Ser Pro Ser
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Nail Binding Peptide Domain

<400> SEQUENCE: 89

Tyr Pro Ser Phe Ser Pro Thr Tyr Arg Pro Ala Phe
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Hair Binding Peptide Domain
```

-continued

```
<400> SEQUENCE: 90

Tyr Pro Ser Phe Ser Pro Thr Tyr Arg Pro Ala Phe
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 91

Ala Leu Pro Arg Ile Ala Asn Thr Trp Ser Pro Ser
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Hair Binding Peptide Domain

<400> SEQUENCE: 92

Leu Glu Ser Thr Pro Lys Met Lys
1               5

<210> SEQ ID NO 93
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 93

Ser Val Ser Val Gly Met Lys Pro Ser Pro Arg Pro
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 94

Leu Asp Val Glu Ser Tyr Lys Gly Thr Ser Met Pro
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 95

Arg Val Pro Asn Lys Thr Val Thr Val Asp Gly Ala
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Hair Binding Peptide Domain
```

```
<400> SEQUENCE: 96

Asp Arg His Lys Ser Lys Tyr Ser Ser Thr Lys Ser
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 97

Lys Asn Phe Pro Gln Gln Lys Glu Phe Pro Leu Ser
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 98

Gln Arg Asn Ser Pro Pro Ala Met Ser Arg Arg Asp
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 99

Thr Arg Lys Pro Asn Met Pro His Gly Gln Tyr Leu
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 100

Lys Pro Pro His Leu Ala Lys Leu Pro Phe Thr Thr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 101

Asn Lys Arg Pro Pro Thr Ser His Arg Ile His Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Hair Binding Peptide Domain
```

```
<400> SEQUENCE: 102

Asn Leu Pro Arg Tyr Gln Pro Pro Cys Lys Pro Leu
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 103

Arg Pro Pro Trp Lys Lys Pro Ile Pro Pro Ser Glu
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 104

Arg Gln Arg Pro Lys Asp His Phe Phe Ser Arg Pro
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (6)..(6)
<223> OTHER INFORMATION: X= T or P
<220> FEATURE:
<221> NAME/KEY: MISC_FEATURE
<222> LOCATION: (12)..(12)
<223> OTHER INFORMATION: X= E or A

<400> SEQUENCE: 105

Ser Val Pro Asn Lys Xaa Val Thr Val Asp Gly Xaa
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 106

Thr Thr Lys Trp Arg His Arg Ala Pro Val Ser Pro
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 107

Trp Leu Gly Lys Asn Arg Ile Lys Pro Arg Ala Ser
1               5                   10
```

```
<210> SEQ ID NO 108
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 108

Ser Asn Phe Lys Thr Pro Leu Pro Leu Thr Gln Ser
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 109

Lys Glu Leu Gln Thr Arg Asn Val Val Gln Arg Glu
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 110

Gly Met Pro Ala Met His Trp Ile His Pro Phe Ala
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 111

Thr Pro Thr Ala Asn Gln Phe Thr Gln Ser Val Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 112

Ala Ala Gly Leu Ser Gln Lys His Glu Arg Asn Arg
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 113

Glu Thr Val His Gln Thr Pro Leu Ser Asp Arg Pro
1               5                   10
```

```
<210> SEQ ID NO 114
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 114

Leu Pro Ala Leu His Ile Gln Arg His Pro Arg Met
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 115

Gln Pro Ser His Ser Gln Ser His Asn Leu Arg Ser
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 116

Arg Gly Ser Gln Lys Ser Lys Pro Pro Arg Pro Pro
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 117

Thr His Thr Gln Lys Thr Pro Leu Leu Tyr Tyr His
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 118

Thr Lys Gly Ser Ser Gln Ala Ile Leu Lys Ser Thr
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 119

Asp Leu His Thr Val Tyr His
1               5
```

```
<210> SEQ ID NO 120
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 120

His Ile Lys Pro Pro Thr Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 121

His Pro Val Trp Pro Ala Ile
1               5

<210> SEQ ID NO 122
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 122

Met Pro Leu Tyr Tyr Leu Gln
1               5

<210> SEQ ID NO 123
<211> LENGTH: 26
<212> TYPE: PRT
<213> ORGANISM: Artificial Sequence
<220> FEATURE:
<223> OTHER INFORMATION: Hair Binding Peptide Domain

<400> SEQUENCE: 123

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 124
<211> LENGTH: 41
<212> TYPE: PRT
<213> ORGANISM: Artificial Sequence
<220> FEATURE:
<223> OTHER INFORMATION: Hair Binding Peptide Domain

<400> SEQUENCE: 124

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
            35                  40

<210> SEQ ID NO 125
<211> LENGTH: 7
<212> TYPE: PRT
<213> ORGANISM: Artificial Sequence
```

<220> FEATURE:
<223> OTHER INFORMATION: Hair Binding Peptide Domain

<400> SEQUENCE: 125

Lys His Pro Thr Tyr Arg Gln
1               5

<210> SEQ ID NO 126
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 126

His Pro Met Ser Ala Pro Arg
1               5

<210> SEQ ID NO 127
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 127

Met Pro Lys Tyr Tyr Leu Gln
1               5

<210> SEQ ID NO 128
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 128

Met His Ala His Ser Ile Ala
1               5

<210> SEQ ID NO 129
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 129

Thr Ala Ala Thr Thr Ser Pro
1               5

<210> SEQ ID NO 130
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 130

Leu Gly Ile Pro Gln Asn Leu
1               5

<210> SEQ ID NO 131
<211> LENGTH: 12
<212> TYPE: PRT
<213> ORGANISM: Artificial Sequence

```
<220> FEATURE:
<223> OTHER INFORMATION: Hair Binding Peptide Domain

<400> SEQUENCE: 131

Ala Lys Pro Ile Ser Gln His Leu Gln Arg Gly Ser
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 132

Ala Pro Pro Thr Pro Ala Ala Ala Ser Ala Thr Thr
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 133

Asp Pro Thr Glu Gly Ala Arg Arg Thr Ile Met Thr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 134

Glu Gln Ile Ser Gly Ser Leu Val Ala Ala Pro Trp
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 135

Leu Asp Thr Ser Phe Pro Pro Val Pro Phe His Ala
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Hair Binding Peptide Domain

<400> SEQUENCE: 136

Leu Pro Arg Ile Ala Asn Thr Trp Ser Pro Ser
1               5                   10

<210> SEQ ID NO 137
<211> LENGTH: 12
<212> TYPE: PRT
<213> ORGANISM: Artificial Sequence
```

```
<220> FEATURE:
<223> OTHER INFORMATION: Hair Binding Peptide Domain

<400> SEQUENCE: 137

Arg Thr Asn Ala Ala Asp His Pro Ala Ala Val Thr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: HairBinding Peptide Domain

<400> SEQUENCE: 138

Ser Leu Asn Trp Val Thr Ile Pro Gly Pro Lys Ile
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 139

Thr Asp Met Gln Ala Pro Thr Lys Ser Tyr Ser Asn
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 140

Thr Ile Met Thr Lys Ser Pro Ser Leu Ser Cys Gly
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 141

Thr Pro Ala Leu Asp Gly Leu Arg Gln Pro Leu Arg
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 142

Thr Tyr Pro Ala Ser Arg Leu Pro Leu Leu Ala Pro
1               5                   10

<210> SEQ ID NO 143
<211> LENGTH: 12
<212> TYPE: PRT
<213> ORGANISM: Artificial Sequence
```

```
<220> FEATURE:
<223> OTHER INFORMATION: Hair Binding Peptide Domain

<400> SEQUENCE: 143

Thr Tyr Pro Ala Ser Arg Leu Pro Leu Leu Ala Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 144

Thr Asp Pro Thr Pro Phe Ser Ile Ser Pro Glu Arg
1               5                   10

<210> SEQ ID NO 145
<211> LENGTH: 20
<212> TYPE: PRT
<213> ORGANISM: Artificial Sequence
<220> FEATURE:
<223> OTHER INFORMATION: Hair Binding Peptide Domain

<400> SEQUENCE: 145

Cys Ala Ala Gly Cys Cys Thr Cys Ala Gly Cys Gly Ala Cys Cys Gly
1               5                   10                  15

Ala Ala Thr Ala
            20

<210> SEQ ID NO 146
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 146

Trp His Asp Lys Pro Gln Asn Ser Ser Lys Ser Thr
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 147

Asn Glu Val Pro Ala Arg Asn Ala Pro Trp Leu Val
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Hair Binding Peptide Domain

<400> SEQUENCE: 148

Asn Ser Pro Gly Tyr Gln Ala Asp Ser Val Ala Ile Gly
1               5                   10
```

```
<210> SEQ ID NO 149
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 149

Thr Gln Asp Ser Ala Gln Lys Ser Pro Ser Pro Leu
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 150

Thr Pro Pro Glu Leu Leu His Gly Asp Pro Arg Ser
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 151

Thr Pro Pro Thr Asn Val Leu Met Leu Ala Thr Lys
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 152

Asn Thr Ser Gln Leu Ser Thr
1               5

<210> SEQ ID NO 153
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 153

Asn Thr Pro Lys Glu Asn Trp
1               5

<210> SEQ ID NO 154
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 154

Asn Thr Pro Ala Ser Asn Arg
1               5
```

<210> SEQ ID NO 155
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 155

Pro Arg Gly Met Leu Ser Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 156

Pro Pro Thr Tyr Leu Ser Thr
1               5

<210> SEQ ID NO 157
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 157

Thr Ile Pro Thr His Arg Gln His Asp Tyr Arg Ser
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 158

Thr Pro Pro Thr His Arg Leu
1               5

<210> SEQ ID NO 159
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 159

Leu Pro Thr Met Ser Thr Pro
1               5

<210> SEQ ID NO 160
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 160

Leu Gly Thr Asn Ser Thr Pro
1               5

```
<210> SEQ ID NO 161
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 161

Thr Pro Leu Thr Gly Ser Thr Asn Leu Leu Ser Ser
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 162

Thr Pro Leu Thr Lys Glu Thr
1               5

<210> SEQ ID NO 163
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 163

Gln Gln Ser His Asn Pro Pro
1               5

<210> SEQ ID NO 164
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 164

Thr Gln Pro His Asn Pro Pro
1               5

<210> SEQ ID NO 165
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 165

Ser Thr Asn Leu Leu Arg Thr Ser Thr Val His Pro
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 166

His Thr Gln Pro Ser Tyr Ser Ser Thr Asn Leu Phe
1               5                   10
```

```
<210> SEQ ID NO 167
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 167

Ser Leu Leu Ser Ser His Ala
1               5

<210> SEQ ID NO 168
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 168

Gln Gln Ser Ser Ile Ser Leu Ser Ser His Ala Val
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 169

Asn Ala Ser Pro Ser Ser Leu
1               5

<210> SEQ ID NO 170
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 170

His Ser Pro Ser Ser Leu Arg
1               5

<210> SEQ ID NO 171
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X= H, R or N

<400> SEQUENCE: 171

Lys Xaa Ser His His Thr His
1               5

<210> SEQ ID NO 172
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X=H or Ror N
```

```
<220> FEATURE:
<221> NAME/KEY: MISC_FEATURE
<222> LOCATION: (2)..(2)
<223> OTHER INFORMATION: X= H, R, or N

<400> SEQUENCE: 172

Glu Xaa Ser His His Thr His
1               5

<210> SEQ ID NO 173
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 173

Leu Glu Ser Thr Ser Leu Leu
1               5

<210> SEQ ID NO 174
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 174

Thr Pro Leu Thr Lys Glu Thr
1               5

<210> SEQ ID NO 175
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 175

Lys Gln Ser His Asn Pro Pro
1               5

<210> SEQ ID NO 176
<211> LENGTH: 8
<212> TYPE: PRT
<213> ORGANISM: Artificial Sequence
<220> FEATURE:
<223> OTHER INFORMATION: Linker Peptide

<400> SEQUENCE: 176

Leu Glu Ser Gly Asp Glu Val Asp
1               5

<210> SEQ ID NO 177
<211> LENGTH: 37
<212> TYPE: PRT
<213> ORGANISM: Artificial Sequence
<220> FEATURE:
<223> OTHER INFORMATION: Linker peptide

<400> SEQUENCE: 177

Thr Ser Thr Ser Lys Ala Ser Thr Thr Thr Ser Ser Lys Thr Thr
1               5                   10                  15
```

```
Thr Thr Ser Ser Lys Thr Thr Thr Thr Ser Lys Thr Ser Thr Thr
            20                  25                  30

Ser Ser Ser Ser Thr
            35

<210> SEQ ID NO 178
<211> LENGTH: 22
<212> TYPE: PRT
<213> ORGANISM: Artificial Sequence
<220> FEATURE:
<223> OTHER INFORMATION: Linker peptide

<400> SEQUENCE: 178

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 179
<211> LENGTH: 10
<212> TYPE: PRT
<213> ORGANISM: Artificial Sequence
<220> FEATURE:
<223> OTHER INFORMATION: Linker peptide

<400> SEQUENCE: 179

Gly Pro Gly Gly Tyr Gly Pro Gly Gln Gln
1               5                   10

<210> SEQ ID NO 180
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 180

Lys Thr Pro Pro Thr Arg Pro
1               5

<210> SEQ ID NO 181
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 181

Val Ile Asn Pro Asn Leu Asp
1               5

<210> SEQ ID NO 182
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 182

Lys Val Trp Ile Val Ser Thr
1               5

<210> SEQ ID NO 183
<211> LENGTH: 7
<212> TYPE: PRT
<213> ORGANISM: Artificial Sequence
```

```
<220> FEATURE:
<223> OTHER INFORMATION: Nylon-Binding Peptide

<400> SEQUENCE: 183

Ala Glu Pro Val Ala Met Leu
1               5

<210> SEQ ID NO 184
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 184

Ala Glu Leu Val Ala Met Leu
1               5

<210> SEQ ID NO 185
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 185

His Ser Leu Arg Leu Asp Trp
1               5

<210> SEQ ID NO 186
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 186

Glu Ser Ser Tyr Ser Trp Ser Pro Ala Arg Leu Ser
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 187

Gly Pro Leu Lys Leu Leu His Ala Trp Trp Gln Pro
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 188

Asn Ala Leu Thr Arg Pro Val
1               5

<210> SEQ ID NO 189
<211> LENGTH: 7
<212> TYPE: PRT
<213> ORGANISM: Artificial Sequence
```

```
<220> FEATURE:
<223> OTHER INFORMATION: Poly(tetrafluoroethylene)-Binding Peptide

<400> SEQUENCE: 189

Ser Ala Pro Ser Ser Lys Asn
1               5

<210> SEQ ID NO 190
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 190

Ser Val Ser Val Gly Met Lys Pro Ser Pro Arg Pro
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 191

Ser Tyr Tyr Ser Leu Pro Pro Ile Phe His Ile Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 192

Thr Phe Thr Pro Tyr Ser Ile Thr His Ala Leu Leu
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 193

Thr Met Gly Phe Thr Ala Pro Arg Phe Pro His Tyr
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 194

Thr Asn Pro Phe Pro Pro Pro Pro Ser Ser Pro Ala
1               5                   10

<210> SEQ ID NO 195
<211> LENGTH: 15
<212> TYPE: PRT
<213> ORGANISM: Artificial Sequence
```

-continued

```
<220> FEATURE:
<223> OTHER INFORMATION: Hair-binding peptide

<400> SEQUENCE: 195

Ser Thr Leu His Lys Tyr Lys Ser Gln Asp Pro Thr Pro His His
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 196

His Asp His Lys Asn Gln Lys Glu Thr His Gln Arg His Ala Ala
1               5                   10                  15

<210> SEQ ID NO 197
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 197

His Asn His Met Gln Glu Arg Tyr Thr Asp Pro Gln His Ser Pro Ser
1               5                   10                  15

Val Asn Gly Leu
            20

<210> SEQ ID NO 198
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 198

Thr Ala Glu Ile Asp Ser Ser Lys Asn Pro Asn Pro His Pro Gln Arg
1               5                   10                  15

Ser Trp Thr Asn
            20

<210> SEQ ID NO 199
<211> LENGTH: 17
<212> TYPE: PRT
<213> ORGANISM: artificial sequence
<220> FEATURE:
<223> OTHER INFORMATION: N terminal constant region

<400> SEQUENCE: 199

Met His His His His His His Ser Gly Ser Ser Ser Gly Ser Gly Ser
1               5                   10                  15

Gly

<210> SEQ ID NO 200
<211> LENGTH: 16
<212> TYPE: PRT
<213> ORGANISM: artificial sequence
<220> FEATURE:
<223> OTHER INFORMATION: C terminal constant region
```

-continued

```
<400> SEQUENCE: 200

Thr Ser Gly Gly Ser Ser Gly Ser Ser Leu Gly Val Ala Ser Ala Ile
1               5                   10                  15

<210> SEQ ID NO 201
<211> LENGTH: 28
<212> TYPE: RNA
<213> ORGANISM: artificial sequence
<220> FEATURE:
<223> OTHER INFORMATION: Synthetic oligonucleotide linker
<220> FEATURE:
<221> NAME/KEY: misc_feature
<222> LOCATION: (1)..(10)
<223> OTHER INFORMATION: 2'-O-methylation

<400> SEQUENCE: 201
uagcggaugc aaaaaaaaaa aaaaaaaa                                          28

<210> SEQ ID NO 202
<211> LENGTH: 42
<212> TYPE: DNA
<213> ORGANISM: artificial sequence
<220> FEATURE:
<223> OTHER INFORMATION: primer

<400> SEQUENCE: 202
taatacgact catagggaca attactattt acaattacaa tg                          42

<210> SEQ ID NO 203
<211> LENGTH: 39
<212> TYPE: DNA
<213> ORGANISM: artificial sequence
<220> FEATURE:
<223> OTHER INFORMATION: primer

<400> SEQUENCE: 203
aattaaatag cggatgctac accaagacta gaaccgctg                              39

<210> SEQ ID NO 204
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 204

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 205
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 205

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25
```

<210> SEQ ID NO 206
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 206

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 207
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 207

Arg Asn Asn Lys Gly Ser Lys Lys Val Asp Asp Lys Arg Arg Lys Thr
1               5                   10                  15

Val His Ser Thr Lys Ser Arg Ala Lys Tyr Ser
            20                  25

<210> SEQ ID NO 208
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 208

Arg Asn Asn Lys Gly Ser Arg Lys Val Asp Asp Lys Arg Arg Lys Thr
1               5                   10                  15

Val His Asn Thr Lys Ser Arg Ala Lys Tyr Ser
            20                  25

<210> SEQ ID NO 209
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 209

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 210
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 210

Arg Asn Asn Lys Gly Ser Lys Lys Val Asp Asp Lys Arg Arg Lys Ala
1               5                   10                  15

Val His Asn Lys Lys Ser Arg Ala Lys Tyr Ser
            20                  25

```
<210> SEQ ID NO 211
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 211

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 212
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 212

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 213
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (2)..(2)
<223> OTHER INFORMATION: Xaa = Asn or Asp
<220> FEATURE:
<221> NAME/KEY: MISC_FEATURE
<222> LOCATION: (7)..(7)
<223> OTHER INFORMATION: Xaa = Lys or Arg
<220> FEATURE:
<221> NAME/KEY: MISC_FEATURE
<222> LOCATION: (9)..(9)
<223> OTHER INFORMATION: Xaa = Ala or Val
<220> FEATURE:
<221> NAME/KEY: MISC_FEATURE
<222> LOCATION: (16)..(16)
<223> OTHER INFORMATION: Xaa = Ala or Thr
<220> FEATURE:
<221> NAME/KEY: MISC_FEATURE
<222> LOCATION: (19)..(19)
<223> OTHER INFORMATION: Xaa = Ser or Asn
<220> FEATURE:
<221> NAME/KEY: MISC_FEATURE
<222> LOCATION: (20)..(20)
<223> OTHER INFORMATION: Xaa = Lys or Thr
<220> FEATURE:
<221> NAME/KEY: MISC_FEATURE
<222> LOCATION: (21)..(21)
<223> OTHER INFORMATION: Xaa = Lys or Arg
<220> FEATURE:
<221> NAME/KEY: MISC_FEATURE
<222> LOCATION: (26)..(26)
<223> OTHER INFORMATION: Xaa = His, Tyr, or Phe

<400> SEQUENCE: 213

Arg Xaa Asn Lys Gly Ser Xaa Lys Xaa Asp Asp Lys Arg Arg Lys Xaa
1               5                   10                  15

Val His Xaa Xaa Xaa Ser Arg Ala Lys Xaa Ser
            20                  25
```

<210> SEQ ID NO 214
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 214

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 215
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 215

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 216
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (5)..(5)
<223> OTHER INFORMATION: Xaa = Leu or Phe
<220> FEATURE:
<221> NAME/KEY: MISC_FEATURE
<222> LOCATION: (23)..(23)
<223> OTHER INFORMATION: Xaa = any naturally occurring amino acid where
      Lys is preferred
<220> FEATURE:
<221> NAME/KEY: MISC_FEATURE
<222> LOCATION: (24)..(24)
<223> OTHER INFORMATION: Xaa = Trp or Asn
<220> FEATURE:
<221> NAME/KEY: MISC_FEATURE
<222> LOCATION: (25)..(25)
<223> OTHER INFORMATION: Xaa = Ser or Gly
<220> FEATURE:
<221> NAME/KEY: MISC_FEATURE
<222> LOCATION: (27)..(27)
<223> OTHER INFORMATION: Xaa = Lys or Pro

<400> SEQUENCE: 216

Gln Arg Arg Lys Xaa Arg His Pro Lys Glu Lys Trp Phe Gly Trp Ser
1               5                   10                  15

Glu Lys Lys Val Ile Lys Xaa Xaa Xaa Arg Xaa
            20                  25

<210> SEQ ID NO 217
<211> LENGTH: 27
<212> TYPE: PRT
<213> ORGANISM: artificial sequence
<220> FEATURE:
<223> OTHER INFORMATION: Calcium carbonate binding peptide

```
<400> SEQUENCE: 217

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 218
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 218

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25

<210> SEQ ID NO 219
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 219

Trp Lys Val Lys Arg Arg Met Val Thr Arg Thr Tyr Glu Phe Met Gly
1               5                   10                  15

Lys Lys Pro Cys Met Met Leu Thr Lys Arg Leu
            20                  25

<210> SEQ ID NO 220
<211> LENGTH: 26
<212> TYPE: PRT
<213> ORGANISM: artificial sequence
<220> FEATURE:
<223> OTHER INFORMATION: Calcium carbonate binding peptide

<400> SEQUENCE: 220

Lys Lys Ser Asn Lys Gly His His Ser Lys Ala Lys Gln Lys Arg Pro
1               5                   10                  15

His Gly Gly Lys Ala Gln Asn Lys Asn Thr
            20                  25

<210> SEQ ID NO 221
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 221

Arg Ala His Lys Glu Arg Phe Val Val Arg Gln Ile Gly Arg Ser Gln
1               5                   10                  15

Gly Tyr Lys Thr Trp Gln Cys Val Arg Val Ala
            20                  25

<210> SEQ ID NO 222
<211> LENGTH: 27
<212> TYPE: PRT
<213> ORGANISM: artificial sequence
<220> FEATURE:
<223> OTHER INFORMATION: Calcium carbonate binding peptide
```

```
<400> SEQUENCE: 222

Ser Gln Lys Pro Lys Gly His Lys Val Lys Val Val Val Lys Leu Cys
1               5                   10                  15

Lys Arg Pro Tyr Trp Arg Met Leu Asn Thr Ala
            20                  25

<210> SEQ ID NO 223
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (11)..(11)
<223> OTHER INFORMATION: Xaa = any naturally occurring amino acid

<400> SEQUENCE: 223

Asn His Gly Cys Pro Val Asn Trp Lys Val Xaa Asn Pro Pro Arg Gly
1               5                   10                  15

Trp Gln Arg Leu Asn His Cys Lys Trp Trp Asn
            20                  25

<210> SEQ ID NO 224
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 224

Arg Asn Ser Arg His Lys Glu Trp Arg Arg Tyr Lys Arg Thr His Val
1               5                   10                  15

His Ser His Glu Phe Tyr His Val Glu Cys Trp
            20                  25

<210> SEQ ID NO 225
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 225

His Arg Ser Glu Lys Pro Lys Asn Val Asn Tyr Lys Arg Gly Tyr Trp
1               5                   10                  15

Glu Arg Gly Asn Gln Lys Lys His Gly Pro Gly
            20                  25

<210> SEQ ID NO 226
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 226

His Glu Arg Thr Arg Arg Gly Lys Pro Asp Arg Gln Lys Thr Thr His
1               5                   10                  15

Glu Lys Arg Arg Gln Gly Leu Trp Ile Phe Met
            20                  25
```

```
<210> SEQ ID NO 227
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 227

Pro Trp Gly Thr Asn Lys Arg Gln Lys His Lys Val His Glu Ala Lys
1               5                   10                  15

Ala Leu Lys Lys Ser Leu Trp Tyr Ser Asn Ser
            20                  25

<210> SEQ ID NO 228
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 228

Arg Arg Gly Val Val Leu Cys His Thr His Arg Asn Lys Arg Ile Arg
1               5                   10                  15

Leu Ala Tyr Ser Val Thr Lys Lys Ala Trp Ala
            20                  25

<210> SEQ ID NO 229
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 229

Glu Arg Ile Arg Trp Arg Arg Leu Ser Ala Glu Ile Arg Ala His Lys
1               5                   10                  15

Trp Ser Val Leu Lys Phe Arg Leu Ser Cys Met
            20                  25

<210> SEQ ID NO 230
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 230

Lys Thr Lys Glu Lys Lys Lys Glu Val Lys Leu His Lys Lys Ser Leu
1               5                   10                  15

Ser Leu Val Leu Leu Ala Asp Leu Trp Arg Leu
            20                  25

<210> SEQ ID NO 231
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 231

Leu Gly Lys Lys His Lys Gln His Ser Lys Val Gly His Gly Lys Leu
1               5                   10                  15

Ser Thr Arg Phe Leu Arg Arg Ser Lys Leu Phe
            20                  25
```

```
<210> SEQ ID NO 232
<211> LENGTH: 5
<212> TYPE: PRT
<213> ORGANISM: artificial sequence
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any naturally occurring amino acid except
      Pro, Glu, Asp, Gln, Lys, and Arg.

<400> SEQUENCE: 232

Asp Met Gln Asp Xaa
1               5
```